(12) United States Patent
Belisle et al.

(10) Patent No.: US 7,776,341 B2
(45) Date of Patent: Aug. 17, 2010

(54) BIOMARKERS OF TUBERCULOSIS THAT DISTINGUISH DISEASE CATEGORIES: USE AS SERODIAGNOSTIC ANTIGENS

(75) Inventors: John T. Belisle, Fort Collins, CO (US); Mark J. Sartain, Fort Collins, CO (US); Suman Laal, Cortlandt Manor, NY (US)

(73) Assignees: Colorado State University Research Foundation, Fort Collins, CO (US); New York University, New York, NY (US)

( * ) Notice: Subject to any disclaimer, the term of this patent is extended or adjusted under 35 U.S.C. 154(b) by 0 days.

(21) Appl. No.: 11/837,264

(22) Filed: Aug. 10, 2007

(65) Prior Publication Data

US 2008/0171345 A1    Jul. 17, 2008

Related U.S. Application Data

(60) Provisional application No. 60/836,653, filed on Aug. 10, 2006.

(51) Int. Cl.
*A61K 39/04* (2006.01)
*A61K 39/00* (2006.01)
*A61K 39/02* (2006.01)

(52) U.S. Cl. ............. 424/248.1; 424/184.1; 424/185.1; 424/234.1; 530/300; 530/350; 536/23.1

(58) Field of Classification Search ............... 424/184, 424/185.1, 234.1, 248.1; 530/300, 350; 536/23.1, 536/23.7

See application file for complete search history.

(56) References Cited

U.S. PATENT DOCUMENTS

| | | | | |
|---|---|---|---|---|
| 6,517,845 B1 * | 2/2003 | Lee et al. | | 424/248.1 |
| 6,641,814 B1 * | 11/2003 | Andersen et al. | | 424/190.1 |
| 2003/0167524 A1 * | 9/2003 | Rooijen et al. | | 800/281 |
| 2003/0219443 A1 * | 11/2003 | Lee et al. | | 424/168.1 |
| 2004/0214165 A1 * | 10/2004 | Gicquel et al. | | 435/6 |

FOREIGN PATENT DOCUMENTS

WO        WO 02/04018       *  1/2002

* cited by examiner

*Primary Examiner*—Rodney P. Swartz
(74) *Attorney, Agent, or Firm*—Browdy and Neimark, PLLC

(57) ABSTRACT

Mycobacterial proteins from culture filtrate or cytosol are disclosed as being useful B cell antigens for early diagnosis of mycobacterial disease, particularly in humans. These proteins include four that had not previously been recognized as B cell antigens (LppZ protein encoded by Mtb gene Rv3006; SodC protein encoded by Mtb gene Rv0432; BfrB protein encoded by Mtb gene Rv3841 and TrxC protein encoded by Mtb gene Rv3914). Antigenic compositions include these proteins and/or peptide fragments thereof, in various combinations with each other or with one or more of a set of 10 additional Mtb proteins known to be antigens (in particular early antigens. Methods and kits for using these antigenic composition for early diagnosis of mycobacterial infection and disease are also disclosed.

33 Claims, 7 Drawing Sheets

BIOMARKERS OF TUBERCULOSIS THAT DISTINGUISH DISEASE CATEGORIES: USE AS SERODIAGNOSTIC ANTIGENS

This application claims priority from U.S. provisional application No. 60/836,653, filed Aug. 10, 2006, and incorporates by reference all the contents thereof.

STATEMENT OF RIGHTS TO INVENTIONS MADE UNDER FEDERALLY SPONSORED RESEARCH

This invention was funded in part by grants and contracts from the National Institute of Health, specifically, NIAID grant RO1 AI-056257 and Contract NO1 AI-75320, which provides to the United States government certain rights in this invention.

BACKGROUND OF THE INVENTION

1. Field of the Invention

The invention in the field of microbiology, immunology and medicine relates to novel proteins, peptides and antigenic compositions for early diagnosis of mycobacterial disease, kits comprising such compositions, and serodiagnostic methods using such compositions.

2. Description of the Background Art

Recent World Health Organization data show that the global incidence of tuberculosis (TB) is increasing at 1% per year and that there are an estimated 8.8 million new cases each year (1). One concerning fact is less than half of the 8.8 million estimated cases are diagnosed as smear positive. This underscores the need for a rapid, sensitive diagnostic test to aid TB control efforts. The development of such a test has proven to be one of the greatest challenges in TB research.

In recent years there has been renewed interest in developing antibody-based diagnostics that utilize multiple antigens to achieve high levels of sensitivity and specificity (2). The success of a serodiagnostic test for TB hinges on its ability to detect multiple disease categories, including pauci- and multibacillary forms, pediatric cases, and patients co-infected with human immunodeficiency virus (HIV). Previous work from our laboratories identified several antigens that provide high sensitivity and specificity when used in an ELISA format (3-9). Furthermore, this work highlighted differential antigen reactivity based on the disease category (3, 5, 6, 8-10). However, a complete analysis of patients' serological reactivity to a large proportion of the *Mycobacterium tuberculosis* (Mtb) proteome is hindered by the inability to evaluate the reactivity of the nearly 4,000 predicted proteins of Mtb in a high-throughput fashion.

Over the past several years, protein microarrays have shown considerable potential for detecting antigen-antibody interactions on a proteomic scale (11-13). As a proof-of-principle, Bacarese-Hamilton, et al. (14) immobilized recombinant antigens of various pathogens to glass slides, and human antibodies specific for each antigen were detected in sub-picogram amounts. This microarray assay also performed at the same level of efficiency as conventional ELISA-based methods in differentiating between positive and negative sera. Microarray technology has now been extended to characterize antibody responses generated upon vaccination with *Yersinia pestis* (15) and vaccinia virus (16). Protein microarrays accommodate thousands of individual antigens or antigen pools on a single slide, and automation allows for hundreds of slides to be generated at once. Moreover, this methodology is facile and allows reproducible screening of sera from a large number of individual patients.

A critical element of tuberculosis control is early and sensitive diagnosis of infection and disease. The present inventors' laboratories recently showed that different stages of disease were distinguishable via two-dimensional western blot analyses of *Mycobacterium tuberculosis* culture filtrate proteins (CFPs). However, this methodology is not suitable for high-throughput testing. Advances in protein microarray technology provide a realistic mechanism to screen a large number of serum samples against thousands of proteins to identify biomarkers of disease categories. Using such an approach, the present inventors identified four Mtb proteins, and peptides thereof as being of particular value for serodiagnosis of tuberculosis at both early and later stages of the disease.

SUMMARY OF THE INVENTION

Abbreviations

2-D, two-dimensional; AFB, acid-fast bacilli; AIEX, anion-exchange; AvSNR, averaged signal-to-noise ratio; BCA, bicinchoninic assay; CFP, culture filtrate protein; CytP, cytosolic protein; HIV, human immunodeficiency virus; LAM, lipoarabinomannan; mAbs, monoclonal antibodies; MS/MS, tandem mass spectrometry; Mtb, *Mycobacterium tuberculosis*; MudPIT, multidimensional protein identification technology; NAvSNR, normalized averaged signal-to-noise ratio; ORF, open-reading frame; PPD, purified-protein derivative; RP, reversed phase; RT, room temperature; SD, standard deviation; SNR, signal-to-noise ratio; TB, tuberculosis; WCL, whole-cell lysate Techniques were established for separation of native *M. tuberculosis* cytosol proteins (CytP) and culture filtrate proteins (CFP), resulting in 960 unique protein fractions that were used to generate protein microarrays. Evaluation of serological reactivity from 42 patients in three tuberculosis disease categories and healthy individuals who reacted positively to a PPDs skin test (PPD$^+$) demonstrated that HIV-negative cavitary- and noncavitary-TB patients recognized 126 and 59 fractions, respectively. Sera from HIV patients co-infected with TB (HIV$^+$TB$^+$) recognized 20 fractions, of which five overlapped with those recognized by non-HIV TB patients and 15 were unique to the HIV$^+$TB$^+$ disease category.

The term "recognize" or "recognized" when referring to an antigen and an antibody means that the antibody binds the antigen (whether it be a full length protein or shorter peptide fragment) in a way that can be detected in an immunoassay or otherwise observed. "Specific recognition" refers to the fact that antibodies are highly specific in their binding and can discriminate a antigen for which they are specific from an antigen from which they are not specific; in the latter case, the antibody does not bind or binds at a very low affinity or in a manner that is not detected in an immunoassay.

Identification of antigens within the reactive fractions yielded eleven products recognized by both cavitary- and noncavitary-TB patients, and four proteins (HspX, MPT64, PstS1, and TrxC) specific for cavitary-TB patients. Moreover, four novel B cell antigens (BfrB, LppZ, SodC, and TrxC) of human tuberculosis were identified and their sequences are set forth below.

The present invention is directed to an isolated *M. tuberculosis* (Mtb) protein or peptide selected from the following group:

(a) LppZ protein, encoded by Mtb gene Rv3006, the amino acid sequence of which is SEQ ID NO:1 or a peptide fragment thereof that is recognized by an antibody from a subject infected with Mtb;
(b) an isolated peptide fragment of Mtb protein SodC (SEQ ID NO:2) encoded by Mtb gene Rv0432, which peptide fragment is recognized by an antibody from a subject infected with Mtb;
(c) BfrB protein, encoded by Mtb gene Rv3841, the amino acid sequence of which is SEQ ID NO:3, or a peptide fragment thereof that is recognized by an antibody from a subject infected with Mtb; and
(d) TrxC protein, encoded by Mtb gene Rv3914, the amino acid sequence of which is SEQ ID NO:4 and is, or a peptide fragment thereof that is recognized by an antibody from a subject infected with Mtb.

Examples of preferred peptide fragments of the above four proteins are ones that comprise B cell epitopes, are about 20 amino acids in length and represent 10 amino acid overlaps with their adjacent sequences in the parent protein. Preferred peptides of the invention include:
(a) an LppZ peptide the sequence of which is SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, or SEQ ID NO:51;
(b) a peptide of said SodC protein, the sequence of which is SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, or SEQ ID NO:74;
(c) a peptide of said BfrB protein the sequence of which is SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, or SEQ ID NO:92; or
(d) a peptide of said TrxC protein the sequence of which is SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, or SEQ ID NO:103.

In one preferred embodiment, the peptide is a BfrB peptide selected from the group consisting of SEQ ID NO:75, SEQ ID NO:78, SEQ ID NO:79, SEQ ID NO:80, SEQ ID NO:82 and SEQ ID NO:92.

In another preferred embodiment, the peptide is a TrxC peptide listed in (d), above.

The present invention is also directed to oligomers or multimers of a peptide as above, which are either fused directly or indirectly via peptide linker or spacer which may be a cleavable linker.

Also provided herein is an antigenic composition useful for detection, preferably early detection, of Mtb disease or infection comprising an Mtb antigen that is a protein or peptide as noted above wherein the protein/peptide includes an epitope recognized by an antibody in a subject infected with Mtb.

In one preferred embodiment, the invention is directed to antigenic composition useful for detection and profiling of Mtb disease or infection comprising two or more, or three or more Mtb antigens which antigens are selected from the above proteins or peptide fragments. The peptides of this antigenic composition may be a fragment of one or more of these proteins.

The antigenic composition of this invention may further comprises one or more additional Mtb proteins, or a peptide fragment thereof that includes an epitope recognized by an antibody in a subject infected with Mtb, the protein being selected from:
(a) an isolated PstS1 protein encoded by Mtb gene Rv0934 the amino acid sequence of which is SEQ ID NO:5;
(b) an isolated Apa/ModD protein encoded by Mtb gene Rv1860 the amino acid sequence of which is SEQ ID NO:6;
(c) an isolated Ag85A protein encoded by Mtb gene Rv3804c the amino acid sequence of which is SEQ ID NO:7;
(d) an isolated Ag85B protein encoded by Mtb gene Rv1886c the amino acid sequence of which is SEQ ID NO:8;
(e) an isolated GlcB protein encoded by Mtb gene Rv1837c the amino acid sequence of which is SEQ ID NO:9;
(f) an isolated protein encoded by Mtb gene Rv3881c the amino acid sequence of which is SEQ ID NO:10;
(g) an isolated SecE2 protein encoded by Mtb gene Rv0379 the amino acid sequence of which is SEQ ID NO:11;
(h) an isolated MPT64 protein encoded by Mtb gene Rv1980c the amino acid sequence of which is SEQ ID NO:12;
(i) an isolated HspX protein encoded by Mtb gene Rv2031c the amino acid sequence of which is SEQ ID NO:13; and
(j) an isolated LpqH protein encoded by Mtb gene Rv3763 the amino acid sequence of which is SEQ ID NO:14.

Also provided is an immunoassay composition that comprises the LppZ, SodC, BfrB or TrxC protein, a peptide thereof, or an antigenic composition as above, wherein the protein or peptide is immobilized to a solid support and preferably arranged in a format suitable for use in an ELISA or dipstick-based immunoassay.

This invention is directed to a method for the early detection of mycobacterial disease or infection in a subject, comprising assaying a biological fluid sample from a subject having symptoms of active tuberculosis, but before the onset of symptoms identifiable as advanced tuberculosis for the presence of antibodies specific for or reactive with an Mtb antigen selected from the above-noted isolated proteins, peptides or antigenic compositions.

Also included is a method for the early detection of mycobacterial disease or infection in a subject, comprising assaying a biological fluid or cell or tissue sample from a subject having symptoms of active tuberculosis, but before the onset of symptoms identifiable as advanced tuberculosis for the presence of one or more early *M. tuberculosis* early antigens that are present in the above-noted isolated protein or antigenic composition, using an antiserum or a monoclonal antibody specific for an epitope of the early antigen, wherein the presence of the one or more early antigens is indicative of the presence of the disease or infection.

A related method comprises assaying a biological fluid sample from a subject having symptoms of active tuberculosis, but before the onset of symptoms identifiable as advanced tuberculosis for the presence of immune complexes consisting of one or more early Mtb antigens complexed with an antibody specific for the antigen, which antigen is a protein or peptide as described above.

The above method is preferably an EIA/ELISA or a dipstick-based immunoassay.

The method may further include performance of a test that detects mycobacterial bacilli in a sample of sputum or other body fluid of the subject.

The biological fluid or body fluid used in the method is preferably is serum, urine or saliva.

The above method may further comprise, prior to the assaying step, the step of removing, from the sample, antibodies specific for cross-reactive epitopes or antigens of proteins present in *M. tuberculosis* and in other bacterial genera, preferably by immunoadsorption of the sample with *E. coli* antigens.

In the above methods, the subject is preferably a human, and the method is particularly useful for HIV-1$^+$ subjects and/or those is at high risk for tuberculosis.

The invention includes a kit useful for early detection of Mtb disease or infection as above, the kit comprising:

(a) an early Mtb antigen or antigens in the form of the isolated protein or peptide noted above in combination with (b) reagents necessary for detection of antibodies which bind to the *M. tuberculosis* protein or peptide; and (c) optionally, a set of instructions for carrying out the detection.

In the above kit and method, one or more of the Mtb proteins or peptide antigens is a recombinant protein, glycoprotein, lipoprotein, or a recombinant or synthetic epitope-bearing peptide.

DESCRIPTION OF THE PREFERRED EMBODIMENTS

Figure 1:
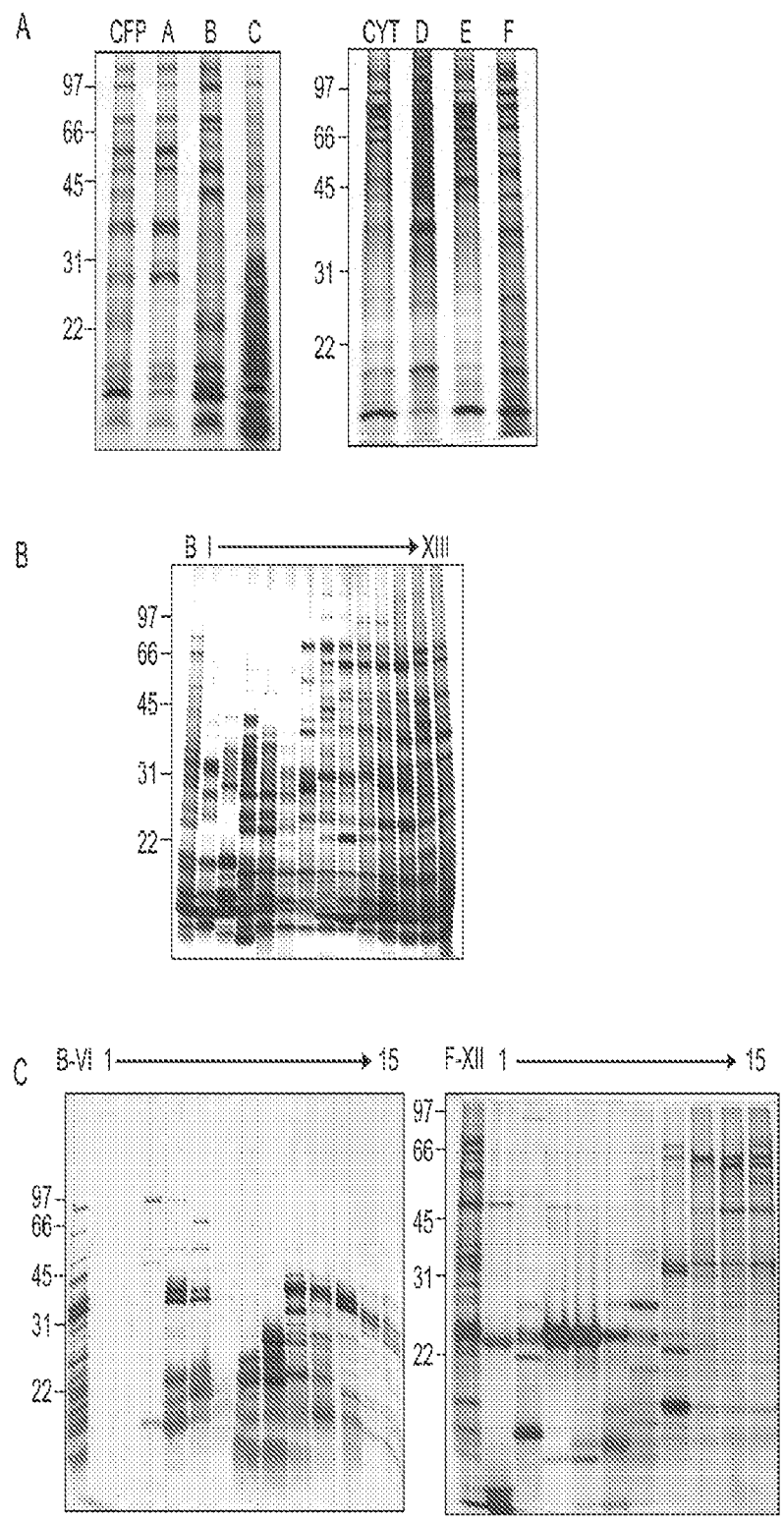
FIG. 1. Mtb CFPs and CytPs were subjected to a multi-dimensional separation scheme. (A) Silver stained SDS-PAGE analysis of fractionation obtained by ammonium-sulfate precipitation of CFP and cytosol. CFP, unfractionated CFP; lane A, 42% ammonium-sulfate precipitate of the CFP; lane B, 67% ammonium-sulfate precipitate of the CFP; lane C, 67% ammonium-sulfate soluble material of the CFP; CYT, unfractionated cytosol; lane D, 29% ammonium-sulfate precipitate of the cytosol; lane E, 44% ammonium-sulfate precipitate of the cytosol; and lane F, 44% ammonium-sulfate soluble material of the cytosol. (B) Silver stained SDS-PAGE of strong AIEX chromatography fractions using the 67% ammonium-sulfate precipitate of the CFP as an example. Lane B, unfractionated material; lanes I-XIII are the sequential AIEX fractions. (C) Silver stained SDS-PAGE of RP chromatography fractions using the B-VI AIEX fraction of the 67% ammonium-sulfate precipitate of the CFP and the F-XII AIEX fraction of the 44% ammonium-sulfate soluble material of the cytosol as examples. Lane B-VI and F-XII, unfractionated material; lanes 1-15 are the sequential RP fractions.

Due to the absence of a complete Mtb open reading frame library, the present inventors produced a first generation Mtb protein microarray based on native proteins. A multi-dimensional separation strategy was devised to efficiently resolve native proteins found in the cytosol (CytPs) and culture filtrate (CFPs) of Mtb. This resulted in 960 relatively simple protein fractions from two highly complex protein pools. These fractions were spotted to nitrocellulose slides and probed with sera from purified-protein-derivative positive (PPD$^+$) healthy controls, cavitary-TB, noncavitary-TB, and HIV and Mtb co-infected patients. The resulting analyses corroborated the present inventors' earlier two-dimensional (2-D) immunoblot based experiments, confirming that a subset of antigens is recognized early in TB disease progression. Furthermore, four proteins specific for cavitary-TB patients were identified, and four novel antigens previously undetected by other methods were defined as serodiagnostic targets.

In the following description, reference will be made to various methodologies known to those of skill in the art of immunology. Publications and other materials setting forth such known methodologies to which reference is made are incorporated herein by reference in their entireties as though set forth in full. Standard reference works setting forth the general principles of immunology as well as details of mAb production and characterization, and immunoassay procedures, include: Harlow, E. et al., *Antibodies: A Laboratory Manual*, Cold Spring Harbor Laboratory Press, Cold Spring Harbor, N.Y., 1988) and Harlow, E. et al., *Using Antibodies: A Laboratory Manual Portable Protocol NO. I*, Cold Spring Harbor Laboratory Press, Cold Spring Harbor, N.Y., 1998); A. K. Abbas et al., *Cellular and Molecular Immunology* (Fourth Ed.), W.B. Saunders Co., Philadelphia, 2000; C. A. Janeway et al., *Immunobiology. The Immune System in Health and Disease*, Fourth ed., Garland Publishing Co., New York, 1999; Roitt, I. et al., eds, *Immunology*, C. V. Mosby Co., St. Louis, Mo. (2001); Klein, J., *Immunology*, $2^{nd}$ edition, Blackwell Scientific Publications, Inc., Cambridge, Mass., (1997); Roitt, I et al., eds., *Roitt's Essential Immunology*, Blackwell Scientific Publications, Oxford (2001);

Immunoassay methods are also described in Coligan, J. E. et al., eds., *Current Protocols in Immunology*, Sec. 2.4.1, Wiley-Interscience, New York, 1992 (or current edition); Bizollon, Ch. A., ed., *Monoclonal Antibodies and New Trends in Immunoassays*, Elsevier, N.Y., 1984; Butler, J. E., ELISA (Chapter 29), In: van Oss, C. J. et al., (eds), *IMMUNOCHEMISTRY*, Marcel Dekker, Inc., New York, 1994, pp. 759-803; Butler, J E, The Behavior of Antigens and Antibodies Immobilized on a Solid Phase (Chapter 11) In: *STRUCTURE OF ANTIGENS*, Vol. 1 (Van Regenmortel, M., CRC Press, Boca Raton 1992, pp. 209-259; Butler, J E (ed.), *Immunochemistry of Solid-Phase Immunoassay*, CRC Press, Boca Raton, 1991.

As used herein, definitions of the terms "early" and "late" in reference to (1) Mtb infection or disease, or the subject having the infection or disease, (2) the antibody response to an Mtb antigen, (3) an Mtb antigen itself or (4) a diagnostic assay, are based on terms of the stage of development of TB. Early and late (or advanced) TB are defined in the table below.

Thus, a subject with early TB is asymptomatic or, more typically, has one or more "constitutional symptoms" (e.g., fever, cough, weight loss). In early TB, Mtb bacilli are too few to be detectable microscopically as acid-fast bacilli in smears of sputum or another body fluids, primarily those fluids associated with the lungs (such as bronchial washings, bronchoalveolar lavage, pleural effusion). However, in these subjects, Mtb bacilli are present and culturable, which means that they can be grown in culture from the above body fluids. Finally, early TB subjects may have radiographically evident pulmonary lesions which may include infiltration but are without cavitation. Any antibody that arises by, and is detectable during, such early stages is termed an "early antibody" and any Mtb antigen recognized by such antibodies is termed an "early antigen." The fact that an antibody is characterized as "early" does not mean that this antibody is absent in advanced TB. Rather, such antibodies are expected to persist across the progression of early TB to the advanced stage.

| | |
|---|---|
| Early TB | 1. Smear of sputum, bronchial washing, bronchoalveolar lavage or pleural effusion is negative for acid fast bacilli |
| | 2. Direct culture of sputum, bronchial washing, bronchoalveolar lavage or pleural effusion is positive for acid fast bacilli |
| | 3. Chest x-ray is normal or shows infiltration in the lungs |
| | 4. Constitutional symptoms are present (fever, cough, appetite and weight loss) |
| Late/Advanced TB | 1. Smear of sputum, bronchial washing, bronchoalveolar lavage or pleural effusion is positive (with possible hemoptysis) |

-continued

| | |
|---|---|
| | 2. Direct culture of sputum, bronchial washing, bronchoalveolar lavage or pleural effusion is positive |
| | 3. Chest x-ray shows cavitary lesions in the lungs |
| | 4. Constitutional symptoms are present (see above) |

Accordingly, the term "late" or "advanced" is characterized in that the subject has frank clinical disease and more advanced cavitary lesions in the lungs. In late TB, Mtb bacilli are not only culturable from smears of sputum and/or the other body fluids noted above, but also present in sufficient numbers to be detectable as acid-fast bacilli in smears of these fluids. Again, "late TB" or "late mycobacterial disease of infection" is used interchangeably with "advanced TB" or "advanced mycobacterial disease or infection." An antibody that first appears after the onset of diagnostic clinical and other characterizing symptoms (including cavity pulmonary lesions) is a late antibody, and an antigen recognized by such a late antibody (but not by an early antibody) would be termed a late antigen.

To be useful in accordance with this invention, an early diagnostic assay must permit rapid diagnosis of Mtb disease at a stage earlier than that which could have been diagnosed by conventional clinical diagnostic methods, namely, by radiologic examination and bacterial smear and culture or by other laboratory methods available prior to this invention. (Culture positivity is the final confirmatory test but takes two weeks and more.)

An objective of the invention is to define, obtain and characterize the antigens of Mtb expressed by the bacterium in vivo during early infection and TB. These antigens are evaluated for their utility as markers of early disease that may be used to monitor suspected or high-risk individuals to identify those with active, subclinical infection and initiate treatment earlier than would have been done in the absence of such a diagnosis.

Mycobacterial Antigen Compositions

The preferred mycobacterial antigenic composition is a substantially isolated, purified or recombinantly produced preparation of one or more of the Mtb proteins described herein, or a peptide fragment thereof. Alternatively, the antigen composition may be a substantially pure preparation containing one or more Mtb antigens, in the form of the epitope-bearing protein or epitope-bearing peptides which are capable of being recognized by, and bound by, antibodies of an Mtb infected subject. Such epitopes may be in the form of peptide fragments of these proteins or other "functional derivatives" of Mtb proteins as described below.

By "functional derivative" is meant a "fragment," "variant," "analogue," or "chemical derivative" of an early antigen protein, which terms are defined below. A functional derivative retains at least a portion of the function of the protein which permits its utility in accordance with the present invention—primarily the capacity to bind to (which is the equivalent of "be bound by") an early antibody. A "fragment" refers to any subset of the molecule, that is, a shorter peptide. A "variant" refers to a molecule substantially similar to either the entire protein or the peptide fragment thereof. A variant peptide may be conveniently prepared by direct chemical synthesis or by recombinant means. An "analogue" of the protein or peptide refers to a non-natural molecule substantially similar to either the entire molecule or a fragment thereof. A "chemical derivative" of the antigenic protein or peptide contains additional chemical moieties not normally part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

Several proteins, glycoproteins and lipoproteins in culture filtrates of Mtb organisms, cytosol of Mtb or on the surface of Mtb organisms are the preferred sources of early Mtb antigens. The secreted proteins may also be present in cellular preparations of the bacilli. Thus, these early antigens are not intended to be limited to the secreted protein form. The proteins are characterized at various places below.

The present inventors are the first to have discovered, isolated and used three Mtb proteins LppZ, BfrB and TrxC that were heretofore known only via annotations of the genomic map of Mtb or by gene expression studies. This invention is the first disclosure of these proteins and their peptide fragments as B cell antigens in humans. The inventors are the first to have recognized the utility of a fourth Mtb protein, SodC as a B cell antigen and to consider and delineate peptides thereof for similar uses.

(1) LppZ protein encoded by the Mtb gene Rv3006 has the following sequence (SEQ ID NO:1):
    *MWTTRLVRSG LAALCAAVLV SSG*CARFNDA QSQPFTTEPE

LRPQPSSTPP PPPPLPPVPF PKECPAPGVM QGCLESTSGL

IMGIDSKTAL VAERITGAVE EISISAEPKV KTVIPVDPAG

DGGLMDIVLS PTYSQDRLMY AYISTPTDNR VVRVADGDIP

KDILTGIPKG AAGNTGALIF TSPTTLVVMT GDAGDPALAA

DPQSLAGKVL RIEQPTTIGQ TPPTTALSGI GSGGGLCIDP

VDGSLYVADR TPTADRLQRI TKNSEVSTVW TWPDKPGVAG

CAAMDGTVLV NLINTKLTVA VRLAPSTGAV TGEPDVVRKD

THAHAWALRM SPDGNVWGAT VNKTAGDAEK LDDVVFPLFP

QGGGFPRNND DKT (The N-terminal secreted signal sequence is italicized and underscored.)

(2) SodC protein encoded by Mtb gene Rv0432 has the following sequence (SEQ ID NO:2):
    *MPKPADHRNH AAVSTSVLSA LFLGAGAALL SA*CSSPQHAS

TVPGTTPSIW TGSPAPSGLS GHDEESPGAQ SLTSTLTAPD

GTKVATAKFE FANGYATVTI ATTGVGKLTP GFHGLHIHQV

GKCEPNSVAP TGGAPGNFLS AGGHYHVPGH TGTPASGDLA

SLQVRGDGSA MLVTTTDAFT MDDLLSGAKT AIIIHAGADN

FANIPPERYV QVNGTPGPDE TTLTTGDAGK RVACGVIGSG (The N-terminal secreted signal sequence is italicized and underscored.)

(3) BfrB protein encoded by Mtb gene Rv3841, has the following sequence (SEQ ID NO:3):
    MTEYEGPKTK FHALMQEQIH NEFTAAQQYV AIAVYFDSED

LPQLAKHFYS QAVEERNHAM MLVQHLLDRD LRVEIPGVDT

VRNQFDRPRE ALALALDQER TVTDQVGRLT AVARDEGDFL

GEQFMQWFLQ EQIFEVALMA TLVRVADRAG ANLFELENFV

AREVDVAPAA SGAPHAAGGRL (4) TrxC protein encoded by Mtb gene Rv3914 has the following sequence (SEQ ID NO:4):
    MTDSEKSATI KVTDASFATD VLSSNKPVLV DFWATWCGPC

KMVAPVLEEI ATERATDLTV AKLDVDTNPE TARNFQVVSI

PTLILFKDGQ PVKRIVGAKG KAALLRELSD VVPNLN

As described in the Examples, these antigens were initially identified based on reactivity to an antigen-specific mAb and MS/MS analyses.

Peptide fragments of the above proteins that comprise an antigenic epitope recognized by an antibody in a subject with TB, preferably early TB, but also including cavitary or late TB, are included herein. Preferred peptides are about 20 residues in length, though they can be as short as 7 residues, or whatever length is required to form a serologically detectable epitope in any type of immunoassay, preferably in ELISA. The peptides listed below are 20-mers, and those derived from a given protein are related to one another with 10 residue overlaps as shown in Tables 1-4 below. For utility in the detection of TB, a peptide should be recognized and bound by an anti-Mtb antibody present in subject infected with Mtb organisms.

TABLE 1

Exemplary Peptides of LppZ (SEQ ID NO:1)

| Peptide Name | AA Sequence | SEQ ID NO: |
|---|---|---|
| LppZ-1 | MWTTRLVRSG LAALCAAVLV | 15 |
| LppZ-2 | LAALCAAVLV SSGCARFNDA | 16 |
| LppZ-3 | SSGCARFNDA QSQPFTTEPE | 17 |
| LppZ-4 | QSQPFTTEPE LRPQPSSTPP | 18 |
| LppZ-5 | LRPQPSSTPP PPPPLPPVPF | 19 |
| LppZ-6 | PPPPLPPVPF PKECPAPGVM | 20 |
| LppZ-7 | PKECPAPGVM QGCLESTSGL | 21 |
| LppZ-8 | QGCLESTSGL IMGIDSKTAL | 22 |
| LppZ-9 | IMGIDSKTAL VAERITGAVE | 23 |
| LppZ-10 | VAERITGAVE EISISAEPKV | 24 |
| LppZ-11 | EISISAEPKV KTVIPVDPAG | 25 |
| LppZ-12 | KTVIPVDPAG DGGLMDIVLS | 26 |
| LppZ-13 | DGGLMDIVLS PTYSQDRLMY | 27 |
| LppZ-14 | PTYSQDRLMY AYISTPTDNR | 28 |
| LppZ-15 | AYISTPTDNR VVRVADGDIP | 29 |
| LppZ-16 | VVRVADGDIP KDILTGIPKG | 30 |
| LppZ-17 | KDILTGIPKG AAGNTGALIF | 31 |
| LppZ-18 | AAGNTGALIF TSPTTLVVMT | 32 |
| LppZ-19 | TSPTTLVVMT GDAGDPALAA | 33 |
| LppZ-20 | GDAGDPALAA DPQSLAGKVL | 34 |
| LppZ-21 | DPQSLAGKVL RIEQPTTIGQ | 35 |

TABLE 1-continued

Exemplary Peptides of LppZ (SEQ ID NO:1)

| Peptide Name | AA Sequence | SEQ ID NO: |
|---|---|---|
| LppZ-22 | RIEQPTTIGQ TPPTTALSGI | 36 |
| LppZ-23 | TPPTTALSGI GSGGGLCIDP | 37 |
| LppZ-24 | GSGGGLCIDP VDGSLYVADR | 38 |
| LppZ-25 | VDGSLYVADR TPTADRLQRI | 39 |
| LppZ-26 | TPTADRLQRI TKNSEVSTVW | 40 |
| LppZ-27 | TKNSEVSTVW TWPDKPGVAG | 41 |
| LppZ-28 | TWPDKPGVAG CAAMDGTVLV | 42 |
| LppZ-29 | CAAMDGTVLV NLINTKLTVA | 43 |
| LppZ-30 | NLINTKLTVA VRLAPSTGAV | 44 |
| LppZ-31 | VRLAPSTGAV TGEPDVVRKD | 45 |
| LppZ-32 | TGEPDVVRKD THAHAWALRM | 46 |
| LppZ-33 | THAHAWALRM SPDGNVWGAT | 47 |
| LppZ-34 | SPDGNVWGAT VNKTAGDAEK | 48 |
| LppZ-35 | VNKTAGDAEK LDDVVFPLFP | 49 |
| LppZ-36 | LDDVVFPLFP QGGGFPRNND | 50 |
| LppZ-37 | VVFPLFPQGG GFPRNNDDKT | 51 |

TABLE 2

Exemplary Peptides of SodC (SEQ ID NO:2)

| Peptide Name | AA Sequence | SEQ ID NO: |
|---|---|---|
| SodC-1 | MMPKPADHRNH AAVSTSVLSA | 52 |
| SodC-2 | LAAVSTSVLSA LFLGAGAALL | 53 |
| SodC-3 | SLFLGAGAALL SACSSPQHAS | 54 |
| SodC-4 | QSACSSPQHAS TVPGTTPSIW | 55 |
| SodC-5 | LTVPGTTPSIW TGSPAPSGLS | 56 |
| SodC-6 | PTGSPAPSGLS GHDEESPGAQ | 57 |
| SodC-7 | PGHDEESPGAQ SLTSTLTAPD | 58 |
| SodC-8 | QSLTSTLTAPD GTKVATAKFE | 59 |
| SodC-9 | IGTKVATAKFE FANGYATVTI | 60 |
| SodC-10 | VFANGYATVTI ATTGVGKLTP | 61 |
| SodC-11 | EATTGVGKLTP GFHGLHIHQV | 62 |
| SodC-12 | KGFHGLHIHQV GKCEPNSVAP | 63 |
| SodC-13 | DGKCEPNSVAP TGGAPGNFLS | 64 |
| SodC-14 | PTGGAPGNFLS AGGHYHVPGH | 65 |
| SodC-15 | AAGGHYHVPGH TGTPASGDLA | 66 |
| SodC-16 | VTGTPASGDLA SLQVRGDGSA | 67 |

TABLE 2-continued

Exemplary Peptides of SodC (SEQ ID NO:2)

| Peptide Name | AA Sequence | SEQ ID NO: |
|---|---|---|
| SodC-17 | KSLQVRGDGSA MLVTTTDAFT | 68 |
| SodC-18 | AMLVTTTDAFT MDDLLSGAKT | 69 |
| SodC-19 | TMDDLLSGAKT AIIIHAGADN | 70 |
| SodC-20 | GAIIIHAGADN FANIPPERYV | 71 |
| SodC-21 | DFANIPPERYV QVNGTPGPDE | 72 |
| SodC-22 | RQVNGTPGPDE TTLTTGDAGK | 73 |
| SodC-23 | TTTLTTGDAGK RVACGVIGSG | 74 |

TABLE 3

Exemplary Peptides of BfrB (SEQ ID NO:3)

| Peptide Name | AA sequence | SEQ ID NO: |
|---|---|---|
| BfrB-1 | MTEYEGPKTK-FHALMQEQIH | 75 |
| BfrB-2 | FHALMQEQIH-NEFTAAQQYV | 76 |
| BfrB-3 | NEFTAAQQYV-AIAVYFDSED | 77 |
| BfrB-4 | AIAVYFDSED-LPQLAKHFYS | 78 |
| BfrB-5 | LPQLAKHFYS-QAVEERNHAM | 79 |
| BfrB-6 | QAVEERNHAM-MLVQHLLDRD | 80 |
| BfrB-7 | MLVQHLLDRD-LRVEIPGVDT | 81 |
| BfrB-8 | LRVEIPGVDT-VRNQFDRPRE | 82 |
| BfrB-9 | VRNQFDRPRE-ALALALDQER | 83 |
| BfrB-10 | ALALALDQER-TVTDQVGRLT | 84 |
| BfrB-11 | TVTDQVGRLT-AVARDEGDFL | 85 |
| BfrB-12 | AVARDEGDFL-GEQFMQWFLQ | 86 |
| BfrB-13 | GEQFMQWFLQ-EQIEEVALMA | 87 |
| BfrB-14 | EQIEEVALMA-TLVRVADRAG | 88 |
| BfrB-15 | TLVRVADRAG-ANLFELENFV | 89 |
| BfrB-16 | ANLFELENFV-AREVDVAPAA | 90 |
| BfrB-17 | AREVDVAPAA-SGAPHAAGGR | 91 |
| BfrB-18 | REVDVAPAAS-GAPHAAGGRL | 92 |

TABLE 4

Exemplary Peptides of TrxC (SEQ ID NO:4)

| Peptide Name | AA sequence | SEQ ID NO: |
|---|---|---|
| TrxC-1 | MTDSEKSATI-KVTDASFATD | 93 |
| TrxC-2 | KVTDASFATD-VLSSNKPVLV | 94 |
| TrxC-3 | VLSSNKPVLV-DFWATWCGPC | 95 |

TABLE 4-continued

Exemplary Peptides of TrxC (SEQ ID NO:4)

| Peptide Name | AA sequence | SEQ ID NO: |
|---|---|---|
| TrxC-4 | DFWATWCGPC-KMVAPVLEEI | 96 |
| TrxC-5 | KMVAPVLEEI-ATERATDLTV | 97 |
| TrxC-6 | ATERATDLTV-AKLDVDTNPE | 98 |
| TrxC-7 | AKLDVDTNPE-TARNFQWSI | 99 |
| TrxC-8 | TARNFQVVSI-PTLILFKDGQ | 100 |
| TrxC-9 | PTLILFKDGQ-PVKRIVGAKG | 101 |
| TrxC-10 | PVKRIVGAKG-KAALLRELSD | 102 |
| TrxC-11 | GAKGKAALLR-ELSDVVPNLN | 103 |

In general, preferred diagnostic epitopes and antigens are those recognized by antibodies (or by T cell, preferably Th1 cells) of "early" TB patients as defined above. This does not exclude the possibility that such epitopes are bound by antibodies or recognized by T cells present later in the infectious process. As noted herein, certain of the proteins/peptides are recognized by antibodies arising later in the infectious process, e.g., in cavitary TB, so that the antigens would not be considered "early antigens." In fact, seroreactivity with some of the proteins or peptides or epitopes thereof may detect infection in subjects whose infectious state is not detected by antibodies against the four novel early antigens or additional antigenic compositions disclosed herein.

Table5 below presents a list of additional Mtb protein antigens that have been discovered (either as part of this invention or earlier) to be early Mtb antigens. Thus, certain embodiments of the present invention include one or more of these proteins, or an-epitope-bearing peptide fragment thereof in a composition or method.

TABLE 5

Mtb Proteins Recognized as Antigens by Sera of Certain Infected Subjects

| H37Rv Gene Product | Common Protein Name (length - aa) | SEQ ID NO: | Amino Acid Sequence[a] |
|---|---|---|---|
| Rv0934 | PhoS1 PstS1 374 aa | 5 | VKIRLHTLLA VLTAAPLLLA AAGCGSKPPS GSPETGAGAG TVATTPASSP VTLAETGSTL LYPLFNLWGP AFHERYPNVT ITAQGTGSGA GIAQAAAGTV NIGASDAYLS EGDMAAHKGL MNIALAISAQ QVNYNLPGVS EHLKLNGKVL AAMYQGTIKT WDDPQIAALN PGVNLPGTAV VPLHRSDGSG DTFLFTQYLS KQDPEGWGKS PGFGTTVDFP AVPGALGENG NGGMVTGCAE TPGCVAYIGI SFLDQASQRG LGEAQLGNSS GNFLLPDAQS IQAAAAGFAS KTPANQAISM IDGPAPDGYP IINYEYAIVN NRQKDAATAQ TLQAFLHWAI TDGNKASFLD QVHFQPLPPA VVKLSDALIA TISS |
| Rv1860 | Apa/ModD MPT32 325 aa | 6 | MHQVDPNLTR RKGRLAALAI AAMASASLVT VAVPATANAD PEPAPPVPTT AASPPSTAAA PPAPATPVAP PPPAAANTPN AQPGDPNAAP PPADPNAPPP PVIAPNAPQP VRIDNPVGGF SFALPAGWVE SDAAHFDYGS ALLSKTTGDP PFPGQPPPVA NDTRIVLGRL DQKLYASAEA TDSKAAARLG SDMGEFYMPY PGTRINQETV SLDANGVSGS ASYYEVKFSD PSKPNGQIWT GVIGSPAANA PDAGPPQRWF VVWLGTANNP VDKGAAKALA ESIRPLVAPP PAPAPAPAEP APAPAPAGEV APTPTTPTPQ RTLPA |
| Rv3804c | FhpA Ag85A 338 aa | 7 | MQLVDRVRGA VTGMSRRLVV GAVGAALVSG LVGAVGGTAT AGAFSRPGLP VEYLQVPSPS MGRDIKVQFQ SGGANSPALY LLDGLRAQDD FSGWDINTPA FEWYDQSGLS VVMPVGGQSS FYSDWYQPAC GKAGCQTYKW ETFLTSELPG WLQANRHVKP TGSAVVGLSM AASSALTLAI YHPQQFVYAG AMSGLLDPSQ AMGPTLIGLA MGDAGGYKAS DMWGPKEDPA WQRNDPLLNV GKLIANNTRV WVYCGNGKPS DLGGNNLPAK FLEGFVRTSN IKFQDAYNAG GGHNGVFDFP DSGTHSWEYW GAQLNAMKPD LQRALGATPN TGPAPQGA |
| Rv1886c | FhpB Ag85B 325 aa | 8 | MTDVSRKIRA WGRRLMIGTA AAVVLPGLVG LAGGAATAGA FSRPGLPVEY LQVPSPSMGR DIKVQFQSGG NNSPAVYLLD GLRAQDDYNG WDINTPAFEW YYQSGLSIVM PVGGQSSFYS DWYSPACGKA GCQTYKWETF LTSELPQWLS ANRAVKPTGS AAIGLSMAGS SAMILAAYHP QQFIYAGSLS ALLDPSQGMG PSLIGLAMGD AGGYKAADMW GPSSDPAWER NDPTQQIPKL VANNTRLWVY CGNGTPNELG GANIPAEFLE NFVRSSNLKF QDAYNAAGGH NAVFNFPPNG THSWEYWGAQ LNAMKGDLQS SLGAG |
| Rv1837c | GlcB 741 aa | 9 | MTDRVSVGNL RIARVLYDFV NNEALPGTDI DPDSFWAGVD KVVADLTPQN QALLNARDEL QAQIDKWHRR RVIEPIDMDA YRQFLTEIGY LLPEPDDFTI TTSGVDAEIT TTAGPQLVVP VLNARFALNA ANARWGSLYD ALYGTDVIPE TDGAEKGPTY NKVRGDKVIA YARKFLDDSV PLSSGSFGDA TGFTVQDGQL VVALPDKSTG LANPGQFAGY TGAAESPTSV LLINHGLHIE ILIDPESQVG TTDRAGVKDV ILESAITTIM DFEDSVAAVD AADKVLGYRN WLGLNKGDLA AAVDKDGTAF LRVLNRDRNY TAPGGGQFTL PGRSLMFVRN VGHLMTNDAI VDTDGSEVFE GIMDALFTGL IAIHGLKASD VNGPLINSRT GSIYIVKPKM HGPAEVAFTC ELFSRVEDVL GLPQNTMKIG IMDEERRTTV NLKACIKAAA DRVVFINTGF LDRTGDEIHT SMEAGPMVRK GTMKSQPWIL AYEDHNVDAG LAAGFSGRAQ VGKGMWTMTE LMADMVETKI AQPRAGASTA WVPSPTAATL HALHYHQVDV AAVQQGLAGK RRATIEQLLT IPLAKELAWA PDEIREEVDN |

TABLE 5-continued

Mtb Proteins Recognized as Antigens by Sera of Certain Infected Subjects

| H37Rv Gene Product | Common Protein Name (length - aa) | SEQ ID NO: | Amino Acid Sequence[a] |
|---|---|---|---|
| | | | NCQSILGYVV RWVDQGVGCS KVPDIHDVAL MEDRATLRIS SQLLANWLRH GVITSADVRA SLERMAPLVD RQNAGDVAYR PMAPNFDDSI AFLAAQELIL SGAQQPNGYT EPILHRRRRE FKARAAEKPA PSDRAGDDAA R |
| Rv3881c | Hypothetical Ala/Gly-Rich protein 460 aa | 10 | MTQSQTVTVD QQEILNRANE VEAPMADPPT DVPITPCELT AAKNAAQQLV LSADNMREYL AAGAKERQRL ATSLRNAAKA YGEVDEEAAT ALDNDGEGTV QAESAGAVGG DSSAELTDTP RVATAGEPNF MDLKEAARKL ETGDQGASLA HFADGWNTFN LTLQGDVKRF RGFDNWEGDA ATACEASLDQ QRQWILHMAK LSAAMAKQAQ YVAQLHVWAR REHPTYEDIV GLERLYAENP SARDQILPVY AEYQQRSEKV LTEYNNKAAL EPVNPPKPPP AIKIDPPPPP QEQGLIPGFL MPPSDGSGVT PGTGMPAAPM VPPTGSPGGG LPADTAAQLT SAGREAAALS GDVAVKAASL GGGGGGGVPS APLGSAIGGA ESVRPAGAGD IAGLGQGRAG GGAALGGGGM GMPMGAAHQG QGGAKSKGSQ QEDEALYTED RAWTEAVIGN RRRQDSKESK |
| Rv0379 | SecE2 71 aa | 11 | MSVYKVIDII GTSPTSWEQA AAEAVQRARD SVDDIRVARV IEQDMAVDSA GKITYRIKLE VSFKMRPAQP R |
| Rv1980c | MPT64 228 aa | 12 | *VRIKIFMLVT AVVLLCCSGV ATA*APKTYCE ELKGTDTGQA CQIQMSDPAY NINISLPSYY PDQKSLENYI AQTRDKFLSA ATSSTPREAP YELNITSATY QSAIPPRGTQ AVVLKVYQNA GGTHPTTTYK AFDWDQAYRK PITYDTLWQA DTDPLPVVFP IVQGELSKQT GQQVSIAPNA GLDPVNYQNF AVTNDGVIFF FNPGELLPEA AGPTQVLVPR SAIDSMLA |
| Rv2031c | HspX 144 aa | 13 | MATTLPVQRH PRSLFPEFSE LFAAFPSFAG LRPTFDTRLM RLEDEMKEGR YEVRAELPGV DPDKDVDIMV RDGQLTIKAE RTEQKDFDGR SEFAYGSFVR TVSLPVGADE DDIKATYDKG ILTVSVAVSE GKPTEKHIQI RSTN |
| Rv3763 | LpqH 159 aa | 14 | *VKRGLTVAVA GAAILVAGLS*GCSSNKSTTG SGETTTAAGT TASPGAASGP KVVIDGKDQN VTGSVVCTTA AGNVNIAIGG AATGIAAVLT DGNPPEVKSV GLGNVNGVTL GYTSGTGQGN ASATKDGSHY KITGTATGVD MANPMSPVNK SFEIEVTCS |

[a]These sequences, obtained from Genflank which includes the fully sequenced Mtb genome. The sequence shown in this table is the complete protein sequence encoded by the open reading frame. Secreted proteins are synthesized with an N terminal secreted signal sequence ("SEC-dependent signal secretion sequence") which may include up to as many as 35 or 40 of the N-terminal residues. Signal sequences of several of the proteins are indicated in the table by underscore and italics. This sequenceis cleaved from the secreted protein. When used as immunogens, the secreted proteins lack this secreted signal sequence. Some of these sequences were obtained using MS or MS/MS data of peptides generated by trypsin digestion and were identified using the MSFit or Sequest programs, respectively.

Although only a subset of possible peptides of the four Mtb proteins antigens described herein are listed in Tables 1-4, the present invention is intended to include any peptide that comprises a B cell epitope that is recognized by an anti-Mtb antibody, such as an antibody in a TB patient, and preferably, an early antibody. One preferred type of peptide combines two of the "adjacent" 20-mers noted in Tables 1-4, while removing one "repeat" of the overlapping sequence. For clarification purposes but not limitation, an example of this approach follows:

Such a peptide combines SEQ ID NO: 75 and 76 of the BfrB protein:

SEQ ID NO:75    MTEYEGPKTK-FHALMQEQIH

SEQ ID NO:76    FHALMQEQIH-NEFTAAQQYV (the overlapping portion is underscored)

The new "combined" peptide is a 30 mer that combines the N-terminal half of SEQ ID NO:75 with the 10 residue sequence common to both, and the C-terminal half of SEQ ID NO:76, yielding:

MTEYEGPKTK-FHALMQEQIH-NEFTAAQQYV    (SEQ ID NO:104)

Such combining can be done along the entire length of the antigenic Mtb proteins and new 30 mer peptides created in this way. Such peptides may include the same epitope that was included in the two initial 20-mers, or may include an additional or different epitope that is useful for serodiagnosis, making the longer peptide useful as a composition and in the methods disclosed herein. Furthermore, there is no reason the combined peptide needs to be limited to 30 residues. If fact, it would require only routine testing to produce all possible peptides and polypeptides derived from the sequences of the proteins of the present invention that large are enough to be antigenic and assess them in studies using, for example, individual patient sera or serum pools (see Example VII).

Also included is an antigenic composition as above which is:

(a) A peptide multimer having the formula $P^1_n$ wherein $P^1$ is any Mtb antigenic peptides as described herein (or a conservative substitution variant thereof), and n=2-8. $P^1$ may represent different peptides, so that the multimer does not simply comprise repeats of the same peptide.

(b) A peptide multimer having the formula $$(P^1\text{-}X_m)_n\text{-}P^2$$

wherein $P^1$ and $P^2$ are any antigenic Mtb peptide as described herein (or conservative substitution variants thereof), and wherein (i) $P^1$ and $P^2$ may be the same or different and each occurrence of $P^1$ in the $P^1$-$X_m$ structure may be a different peptide (or variant) from its adjacent neighbor; and (ii) X is an organic linker, including an amino acid linker, for example:

$C_1$-$C_5$ alkyl, $C_1$-$C_5$ alkenyl, $C_1$-$C_5$ alkynyl, $C_1$-$C_5$ polyether containing up to 4 oxygen atoms, wherein m=0 or 1 and n=1-7; or and wherein the peptide multimer reacts with an antibody specific for the LppZ, SodC, BfrB or TrxC protein.

The invention is also directed to an antigenic composition as above which is a recombinant peptide multimer having the formula:

$$(P^1\text{-}Gly_z)_n\text{-}P^2$$

wherein $P^1$ and $P^2$ are any of the above peptides (or conservative substitution variants thereof), and wherein (a) $P^1$ and $P^2$ may be the same or different and each occurrence of $P^1$ in the $P^1$-$Gly_z$ structure may be a different peptide or variant from its adjacent neighbor;

(b) n=1-100 and z=0-6, and wherein the peptide multimer reacts with an antibody specific for the LppZ, SodC, BfrB or TrxC protein.

The preferred immunoassays of the present invention are enzyme immunoassays (EIA) such as ELISA, or dipstick-based immunoassays, both types of which are well-known in the art. An assay typically comprises incubating a biological fluid, preferably serum or urine, from a subject suspected of having TB, in the presence of an Mtb antigen-containing composition or reagent which includes one or more Mtb early antigens as described herein and detecting the binding of antibodies in the sample to the mycobacterial antigen(s). By the term "biological fluid" is intended any fluid derived from the body of a normal or diseased subject which may contain antibodies, such as blood, serum, plasma, lymph, urine, saliva, sputum, tears, cerebrospinal fluid, bronchioalveolar lavage fluid, pleural fluid, bile, ascites fluid, pus and the like. Also included within the meaning of this term as used herein is a tissue extract, or the culture fluid in which cells or tissue from the subject have been incubated.

In a preferred embodiment, the Mtb antigen composition is brought in contact with, and allowed to bind to, a solid support or carrier, such as nitrocellulose or polystyrene or any other of a myriad of solid supports known in the art (see below), allowing the antigens to adsorb and become immobilized to the solid support. This immobilized antigen is then allowed to interact with the biological fluid sample which is being tested for the presence of anti-Mtb antibodies, such that any antibodies in the sample will bind to the immobilized antigen. The support to which the antibody is now bound may then be washed with suitable buffers after which a detectably labeled binding partner for the antibody is introduced. The binding partner binds to the immobilized antibody. Detection of the label is a measure of the immobilized antibody.

A preferred binding partner for this assay is an anti-immunoglobulin antibody ("second antibody") produced in a different species. Thus to detect a human antibody, a detectably labeled goat anti-human immunoglobulin "second" antibody may be used. The solid phase support may then be washed with the buffer a second time to remove unbound antibody. The amount of bound label on the solid support may then be detected by conventional means appropriate to the type of label used (see below).

Such a "second antibody" may be specific for epitopes characteristic of a particular human immunoglobulin isotype, for example IgM, $IgG_1$, $IgG_{2a}$, IgA and the like, thus permitting identification of the isotype or isotypes of antibodies in the sample which are specific for the Mtb antigen. Alternatively, the second antibody may be specific for an idiotype of the ant-Mtb antibody of the sample.

As alternative binding partners for detection of the sample antibody, other known binding partners for human immunoglobulins may be used. Examples are the staphylococcal immunoglobulin binding proteins, the best know of which is protein A. Also intended is staphylococcal protein G, or a recombinant fusion protein between protein A and protein G. Protein G of group G and group C streptococci binds to the Fc portion of Ig molecules as well as to IgG Fab fragment at the $V_H3$ domain. Protein C of *Peptococcus magnus* binds to the Fab region of the immunoglobulin molecule. Any other microbial immunoglobulin binding proteins, for example from Streptococci, are also intended (for example, Langone, J. J., *Adv. Immunol* 32:157 (1982)).

In another embodiment of this invention, a biological fluid suspected of containing antibodies specific for a Mtb antigen may be brought into contact with a solid support or carrier which is capable of immobilizing soluble proteins. The support may then be washed with suitable buffers followed by treatment with a Mtb antigen reagent, which may be detectably labeled. Bound antigen is then measured by measuring the immobilized detectable label. If the Mtb antigen reagent is not directly detectably labeled, a second reagent comprising a detectably labeled binding partner for the Mtb antigen, generally a second anti-Mtb antibody such as a murine mAb, is allowed to bind to any immobilized antigen. The solid phase support may then be washed with buffer a second time to remove unbound antibody. The amount of bound label on said solid support may then be detected by conventional means.

By "solid phase support" or carrier is intended any support capable of binding a proteinaceous antigen or antibody molecules or other binding partners according to the present invention. Well-known supports, or carriers, include glass, polystyrene, polypropylene, polyethylene, polyvinylidene difluoride, dextran, nylon, magnetic beads, amylases, natural and modified celluloses, polyacrylamides, agaroses, and magnetite. The nature of the carrier can be either soluble to some extent or insoluble for the purposes of the present invention. The support material may have virtually any possible structural configuration so long as it is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads, 96-well polystyrene microplates and test strips, all well-known in the art. Those skilled in the art will know many other suitable carriers for binding antibody or antigen, or will be able to ascertain the same by use of routine experimentation.

Using any of the assays described herein, those skilled in the art will be able to determine operative and optimal assay conditions for each determination by employing routine experimentation. Furthermore, other steps as washing, stirring, shaking, filtering and the like may be added to the assays as is customary or necessary for the particular situation.

As noted, a preferred type of immunoassay to detect an antibody specific for a Mtb antigen according to the present invention is an enzyme-linked immunosorbent assay (ELISA) or more generically termed an enzyme immunoassay (EIA). In such assays, a detectable label bound to either an antibody-binding or antigen-binding reagent is an enzyme. When exposed to its substrate, this enzyme will react in such a manner as to produce a chemical moiety which can be detected, for example, by spectrophotometric, fluorometric or visual means. Enzymes which can be used to detectably label the reagents useful in the present invention include, but are not limited to, horseradish peroxidase, alkaline phosphatase, glucose oxidase, β-galactosidase, ribonuclease, urease, catalase, malate dehydrogenase, staphylococcal nuclease, asparaginase, Δ-5-steroid isomerase, yeast alcohol dehydrogenase, α-glycerophosphate dehydrogenase, triose phosphate isomerase, glucose-6-phosphate dehydrogenase, glucoamylase and acetylcholinesterase. For descriptions of EIA procedures, see reference cited above or, additionally, Voller, A. et al., J. Clin. Pathol. 31:507-520 (1978); Butler, J. E., Meth. Enzymol. 73:482-523 (1981); Maggio, E. (ed.), *Enzyme Immunoassay*, CRC Press, Boca Raton, 1980.

In another embodiment, the detectable label may be a radiolabel, and the assay termed a radioimmunoassay (RIA), as is well known in the art. The radioisotope can be detected by a gamma counter, a scintillation counter or by autoradiography. Isotopes which are particularly useful for the purpose of the present invention are $^{125}I$, $^{131}I$, $^{35}S$, $^{3}H$ and $^{14}C$.

It is also possible to label the antigen or antibody reagents with a fluorophore. When the fluorescently labeled antibody is exposed to light of the proper wave length, its presence can then be detected due to fluorescence of the fluorophore. Among the most commonly used fluorophores are fluorescein isothiocyanate, rhodamine, phycoerythrin, phycocyanin, allophycocyanin, o-phthaldehyde, fluorescamine or fluorescence-emitting metals such as $^{152}Eu$ or other lanthanides. These metals are attached to antibodies using metal chelators.

The antigen or antibody reagents useful in the present invention also can be detectably labeled by coupling to a chemiluminescent compound. The presence of a chemiluminescent-tagged antibody or antigen is then determined by detecting the luminescence that arises during the course of a chemical reaction. Examples of useful chemiluminescent labeling compounds are luminol, isoluminol, theromatic acridinium ester, imidazole, acridinium salt and oxalate ester. Likewise, a bioluminescent compound such as a bioluminescent protein may be used to label the antigen or antibody reagent useful in the present invention. Binding is measured by detecting the luminescence. Useful bioluminescent compounds include luciferin, luciferase and aequorin.

Detection of the detectably labeled reagent according to the present invention may be accomplished by a scintillation counter, for example, if the detectable label is a radioactive gamma emitter, or by a fluorometer, for example, if the label is a fluorophore. In the case of an enzyme label, the detection is accomplished by colorimetry to measure the colored product produced by conversion of a chromogenic substrate by the enzyme. Detection may also be accomplished by visual comparison of the colored product of the enzymatic reaction in comparison with appropriate standards or controls.

The immunoassay of this invention may be a "two-site" or "sandwich" assay. The fluid containing the antibody being assayed is allowed to contact a solid support. After addition of the Mtb antigen(s), a quantity of detectably labeled soluble antibody is added to permit detection and/or quantitation of the ternary complex formed between solid-phase antibody, antigen, and labeled antibody. Sandwich assays are described by Wide, *Radioimmune Assay Method*, Kirkham et al, Eds., E. & S. Livingstone, Edinburgh, 1970, pp 199-206.

Alternatives assays are various types of agglutination assays, both direct and indirect, which are well known in the art. In these assays, the agglutination of particles containing the antigen (either naturally or by chemical coupling) indicates the presence or absence of the corresponding antibody. Any of a variety of particles, including latex, charcoal, kaolinite, or bentonite, as well as microbial cells or red blood cells, may be used as agglutinable carriers (Mochida, U.S. Pat. No. 4,308,026; Gupta et al, *J. Immunol. Meth.* 80:177-187 (1985); Castelan et al., *J. Clin. Pathol.* 21:638 (1968); Molinaro, U.S. Pat. No. 4,130,634). Traditional particle agglutination or hemagglutination assays are generally faster, but much less sensitive than RIA or EIA. However, agglutination assays have advantages under field conditions and in less developed countries.

In addition to detection of antibodies, the present invention provides methods to detect and enumerate cells secreting an antibody specific for a Mtb antigen. Thus, for example, any of a number of plaque or spot assays may be used wherein a sample containing lymphocytes, such as peripheral blood lymphocytes, is mixed with a reagent containing the antigen of interest. As the antibody secreting cells of the sample secrete their antibodies, the antibodies react with the antigen, and the reaction is visualized in such a way that the number of antibody secreting cells (or plaque forming cells) may be determined. The antigen may be coupled to indicator particles, such as erythrocytes, preferably sheep erythrocytes, arranged in a layer. As antibodies are secreted from a single cell, they attach to the surrounding antigen-bearing erythrocytes. By adding complement components, lysis of the erythrocytes to which the antibodies have attached is achieved, resulting in a "hole" or "plaque" in the erythrocyte layer. Each plaque corresponds to a single antibody-secreting cell. In a different embodiment, the sample containing antibody-secreting cells is added to a surface coated with an antigen-bearing reagent, for example, a Mtb antigen alone or conjugated to bovine serum albumin, attached to polystyrene. After the cells are allowed to secrete the antibody which binds to the immobilized antigen, the cells are gently washed away. The presence of a colored "spot" of bound antibody, surrounding the site where the cell had been, can be revealed using modified EIA or other staining methods well-known in the art. (See, for example, Sedgwick, J. D. et al., *J. Immunol. Meth.* 57:301-309 (1983); Czerkinsky, C. C. et al., *J. Immunol. Meth.* 65:109-121 (1983); Logtenberg, T. et al., *Immunol. Lett.* 9:343-347 (1985); Walker, A. G. et al., *J. Immunol. Meth.* 104:281-283 (1987).

The present invention is also directed to a kit or reagent system useful for practicing the methods described herein. Such a kit will contain a reagent combination comprising the essential elements required to conduct an assay according to the disclosed methods. The reagent system is presented in a commercially packaged form, as a composition or admixture (where the compatibility of the reagents allow), in a test device configuration, or more typically as a test kit. A test kit is a packaged combination of one or more containers, devices, or the like holding the necessary reagents, and usually including written instructions for the performance of assays. The kit may include containers to hold the materials during storage, use or both. The kit of the present invention may include any configurations and compositions for performing the various assay formats described herein.

For example, a kit for determining the presence of anti-Mtb early antibodies or antibodies to early or even later stage Mtb antigens may contain one or more of the proteins disclosed herein or another early Mtb antigen either in immobilizable form or already immobilized to a solid support, and a detectably labeled binding partner capable of recognizing the sample anti-Mtb antibody to be detected, for example. a labeled anti-human Ig or anti-human Fab antibody. A kit for determining the presence of an Mtb antigen may contain an immobilizable or immobilized "capture" antibody which reacts with one epitope of the target Mtb antigen, and a detectably labeled second ("detection") antibody which reacts with a different epitope of the Mtb antigen than that recognized by the (capture) antibody. Any conventional tag or detectable label may be part of the kit, such as a radioisotope, an enzyme, a chromophore or a fluorophore. The kit may also contain a reagent capable of precipitating immune complexes.

A kit according to the present invention can additionally include ancillary chemicals such as the buffers and components of the solution in which binding of antigen and antibody takes place.

The present invention permits isolation of an Mtb early antigen which is then used to produce one or more epitope-specific mAbs, preferably in mice. Screening of these putative early Mtb-specific mAbs is done using known patient sera which have been characterized for their reactivity with the early antigen of interest. The murine mAbs produced in this way are then employed in a highly sensitive epitope-specific competition immunoassay for early detection of TB. Thus, a patient sample is tested for the presence of antibody specific for an early epitope of Mtb by its ability to compete with a known mAb for binding to a purified early antigen. For such an assay, the Mtb preparation may be less than pure because, under the competitive assay conditions, the mAb provides the requisite specificity for detection of patient antibodies to the epitope of choice (for which the mAb is specific).

In addition to the detection of early Mtb antigens or early antibodies, the present invention provides a method to detect immune complexes containing early Mtb antigens in a subject using an EIA as described above. Circulating immune complexes have been suggested to be of diagnostic value in TB. (See, for example, Mehta, P. K. et al, 1989, *Med. Microbiol. Immunol.* 178:229-233; Radhakrishnan, V. V. et al., 1992, *J. Med. Microbiol.* 36:128-131). Methods for detection of immune complexes are well-known in the art. Complexes may be dissociated under acid conditions and the resultant antigens and antibodies detected by immunoassay. See, for example, Bollinger, R. C. et al, 1992, *J. Infec. Dis.* 165:913-916. Immune complexes may be precipitated for direct analysis or for dissociation using known methods such as polyethylene glycol precipitation.

Purified Mtb early antigens as described herein are preferably produced using recombinant methods. See the Examples. Conventional bacterial expression systems include Gram negative bacteria such as *E. coli* or *Salmonella* species. However, such systems are not believed to be ideally suited for production of Mtb antigens (Burlein, J E, In: *Tuberculosis: Pathogenesis, Protection and Control*, B. Bloom, ed., Amer. Soc. Microbiol., Washington, D.C., 1994, pp. 239-252). Rather, it is preferred to utilize homologous mycobacterial hosts for recombinant production of early Mtb antigenic proteins or glycoproteins. Methods for such manipulation and gene expression are provided in Burlein, supra. Expression in mycobacterial hosts, in particular *M. bovis* (strain BCG) or *M. smegmatis* are well-known in the art. Two examples, one of mycobacterial genes (Rouse, D A et al., 1996, *Mol. Microbiol.* 22:583-592) and the other of non mycobacterial genes, such as HIV-1 genes (Winter, N et al., 1992, Vaccines 92, Cold Spring Harbor Press, pp. 373-378) expressed in mycobacterial hosts are examples.

Urine-Based Antibody Assay

The present invention also provides a urine based diagnostic method for TB that can be used either as a stand-alone test, or as an adjunct to the serodiagnostic methods described herein. Such a method enables the practitioner to (1) determine the presence of anti-Mtb antibodies in urine from TB patients with early disease (non-cavitary, smear negative TB patients) and from HIV-infected TB patients; (2) determine the profile of specific Mtb antigens, such as those in the culture filtrate, that are consistently and strongly reactive with the urine antibodies; and (3) obtain the antigens that are recognized by the urine antibodies.

Smear positive (=late) cases constitute only about 50% of the TB cases, and patients with relatively early disease are generally defined as being smear negative. Moreover, as the HIV-epidemic spreads in developing countries, the numbers and proportions of HIV-infected TB patients increases.

Serum and urine samples from non-cavitary and/or smear negative, culture positive TB patients and from HIV-infected TB patients are obtained Cohorts comprising PPD-positive and PPD-negative healthy individuals, non-tuberculous HIV-infected individuals, or close contacts of TB patients can serve as negative controls.

The reactivity of the serum samples with culture filtrate proteins of Mtb, and the purified antigens (as described herein) is preferably determined by ELISA as described herein. All sera are preferably depleted of cross-reactive antibodies prior to use in ELISA.

The following description is of a preferred assay method and approach, and is not intended to be limiting to the particular steps (or their sequence), conditions, reagents and amounts of materials.

Briefly, 200 µl of *E. coli* lysates (suspended at 500 µg/ml) are coated onto wells of ELISA plates (Immulon 2, Dynex, Chantilly, Va.) and the wells are blocked with 5% bovine serum albumin (BSA). The serum samples (diluted 1:10 in PBS-Tween-20) are exposed to 8 cycles of absorption against the *E. coli* lysates. The adsorbed sera are then used in the ELISA assays.

Fifty µl of the individual antigens, suspended at 2 µg/ml in coating buffer (except for the total culture filtrate proteins which is used at 5 µg/ml), are allowed to bind overnight to wells of ELISA plates. After 3 washes with PBS (phosphate buffered saline), the wells are blocked with 7.5% FBS (fetal bovine serum, Hyclone, Logan, Utah.) and 2.5% BSA in PBS for 2.5 hr at 37° C. Fifty µl of each serum sample are added per well at predetermined optimal dilutions (e.g., dilutions of about 1:50-1:200). The antigen-antibody binding is allowed to proceed for 90 min at 37° C. The plates are washed 6 times with PBS-Tween 20 (0.05%) and 50 µl/well of alkaline phosphatase-conjugated goat anti-human IgG (Zymed, Calif.), diluted 1:2000 in PBS/Tween 20 is added. After 60 min the plates are washed 6 times with Tris buffered saline (50 mM Tris, 150 mM NaCl) and the Gibco BRL Amplification System (Life Technologies, Gaithersburg, Md.) used for development of color. The absorbance is read at 490 nm after stopping the reaction with 50 µl of 0.3M $H_2SO_4$. The cutoff in all ELISA assays is determined by using mean absorbance (=Optical Density O.D.)+3 standard deviations (SD) of the negative control group comprising PPD positive and PPD negative healthy individuals.

The reactivity of the urine samples with the various antigens is determined initially with undiluted urine samples as described above. For the urine ELISA, results obtained by the present inventors showed that the optimal concentration of the culture filtrate protein preparation is about 125 µl/well of 4 µg/ml suspension, and for certain proteins, 125 µl/well of about 2 µg/ml. Also, the urine is left overnight in the antigen coated wells. However, if urine antibody titers of smear-negative and HIV-infected patients are lower than those observed in smear positive patients, it may be necessary to first concentrate the urine samples. For concentration, Amicon concentrators with a molecular weight cut off of 30 kDa is preferred. Concentrated urine samples are evaluated for the presence of antibodies to the above mentioned antigens. Optimal conditions for these assays are determined readily. The sensitivity and specificity of antibody detection by use of one or more of the antigens, with both urine and serum samples is also readily determined.

Having now generally described the invention, the same will be more readily understood through reference to the following examples which are provided by way of illustration, and are not intended to be limiting of the present invention, unless specified.

Example I

Experimental Procedures

Preparation of Mtb Subcellular Fractions

Mtb strain H37Rv was expanded from a 1-ml frozen stock (approximately $10^8$ colony-forming units per ml) to 24 L of late log culture in glycerol-alanine salts medium (17). The culture supernatant was separated from the cells and processed to generate the CFPs of Mtb as previously described (18). The Mtb H37Rv cells (88.9 g wet weight) were washed 3 times with PBS (pH 7.4), frozen at −70° C. and inactivated with 24 kGy of γ-irradiation. Lysis of these cells was achieved by suspending in 44 ml of TSE buffer [10 mM Tris-HCl (pH 7.4), 150 mM NaCl, 1 mM EDTA] containing 0.06% DNase, 0.06% RNase, 0.07% pepstatin, 0.05% leupeptin and 20 µM PMSF and passing through a French Press five times at 1,500 psi. The resulting lysate was diluted with 1 vol of TSE buffer and centrifuged at 2,000×g for 5 min to remove unbroken cells. The cytosol was obtained as the final supernatant of sequential centrifugations at 27,000×g and 100,000×g (19), and was dialyzed against 10 mM ammonium bicarbonate using a 3,500 Da molecular weight cut-off membrane. The protein concentrations of the cytosol and CFP were determined with the bicinchoninic acid (BCA) protein assay (20).

Multi-Dimensional Protein Fractionation

Initial fractionation of the CFP (124 ml at 3.6 mg/ml) and cytosolic proteins (200 ml at 2.5 mg/ml) was achieved with sequential rounds of ammonium sulfate precipitation. Specifically, the CFP and cytosolic proteins were precipitated with 42% and 67%; and 29% and 44% saturated ammonium sulfate, respectively. Precipitated proteins were collected by centrifugation at 10,000×g, 4° C. for 1 hr. All protein pellets were suspended in 20 mM Tris-HCl (pH 8.0). These suspensions and the final supernatants of the sequential precipitations were dialyzed against 20 mM Tris-HCl (pH 8.0), using a 3,500 Da molecular weight cutoff membrane, and the dialyzed protein solutions were concentrated where needed. To ensure the removal of contaminating nucleic acids, $MgCl_2$ (5 mM final conc.) and DNase and RNase (1.25% final conc.) were added to each fraction followed by incubation at 37° C. for 30 min.

The fractions obtained by ammonium sulfate precipitation were adjusted to 10% acetonitrile, and applied to a high-pressure liquid chromatography (HPLC) column (1×10 cm) packed with Source 15Q strong anion-exchange (AIEX) resin (Amersham Biosciences, Piscataway, N.J.). Proteins were eluted with a step gradient of increasing concentrations of NaCl at a flow rate of 3.3 ml per min using a Waters 600E HPLC system (Waters Corp., Milford, Mass.). The eluted protein fractions were concentrated 100-fold, and exchanged into 20 mM ammonium bicarbonate by ultrafiltration. Protein concentrations were determined by the BCA assay, and fractions containing less than 1 mg protein were pooled. All other fractions were kept separate. The concentrated AIEX fractions were adjusted to 10% acetonitrile, applied to a HPLC Source™ 15RPC ST 4.6/100 column (Amersham) and the proteins eluted with an increasing linear gradient (10% to 70%) of acetonitrile. All fractions were dried in a speed-vac, suspended in 67 µl of 10 mM ammonium bicarbonate, and protein concentrations determined by the BCA assay.

Human Sera and Antibodies

Sera from the following groups of individuals were obtained with informed consent.

(i) Twelve PPD-positive healthy individuals. Seven of these individuals were recent immigrants from countries where Mtb is endemic, many of whom had been vaccinated with *Mycobacterium bovis* BCG; the remaining five individuals were from the United States or western Europe and were not BCG-vaccinated.

(ii) Nine noncavitay-TB patients with no recognizable cavitary lesions on chest X rays. These were acid-fast bacilli (AFB) sputum-smear-negative (6/9) or positive (3/9), culture positive patients attending the infectious disease clinic at the Manhattan Va. medical center. None of these patients were HIV-infected. These individuals were bled either prior to or within two weeks of the initiation of therapy for TB.

(iii) Eleven cavitary-TB patients, with moderate-to-advanced cavitary lesions as determined by chest X rays. These were sputum smear AFB positive patients obtained from the Lala Ram Sarup Institute in New Delhi, India who were all bled prior to initiation of therapy for TB. None of these patients were HIV infected.

(iv) Ten HIV-positive TB patients. These were sputum smear positive (7/10) or negative (3/10), culture-confirmed patients from the Manhattan Va. None of the patients had radiological evidence of cavitary lesions. All ten patients were known to possess antibodies to the CFP of Mtb when tested by ELISA in earlier studies (3, 6). These patients were bled either prior to or within two weeks of the initiation of therapy for TB.

(v) Six HIV-positive TB-negative patients. These were asymptomatic, HIV-infected individuals from the Manhattan Va. All sera were preadsorbed with *Escherichia coli* lysates to remove cross-reactive antibodies to ubiquitous prokaryotic proteins as described earlier (4).

Monoclonal antibodies (mAbs) and polyclonal sera against specific Mtb proteins were obtained from the Colorado State University TB Research Materials and Vaccine Testing Contract (NIH, NIAID NO1-AI-75320). The following antibodies and dilutions were used for both microarray analyses and immunoblots: IT-12 α-19 kDa (1:20), IT-20 α-HspX (1:100), IT-23 α-PstS1 (1:20), IT-47 α-PstS1 (1:20), IT-52 α-MPT51 (1:5), CS-35 α-LAM (1:20), CS-49 α-HspX (1:100), CS-93 α-45 kDa (1:20), and α-45 kDa polyclonal sera (1:1000).

Protein Microarray Printing and Probing

An aliquot (5 µg protein) of each multi-dimensional chromatography fraction was transferred to 384-well microtiter plates, dried, and solubilized in 25 µl FAST® protein array print buffer (Schleicher & Schuell Bioscience, Keene, N.H.). The plates were centrifuged briefly (2,000×g) to pellet any precipitate, and ~1 nl of the supernatants (0.2 mg per ml) was printed to nitrocellulose-coated FAST® glass slides (Schleicher & Schuell) using Stealth SMP3® spotting pins (TeleChem International, Sunnyvale, Calif., www.arrayit.com) and a VersaArray® Chipwriter Pro microarray contact printer (Bio-Rad Laboratories, Hercules, Calif.). Cytosolic proteins, CFP, the native 38-kDa PstS1 protein (Rv0934), and the six ammonium sulfate precipitation fractions were also printed in a dilution series of 1.6, 0.8, 0.4, 0.2, 0.1, 0.5, 0.25, and 0.125 mg/ml. As negative controls, E. coli whole-cell lysate WCL was printed in the same dilution series, and FAST® print buffer was printed alone. All samples were printed in triplicate, resulting in 3,768 total spots per slide. The slides were allowed to dry 1 hour at room temperature (RT) and stored at 4° C. until use. Printed microarray slides were washed 10 min commercial FAST® protein array wash buffer (Schleicher & Schuell), and probed with individual serum (750 µl) diluted 1:100 in PBS (pH 7.4), 1% BSA for 1 h at RT. Slides were washed twice for 10 min in FAST® protein array wash buffer and probed for 1 h at RT with Cy3-conjugated anti-human IgG (Sigma, St. Louis, Mo.) diluted 1:500 in FAST® protein array wash buffer. Slides were again washed twice for 10 min, allowed to dry, and scanned using a VersArray® Chipreader (Bio-Rad Laboratories, Hercules, Calif.). Probing of the microarray slides with MAbs or polyclonal sera was performed in the same manner, except Cy3 conjugated anti-mouse IgG or Cy5 conjugated anti-rabbit IgG (Amersham Biosciences) were used, respectively, as the secondary antibody. Microarray analyses of individual patient's serum were repeated in triplicate, and one slide was used for each MAb or rabbit polyclonal sera.

Microarray Data Analyses

Microarray spot intensity values were quantified with TIGR Spotfinder software (21). Signal-to-Noise Ratios (SNRs) were calculated for each spot by dividing the raw intensity (sum of all pixels per spot) by the background intensity (local background median multiplied by spot area). Analysis of SNR reduced the local background variation or bias observed between individual slides. The mean SNR for each protein or protein fraction printed in triplicate was determined, resulting in an averaged SNR (AvSNR). To allow for direct patient-to-patient or slide-to-slide comparisons, all AvSNRs for a slide were normalized against the median AvSNR of all multidimensional chromatography fractions of the slide. The normalized AvSNR(NAvSNR) was based on the median AvSNR rather than the mean AvSNR since the median AvSNR was less affected by variations in reactivity between sera. For the microarray slides probed with MAbs or rabbit polyclonal sera, the AvSNR for each fraction was calculated.

SDS-PAGE and Western Blot Analyses

SDS-PAGE of multidimensional chromatography fractions was performed with 10% to 20% polyacrylamide gradient Tricine gels (Invitrogen, Carlsbad, Calif.) or 15% Trisglycine gels (10 cm×7.5 cm) (22). Protein staining was achieved with silver nitrate (23) or Coomassie Brilliant Blue R-250. For Western blot analyses, aliquots (3 µg) of selected fractions were resolved on 10% to 20% polyacrylamide gradient Tricine gels and electroblotted to nitrocellulose membranes (17). The membranes were blocked with 3% nonfat milk in PBS (pH 7.2) for 2 h, washed with PBS containing 2% Tween 20, and exposed overnight to preabsorbed pooled sera from patients and control subjects diluted 1:200. The blots were washed with PBS containing 2% Tween 20, probed with alkaline phosphatase-conjugated anti-human IgG (1:2000, Sigma) for 1.5 h, and washed extensively. Antigen-antibody complexes were visualized by color development with 5-bromo-4-chloro-indoyl-phosphatase-nitroblue tetrazolium substrate (Kirkegaard & Perry Laboratories, Gaithersburg, Md.).

Mass Spectrometry

Coomassie stained protein bands corresponding to those that reacted to patients' sera on Western blots were excised, subjected to in-gel digestion with modified Trypsin (Roche Applied Science, Indianapolis, Ind.), and the resulting peptides were extracted with 60% acetonitrile, 0.1% TFA (24). Extracted peptides were applied to a capillary (0.2×50 mm) C18 reversed phase (RP) column (from Microchom BioResources, Auburn, Calif.) and eluted with an increasing linear gradient (5% to 70%) of acetonitrile in 0.1% acetic acid using an Eldex MicroPro capillary HPLC system (Napa, Calif.) with a flow rate of 5 µl per min. The RP eluant was introduced directly into a ThermoFinnigan LCQ electrospray mass spectrometer (San Jose, Calif.) operated using Xcalibur software version 1.3, and the peptides were analyzed by tandem mass spectrometry (MS/MS). The electrospray needle was set at 4 kV with a $N_2$ sheath gas flow of 40, and a capillary temperature of 200° C. MS/MS was automatically performed on the most dominant ion of the previous scan and the normalized collision energy was set at 40%. BioWorks 3.1 turboSEQUEST software (ThermoFinnigan) was used to match the MS/MS data of peptides to protein sequences extracted form the Mtb genome database (NC_000962) that contained 3989 proteins. The software was set to evaluate peptides obtained by trypsin or chymotrypsin and GluC digestion and to consider the oxidation of methionine (+16.0 amu) and the acrylamide modification of cysteine (+71.0 amu). The Scaffold software (Proteome Software, Portland, Oreg.) that verifies peptide identifications made by SEQUEST and probabilistically validates the peptide and protein identifications was applied to all MS/MS sequencing results.

Example II

Multi-Dimensional Protein Fractionation Reduced the Complexity of Mycobacterial Protein Pools Recent advances in proteomics have enabled the separation and identification of individual proteins or peptides from complex biological samples. Specifically, multi-dimensional chromatography of peptides, derived from tryptic digests of crude biological samples, followed by MS/MS analysis ("MudPIT") has provided experimental validation of substantial portions of theoretical proteomes (25). Recently, this approach was applied to Mtb and resulted in more than a threefold increase in the number of proteins that had previously been identified by 2-D gel electrophoresis methods (26).

Applying a similar strategy, the present study employed a multi-dimensional fractionation scheme (FIG. 6) for efficient separation of complex pools of intact Mtb proteins into relatively simple and enriched fractions that could be evaluated for serological reactivity in a high-throughput fashion.

Aliquots of CytPs (500 mg) and CFPs (446 mg) from Mtb H37Rv were subjected to sequential ammonium sulfate precipitations, resulting in six fractions with nearly equal protein amounts (FIG. 1A). Subsequent AIEX chromatography expanded the fraction number to 78, with protein yields varying from 160 µg to 13 mg per fraction (FIG. 1B). Those fractions (eight) containing 500 μg of protein were excluded from further separation, and fractions containing between 500 μg and 1 mg were pooled with neighboring fractions (a total of 10 such fractions). This resulted in a total of 64 fractions that were subjected to RP chromatography under mildly basic pH conditions. This multidimensional chromatographic separation yielded a total of 960 fractions, and SDS-PAGE analysis revealed varied complexity among the fractions, with between 1 and >20 proteins per fraction (FIG. 1C).

Example III

Validation of the Protein Microarray Format

Each multidimensional chromatography fraction, as well as intermediate fractions and recombinant proteins were printed to nitrocellulose microarray slides. Serum samples from PPD$^+$ healthy subjects (n=12), noncavitary-TB subjects (n=9), cavitary-TB subjects (n=11), and HIV$^+$TB$^+$ (n=10) subjects were probed against the microarrays in triplicate. For each slide the NAvSNR (see Example I) was calculated for each protein or protein fraction. The integrity of the protein microarray and validation of this platform was determined by assessing the reactivity of TB patients' sera with selected protein fractions and with purified proteins that were spotted on the microarray slides as controls, and comparing these results to published results obtained by plate ELISA (5, 6).

Figure 2:
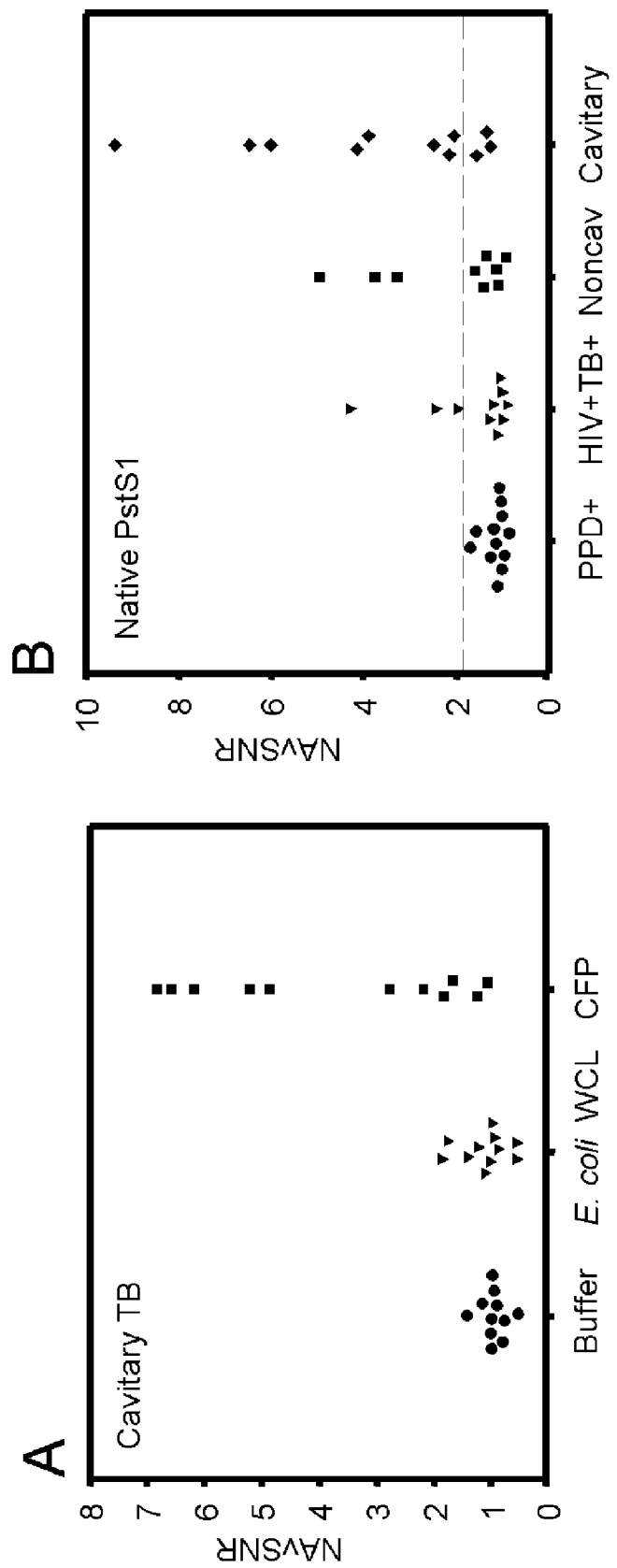
FIG. 2. Validation of protein microarray integrity. (A) Reactivity of cavitary-TB patients' sera against buffer (●), *E. coli* WCL (∇), and Mtb CFP (■). (B) Reactivity of PPD$^+$ healthy controls (●), HIV$^+$TB$^+$ (∇), noncavitary-TB (■), and cavitary-TB (♦) patients' sera against spotted native, purified 38-kDa PstS1. The patient-averaged NAvSNR +3 SD was obtained by use of sera from healthy PPD$^+$ control subjects, shown as the horizontal dashed line, and was used as the cutoff to determine positive reactivity.

To demonstrate specificity, the reactivity of TB patients' serum samples towards unfractionated CFP was compared to reactivity towards either E. coli WCL control or FAST® print buffer control. The CFP is known to contain numerous B cell antigens (2), and as expected, sera from cavitary-TB patients displayed significantly greater reactivity to CFP than to either the control buffer (p=0.001) or to E. coli WCL (p=0.002) (FIG. 2A). Although patient-to-patient variability in reactivity to unfractionated CFP was observed, each individual cavitary-TB patient's serum recognized CFP more strongly than it did buffer alone or E. coli WCL.

A second validation control was performed with the purified native 38-kDa protein known as PstS1/Rv0934, previously characterized as a B cell antigen (2). Reactivity to PstS1 was compared among the four patient groups used in this study (FIG. 2B). Serum samples from TB patients showed greater reactivity than did serum samples from PPD$^+$ healthy individuals. Furthermore, when evaluated using the mean NAvSNR of PPD$^+$ healthy controls +3SD as a cutoff, the number of patients' sera demonstrating a positive response to PstS1 was greatest in cavitary-TB (72%), followed by noncavitary-TB (33%), and HIV$^+$TB$^+$ (30%). These results were in agreement with results data previously obtained using traditional ELISA assays (5, 6). The PstS1 protein was also printed at multiple concentrations, and the antibody reactivity showed dose-dependence (not shown).

Example IV

Sera from Different TB Disease Categories React with Defined Groups of Antigens

Figure 3:
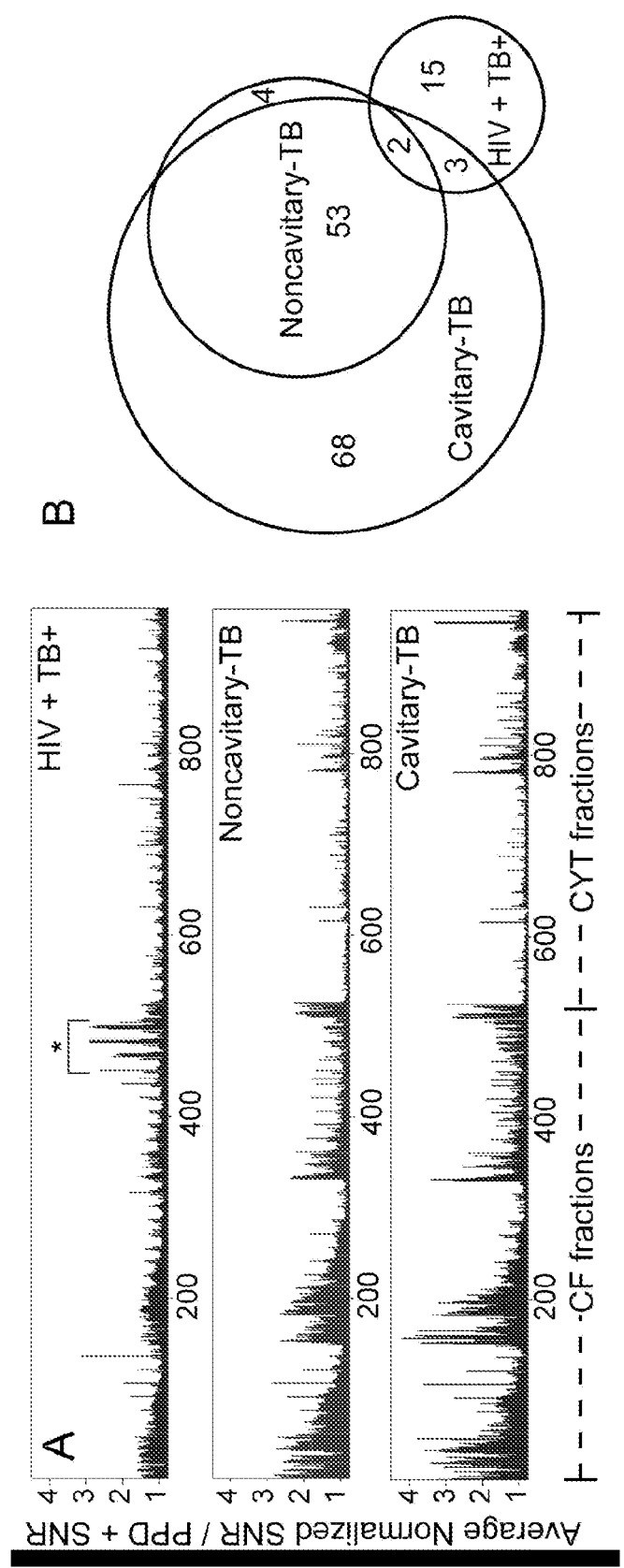
FIG. 3. Global Analysis of HIV$^+$TB$^+$, noncavitary-TB, and cavitary-TB patient reactivity against all 960 protein fractions. (A) Each fraction's NAvSNR was averaged for all patients in each disease category, and expressed as a ratio over the corresponding fraction's averaged healthy PPD$^+$ NAvSNR. Culture filtrate fractions (1-525), cytosolic fractions (526-960) (B) A Venn diagram displaying the number of fractions with significant reactivity to sera from each disease category and the relatedness of these serological responses. The fractions included in the Venn diagram were recognized by ≧40% of patients.

To evaluate patterns of serological reactivity, the NAvSNR values of each fraction were averaged for all patients within a disease category, and expressed as a ratio to the corresponding fraction's averaged PPD$^+$ healthy control NAvSNR values (FIG. 3A). In other words, the ratios expressed were:

Patient NAvSNR value/Healthy control NAvSNR value.

Fractions originating from the culture filtrate (fractions 1-525) were more antigenic overall than those derived from the cytosol (fractions 526-960). Additionally, differences in reactivity according to disease category were also observed. This was most pronounced when comparing HIV$^+$TB$^+$ patients to cavitary- or noncavitary-TB patients (who did not have evidence of HIV infections). The HIV$^+$TB$^+$ sera generally displayed very weak reactivity, except for a distinct cluster of CFP fractions with which sera from other disease categories did not react well (FIG. 3A).

To simplify patterns of antigen reactivity and to further assess similarities and differences in antigen recognition between disease categories, a cutoff value of the mean NAvSNR of PPD$^+$ healthy controls +3SD was established for each fraction. Fractions displaying NAvSNR values greater than this cutoff value in 40% or more of the individuals in a disease category were selected and the numbers of such sera were organized as a Venn diagram (FIG. 3B). Using these criteria, 145 of the 960 fractions (15%) were identified as having significant serological reactivity. As shown in FIG. 3B, serum samples from cavitary-TB patients recognized 126 fractions, while those from noncavitary-TB patients showed significant reactivity to 59 fractions, of which 55 fractions were also recognized by cavitary-TB patient samples. The remaining four fractions (upper right of Venn diagram) were recognized uniquely by sera of noncavitary-TB patients.

The pattern of fractions recognized by HIV$^+$TB$^+$ patients was less complex, and the overlap with these other two patient categories was minimal (FIG. 3B). Thus, HIV$^+$TB$^+$ patient sera recognized 20 fractions, of which five overlapped with those fractions recognized by cavitary-TB patients, and of this latter group two also reacted with sera of noncavitary-TB patients.

Interestingly the 15 fractions that were recognized (significantly) only by sera of HIV$^+$TB$^+$ patients possessed very similar separation characteristics: (1) they originated from the CFP and were not precipitated with 67% ammonium sulfate, and (2) they bound strongly to the AIEX column, but weakly to the RP column. These 15 fractions (see FIG. 3A) correspond to the cluster of CFP fractions that showed enhanced reactivity with HIV$^+$TB$^+$ patients' sera (under the "*"). To confirm that the antigen(s) in these fractions were specific to TB rather than merely a result of HIV infection, the reactivity of three of the 15 fractions was assessed with serum samples of HIV$^+$ patients without TB. No antibody responses significantly above those of the PPD$^+$ healthy controls were observed (numerical results not shown).

Example V

Antigen Identification in Reactive Fractions Confirmed Reactivity to Known B-cell Antigens To identify individual antigens that would be the most useful in a serodiagnostic assay, additional stringency was applied to the array data, which further reduced the number of fractions demonstrating significant reactivity from 145 to 105. This was achieved by restricting analyses of the cavitary-TB specific fractions to those that yielded significant serological reactivity (≧3SD above the PPD$^+$ control mean) with 55% (6 of 11) or greater of cavitary-TB patients.

Figure 4:
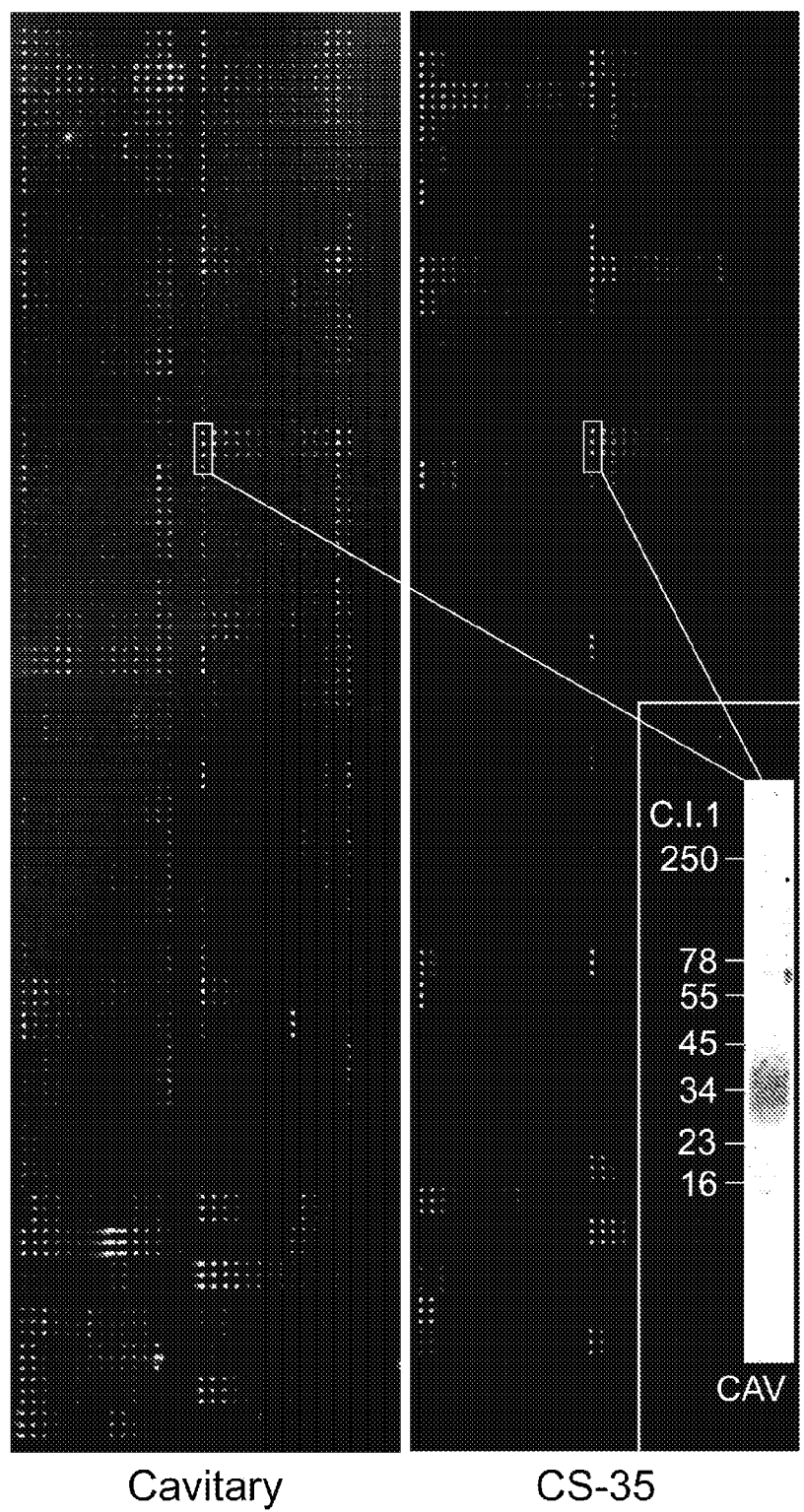
FIG. 4. Identification of reactive fractions containing lipoarabinomannan as the serodominant antigen. Shown are representative arrays probed with serum from a single cavitary-TB patient, and the LAM specific MAb CS-35. The inset is a Western blot of fraction C-I-1 probed with pooled cavitary-TB patients' sera.

It was also recognized that lipoarabinomannan (LAM), a well-characterized Mtb B cell antigen (27), would be present in some of the multidimensional fractions and was expected to be serologically dominant. To evaluate this, microarray slides were probed with the CS-35 mAb specific for LAM (FIG. 4). Of the 105-targeted fractions, 24 were found to contain LAM. The serological dominance of LAM was confirmed with conventional one-dimensional immunoblotting using pooled TB patients' sera (FIG. 4). It is interesting to note that the LAM-containing fractions consistently yielded microarray spots with the highest fluorescence intensities when probed with patient sera. Most of the PPD+ healthy control sera also reacted with these fractions. However, the reactivity of TB patients' sera was significantly stronger than that of the healthy PPD+ control sera (TABLE 6). The twenty-four LAM-containing fractions were excluded from further antigen analyses.

TABLE 6

Patient reactivity against LAM-containing fractions

| Fractionation Conditions | LAM-Reactivity Ratio[a] | | | |
|---|---|---|---|---|
| (X, Y, Z)[b] | PPD+ | HIV+ TB | Noncavitary TB | Cavitary TB |
| A-III-4 | 1.30 | 1.83 | 2.67 | 3.40 |
| A-IV-1 | 3.08 | 3.49 | 5.71 | 6.31 |
| A-IV-3 | 1.28 | 1.81 | 2.87 | 3.57 |
| A-V-1 | 1.67 | 2.45 | 3.71 | 4.92 |
| A-IX-1 | 1.41 | 2.48 | 3.33 | 3.94 |
| A-X/XI-1 | 1.06 | 1.49 | 1.74 | 1.99 |
| B-III-2 | 1.30 | 1.49 | 2.71 | 3.12 |
| B-III-7 | 0.99 | 1.38 | 1.99 | 2.06 |
| B-IV-1 | 2.30 | 2.61 | 4.33 | 5.72 |
| B-I-2 | 1.23 | 1.53 | 2.43 | 3.23 |
| C-III-1 | 1.18 | 1.41 | 2.14 | 2.19 |
| C-IV-1 | 1.00 | 1.12 | 1.59 | 1.36 |
| C-I-1 | 2.21 | 1.98 | 3.32 | 4.63 |
| C-I-2 | 1.64 | 1.71 | 2.59 | 3.58 |
| C-I-4 | 1.32 | 1.50 | 2.38 | 2.59 |
| C-I-13 | 1.27 | 1.66 | 2.00 | 2.21 |
| D-II/III/IV-1 | 1.68 | 1.84 | 3.15 | 3.91 |
| E-II-1 | 2.91 | 2.90 | 3.70 | 4.68 |
| E-III-1 | 1.07 | 1.45 | 1.66 | 1.47 |
| F-II-2 | 1.07 | 1.22 | 1.65 | 2.33 |
| F-II-3 | 0.98 | 1.24 | 1.40 | 1.60 |
| F-IV-1 | 1.00 | 1.32 | 1.80 | 1.59 |
| F-I-1 | 1.29 | 1.33 | 2.17 | 3.28 |
| F-I-2 | 1.27 | 1.45 | 2.73 | 3.28 |

[a]Disease category-averaged NAvSNR for the fraction/Disease category-averaged NAvSNR for the all 960 fractions.
[b]Key to fraction designation: X = Ammonium Sulfate cut A-F (see Materials and Methods), Y = AIEX fraction (13 sequential elution fractions, Roman Numeral I to XIII), "/" denotes pooled fractions, Z = RP-HPLC fraction (sequential elutions 1 through 15).

Figure 5:
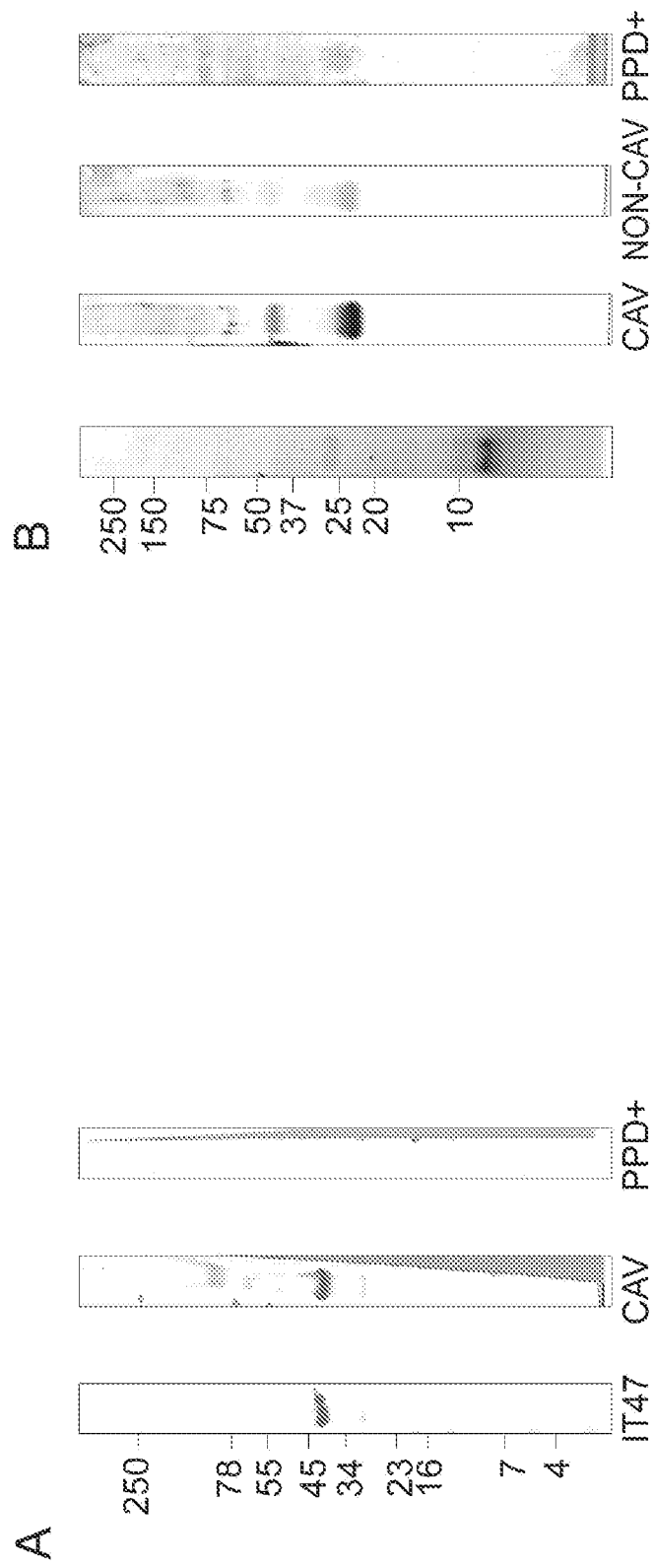
FIG. 5. Antibody and MS based identification of antigens composing reactive fractions. (A) Western blot analyses of fraction C-II-11 with MAb IT-27, pooled cavitary-TB patients' sera, and pooled PPD$^+$ healthy controls' sera (left to right) demonstrate the 38-kDa PstS1 protein as the dominant antigen in this fraction. (B) Fraction B-III-4 was analyzed (left to right) by SDS-PAGE and coomassie-staining, and Western blot with pooled sera from cavitary-TB, noncavitary-TB, and healthy PPD$^+$ individuals to demonstrate a 28-kDa protein as the dominant antigen. (C) Peptide sequences resolved by MS/MS of the coomassie-stained 28-kDa protein band after trypsin digestion identified the antigen as SodC.
Figure 6:
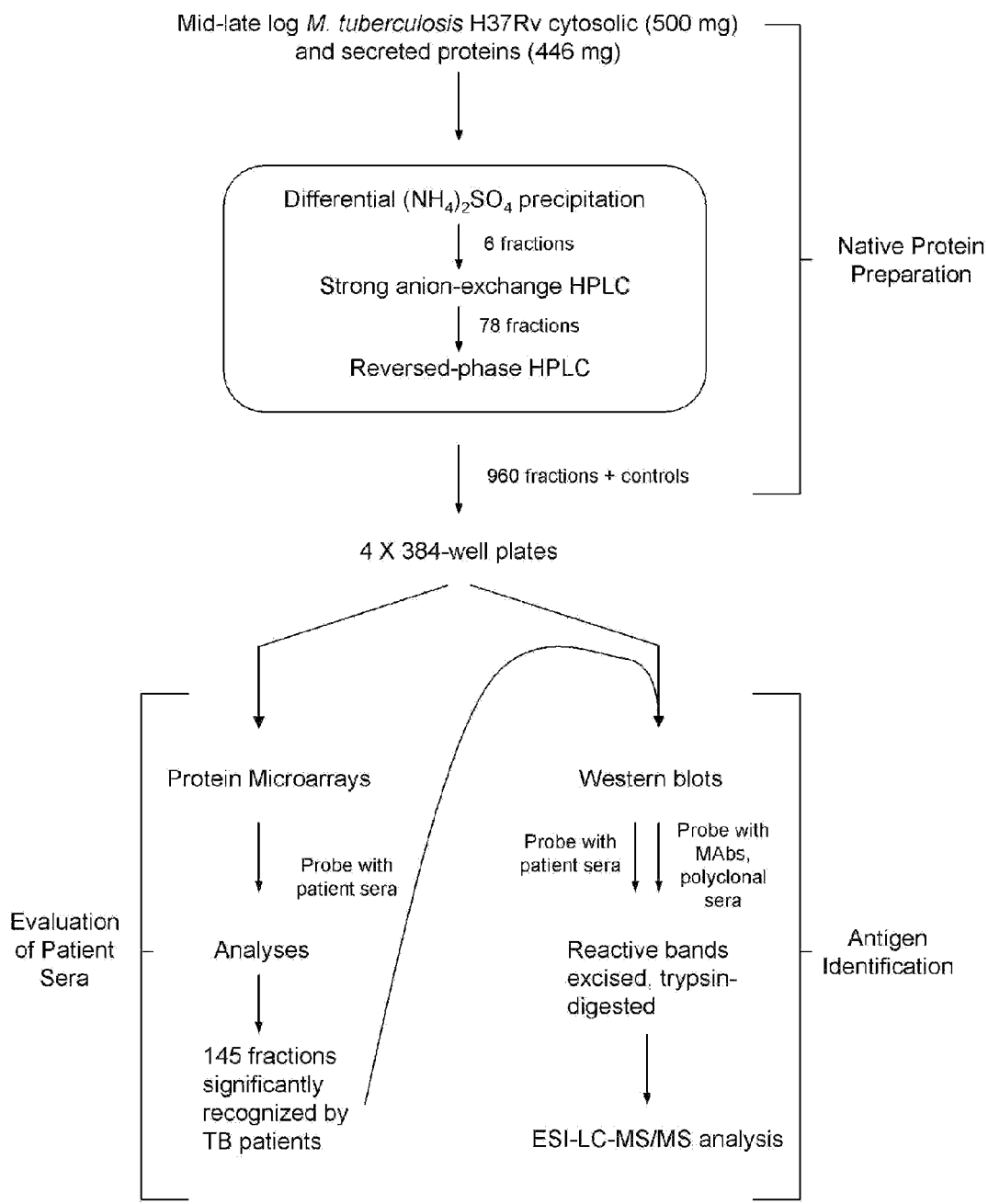
FIG. 6. Schematic of the approach to define the serological response of TB patients through native protein microarrays. The entire approach is divided into three major activities (Native Protein Preparation, Evaluation of Patient Sera, and Antigen Identification).

Molecular identities of the serologically active native proteins within the remaining fractions were obtained by two methods (FIG. 6). The first method utilized Western blot analyses with patient sera compared with mAbs or polyclonal sera specific for five distinct Mtb proteins (FIG. 5A). In the second approach, antigen composition of a fraction was determined by Western blot analysis with patient sera and identification of the corresponding Coomassie-stained protein band using MS/MS (FIGS. 5B and C). This combination of MS and antibody-based identification strategies resulted in an assigned antigen composition for 38 of the 81 remaining fractions.

Ten proteins previously found to be Mtb B cell antigens in humans ("human antigens")(2) accounted for all or part of the serological activity of 26 fractions (Table 7).

TABLE 7

Previously characterized antigens contained in serologically reactive fractions

| Antigen(s) | Fractionation Conditions (X, Y, Z)[a] | Patient Reactivity[b] | | |
|---|---|---|---|---|
| | | HIV+TB+ | Noncavitary TB | Cavitary TB |
| 38-kDa PstS1/Rv0934[c] | C-II-11 | 1/10 (10%) | 1/9 (11%) | 6/11 (55%) |
| 45-kDa Apa/ModD/Rv1860[d] | A-II-11 | 2/10 (20%) | 4/9 (44%) | 4/11 (36%) |
| | A-III-9 | 2/10 (20%) | 4/9 (44%) | 5/11 (44%) |
| | A-III-11 | 2/10 (20%) | 4/9 (44%) | 7/11 (64%) |
| | B-III-10 | 2/10 (20%) | 4/9 (44%) | 4/11 (36%) |
| Ag85B/Rv1886c[e] | B-VI-13 | 3/10 (30%) | 6/9 (67%) | 6/11 (55%) |
| | B-VI-14 | 3/10 (30%) | 3/9 (33%) | 7/11 (64%) |
| | A-VI-15 | 2/10 (20%) | 4/9 (44%) | 5/11 (44%) |
| GlcB/Rv1837c[e] | A-VI-3 | 3/10 (30%) | 4/9 (44%) | 6/11 (55%) |
| | A-VI-4 | 2/10 (20%) | 4/9 (44%) | 6/11 (55%) |
| | A-VII-3 | 3/10 (30%) | 4/9 (44%) | 6/11 (55%) |
| | A-VIII-3 | 2/10 (20%) | 4/9 (44%) | 6/11 (55%) |
| | A-VIII-4 | 2/10 (20%) | 4/9 (44%) | 5/11 (44%) |
| LAM[c] | A-III-4 | 2/10 (20%) | 4/9 (44%) | 6/11 (55%) |
| | A-IV-1 | 1/10 (10%) | 5/9 (56%) | 6/11 (55%) |
| | A-IV-3 | 2/10 (20%) | 4/9 (44%) | 6/11 (55%) |
| | A-IX-1 | 3/10 (30%) | 5/9 (56%) | 6/11 (55%) |
| | A-V-1 | 3/10 (30%) | 5/9 (56%) | 6/11 (55%) |
| | A-X/XI-1 | 3/10 (30%) | 4/9 (44%) | 7/11 (64%) |
| | B-I-2 | 2/10 (20%) | 4/9 (44%) | 6/11 (55%) |
| | B-III-2 | 1/10 (10%) | 4/9 (44%) | 6/11 (55%) |
| | B-III-7 | 2/10 (20%) | 3/9 (33%) | 6/11 (55%) |
| | B-IV-1 | 0/10 (0%) | 3/9 (33%) | 7/11 (64%) |
| | C-I-1 | 0/10 (0%) | 1/9 (11%) | 6/11 (55%) |
| | C-I-2 | 0/10 (0%) | 3/9 (33%) | 6/11 (55%) |
| | C-I-4 | 2/10 (20%) | 5/9 (56%) | 6/11 (55%) |
| | C-I-13 | 2/10 (20%) | 3/9 (33%) | 5/11 (55%) |
| | C-III-1 | 2/10 (20%) | 4/9 (44%) | 6/11 (55%) |

TABLE 7-continued

Previously characterized antigens contained in serologically reactive fractions

| Antigen(s) | Fractionation Conditions (X, Y, Z)[a] | Patient Reactivity[b] | | |
|---|---|---|---|---|
| | | HIV+TB+ | Noncavitary TB | Cavitary TB |
| | C-IV-1 | 2/10 (20%) | 4/9 (44%) | 6/11 (55%) |
| | D-II/III/IV-1 | 0/10 (0%) | 5/9 (56%) | 7/11 (64%) |
| | E-II-1 | 0/10 (0%) | 3/9 (33%) | 6/11 (55%) |
| | E-III-1 | 2/10 (20%) | 3/9 (33%) | 6/11 (55%) |
| | F-I-1 | 0/10 (0%) | 4/9 (44%) | 7/11 (64%) |
| | F-I-2 | 2/10 (20%) | 5/9 (56%) | 6/11 (55%) |
| | F-II-2 | 2/10 (20%) | 4/9 (44%) | 7/11 (55%) |
| | F-II-3 | 2/10 (20%) | 4/9 (44%) | 7/11 (55%) |
| | F-IV-1 | 2/10 (20%) | 3/9 (33%) | 7/11 (64%) |
| Rv3881c[e] | A-VII-10 | 2/10 (20%) | 3/9 (33%) | 7/11 (64%) |
| | A-VII-11 | 2/10 (20%) | 4/9 (44%) | 7/11 (64%) |
| SecE2/Rv0379[e] | A-I-4 | 2/10 (20%) | 4/9 (44%) | 5/11 (44%) |
| | B-I-4 | 3/10 (30%) | 5/9 (56%) | 5/11 (44%) |
| | F-I-3 | 2/10 (20%) | 3/9 (33%) | 6/11 (55%) |
| | A-I-3 | 1/10 (10%) | 4/9 (44%) | 6/11 (55%) |
| Ag85A/Rv3804c & | A-I-14 | 2/10 (20%) | 3/9 (33%) | 6/11 (55%) |
| Ag85B/Rv1886c[e] | A-I-13 | 2/10 (20%) | 4/9 (44%) | 5/11 (44%) |
| | A-VI-12 | 2/10 (20%) | 2/9 (22%) | 6/11 (55%) |
| 45 kDa & MPT64/Rv1980c[d] | A-III-10 | 2/10 (20%) | 3/9 (33%) | 6/11 (55%) |
| HspX/Rv2031c & 2 unknowns[c] | B-V-9 | 2/10 (20%) | 0/9 (0%) | 6/11 (55%) |
| 19-kDa/Rv3763 & 1 unknown[c] | B-I-7 | 2/10 (20%) | 4/9 (44%) | 4/11 (36%) |
| | C-I-14 | 2/10 (20%) | 3/9 (44%) | 6/11 (55%) |

[a]Key to fraction designation: X = Ammonium Sulfate cut A-F (see Materials and Methods), Y = AIEX fraction (13 sequential elution fractions, Roman Numeral I to XIII), "/" denotes pooled fractions, Z = RP-HPLC fraction (sequential elutions 1 through 15).
[b]Number (Percentage) of patient sera significantly reactive against fraction in question. Significances >3SD above PPD+ mean
[c]Antigen identification based on reactivity to an antigen-specific mAb
[d]Antigen identification based on reactivity to an antigen-specific mAb and MS/MS analyses.
[e]Antigen identification based on MS/MS analyses. Detailed MS/MS results are provided in Supplementary Table 6/2.

Reactivity with a mAb was the basis for identifying the presence of the 38-kDa PstS1 antigen, the 19-kDa lipoprotein antigen, and the 14-kDa HspX antigen in four reactive fractions. Specifically, the probing of a microarray slide with mAbs IT-23 and IT-47 identified PstS1 in fraction C-II-1. Western blot analyses with IT-47, cavitary-TB sera, and PPD+ healthy control sera also revealed a single protein that reacted with IT-47 and cavitary-TB patients' sera, but not sera of PPD+ healthy control individuals (FIG. 5A).

In this same manner, the 19-kDa antigen was found to be a reactive product of fractions B-I-7 and C-I-14, and HspX contributed to the reactivity of fraction B-V-9. It was also noted that fractions B-I-7 and C-I-14 each contained a second reactive product of 12 kDa and 45 kDa, respectively, and fraction B-V-9 contained two additional reactive proteins of 7 and 10 kDa. The identities of these unknown proteins were not determined due to lack of an adequate amount of protein.

The remaining seven previously described protein antigens (45 kDa Apa, 30 kDa Ag85A and 85B, GlcB, Rv3881c, SecE2, and MPT64) were identified by MS/MS analyses, and some of these were confirmed by reactivity with mAbs (Table 7 and 8). For some fractions, after Western blot analyses with patients' sera a sufficient amount of material was not available for protein identification. Thus, protein identity was obtained by MS/MS analysis of an adjacent fraction possessing a reactive band at the same molecular weight. This was done to identify the 45 kDa Apa in one fraction, Ag85B in four fractions, Ag85A in two fractions, GlcB in four fractions, SecE2 in three fractions, and Rv3881c in one fraction (Table 7).

TABLE 8

Novel antigens in Reactive Fractions

| Antigen(s) | Fractionation Conditions (X, Y, Z)[a] | Patient Reactivity[b] | | | |
|---|---|---|---|---|---|
| | | HIV+TB+ | Noncavitary TB | Cavitary TB | MS/MS[c] |
| BfrB/Rv3841 | A-VII-1 | 3/10 (30%) | 4/9 (44%) | 6/11 (55%) | (37) |
| | A-VIII-1 | 3/10 (30%) | 4/9 (44%) | 6/11 (55%) | |
| LppZ/Rv3006 | A-III-5 | 2/10 (20%) | 3/9 (33%) | 6/11 (55%) | (37) |
| | A-IV-4 | 2/10 (20%) | 4/9 (44%) | 5/11 (44%) | |
| | A-IV-5 | 2/10 (20%) | 3/9 (33%) | 6/11 (55%) | |
| | A-IV-6 | 2/10 (20%) | 3/9 (33%) | 6/11 (55%) | |
| | A-V-5 | 2/10 (20%) | 4/9 (44%) | 5/11 (44%) | |
| SodC/Rv0432 | B-III-3 | 2/10 (20%) | 4/9 (44%) | 6/11 (55%) | (42) |
| | B-III-4 | 2/10 (20%) | 5/9 (56%) | 8/11 (73%) | |
| | B-IV-3 | 2/10 (20%) | 4/9 (44%) | 7/11 (64%) | |
| | B-IV-4 | 3/10 (30%) | 3/9 (33%) | 7/11 (64%) | |

TABLE 8-continued

Novel antigens in Reactive Fractions

| Antigen(s) | Fractionation Conditions (X, Y, Z)[a] | Patient Reactivity[b] | | | MS/MS[c] |
|---|---|---|---|---|---|
| | | HIV+TB+ | Noncavitary TB | Cavitary TB | |
| Apa/Rv1860[d] & TrxC/Rv3914 | B-II-9 | 2/10 (20%) | 3/9 (33%) | 6/11 (55%) | (29)[e] |

[a]Key to fraction designation: X = Ammonium Sulfate cut A-F (see Materials and Methods), Y = AIEX fraction (13 sequential elution fractions, Roman Numeral I to XIII), "/" denotes pooled fractions, Z = RP-HPLC fraction (sequential elutions 1 through 15).
[b]Number (Percentage) of patient sera significantly reactive against fraction in question. Significant is >3 × SD above PPD+ mean.
[c]Antigen identification based on LC-ESI-MS/MS analysis. Percent amino acid sequence coverage is in parentheses.
[d]The Apa was identified with the MAb CS-93.
[e]The percent amino acid coverage is for TrxC.

Example VI

Discovery of Novel B-Cell Antigens with Serodiagnostic Value

The MS/MS-based approach to antigen identification led to the elucidation of four new Mtb B cell antigens (Table 8). The first of these, SodC (Rv0432) is a 27-kDa Cu/Zn superoxide dismutase (28) that was the sole reactive constituent of four fractions originating from the CFP pool (B-III-3, B-III-4, B-IV-3, and B-IV-4), and was significantly recognized by both noncavitary-(5/9) and cavitary-TB (8/11) sera (FIG. 5B). MS/MS analysis of the corresponding protein in fraction B-III-4 resulted in 42% amino-acid coverage of the predicted protein sequence encoded by open-reading frame (ORF) rv0432. Table 9 provides an example of results using one of these proteins, SodC.

analysis of the silver-stained polyacrylamide gels revealed the 20-kDa band was the sole protein constituent in both fractions.

TrxC (Rv3914), a 12-kDa thioredoxin (31), was found along with the 45-kDa Apa antigen to account for the serological reactivity of fraction B-II-9. In contrast to the other novel antigen-containing fractions, the only group of sera significantly reacting with fraction B-II-9 were from cavitary-TB patients (6/11). MS/MS analysis of the 12-kDa protein resulted in 29% amino-acid coverage of the predicted protein sequence encoded by ORF rv3914. Whether or not the significant reactivity of fraction B-II-9 was due to TrxC or the strongly seroreactive 45-kDa antigen (6) could not be determined at this stage.

When the serological results for all those fractions containing the four novel antigens were combined, it was discovered that 56% of noncavitary-TB sera and 91% of cavitary-TB sera

TABLE 9

| Protein | Peptide Sequence/ SEQ ID NO: | Observed Mass-to-Charge Ratio | Charge | Predicted MH+ | Peptide AA Position |
|---|---|---|---|---|---|
| SodC | FEFANGYATVTIATTGVGK/ | 15 | 974.0 | 2 | 1948.2 | 89-107 |
| | LTPGFHGLHIHQVGK/ | 16 | 820.7 | 2 | 1641.9 | 108-122 |
| | GDGSAMLVTTTDAFTMDDLLSGAK/ | 17 | 1208.6 | 2 | 2418.7 | 166-189 |
| | TAIIIHAGADNEANIPPER/ | 18 | 1010.7 | 2 | 2021.27 | 190-208 |
| | YVQVNGTPGPDETTLTTGDAGKR/ | 19 | 1189.7 | 2 | 2378.54 | 209-231 |

LppZ (Rv3006) was identified as the only reactive product of five fractions (A-III-5, A-IV-4, A-IV-5, A-IV-6, and A-V-5) originating from the CFP pool, and was strongly recognized by noncavitary-(4/9) and cavitary-TB (6/11) sera. These fractions were generated under similar yet separation conditions, and SDS-PAGE showed all possessed a dominant 45-kDa product. MS/MS analysis of the corresponding protein in fraction A-IV-5 resulted in 37% amino-acid coverage of the predicted protein sequence encoded by ORF rv3006.

BfrB (Rv3841), a putative iron-storage protein (29) previously disclosed to be a T cell antigen by one of the present inventors and colleagues (30), was identified as the reactive protein in two fractions (A-VII-1 and A-VIII-1). It was significantly reactive with 4/9 noncavitary- and 6/11 cavitary-TB sera. MS/MS analysis of the 20-kDa reactive product in fraction A-VIII-1 resulted in 37% amino-acid coverage of the predicted protein sequence encoded by ORF rv3841, and showed positive reactivity. In comparison, when the results for all those fractions that contained both these novel antigens and previously identified protein antigens were combined, it was evident that 78% of noncavitary-TB sera and 91% of cavitary-TB sera were reactive.

Of considerable interest were the 15 fractions that demonstrated significant reactivity only with serum samples from HIV+TB+ patients. Western blot analysis of these fractions with HIV+TB+ patient sera failed to demonstrate reactive bands. Furthermore, there were no common protein bands between these fractions when analyzed by SDS-PAGE and silver staining. However, treatment of these fractions with pronase (10 μg/ml for 60 min) prior to microarray printing significantly abrogated reactivity with patients' sera. Together these observations suggest that: (1) a single protein antigen may not be responsible for the reactivity of these 15 fractions; (2) a common antigen such as a small peptide may be responsible for the reactivity, or (3) the reactivity is due to a non-proteinaceous bacterial product complexed with protein.

Discussion of Examples I-VI

Previous studies from the present inventors' laboratories employed 2-D immunoblotting to characterize the profile of Mtb proteins recognized by TB patients' sera ((5, 10); U.S. Pat. Nos. 6,245,331 and 6,506,384; Int'l Pat. Publications WO03/073101 and WO03/012395).

However, the methods used are not well suited for analysis of large numbers of sera due to issues related to reproducibility, quantification of the results, and lack of suitability for high-throughput formats. Protein microarrays offer a means by which a large number of sera (or other fluids containing antibodies) can be analyzed not only to identify serologically reactive proteins, but to establish antigen recognition profiles based on the state or severity of disease (16).

At present a complete recombinant protein library of Mtb does not exist. Therefore, to perform protein microarray studies for TB, the present inventors conceived and implemented a novel approach involving a robust fractionation strategy that yielded 960 native protein fractions. The availability of such arrays allowed addressing of differences in the patterns of antigens recognized by individuals exhibiting various forms of TB. Specifically, TB patient sera recognized a much greater number of protein fractions than did sera of PPD$^+$ healthy controls. Secondly, sera from patients with noncavitary-TB recognized only a subset (44%) of the fractions that were recognized by sera of patients with advanced, cavitary disease. This pattern of reactivity agreed well with results obtained earlier by the present inventors and their colleagues using 2-D Western blot analysis where only three to four CFPs reacted to sera of PPD$^+$ healthy individuals and where 12 of the 26 cavitary-TB reactive proteins (46%) were recognized by noncavitary-TB patients (5, 10).

The inclusion of the steps of antigen identification in the studies presented above enabled a more in-depth assessment of the overlap between the three Mtb disease categories (cavitary, noncavitary and HIV$^+$TB$^+$). Of the 55 fractions recognized by both cavitary- and noncavitary-TB patient sera, 11 antigens (LAM, the 45 kDa Apa protein, the 19-kDa LpqH protein, Ag85A, Ag85B, BfrB, GlcB, LppZ, Rv3881c, SecE2, and SodC) were identified as being serologically dominant.

Of particular interest is the fact that all five fractions that comprised GlcB as the reactive species were recognized by both noncavitary- and cavitary-TB patients, confirming previous reports that this antigen is recognized early in disease progression ((5, 6); U.S. Pat. Nos. 6,245,331 and 6,506,384; Int'l Pat. Publications WO03/073101 and WO03/012395).

The present analyses also identified a total of 68 fractions recognized exclusively by cavitary-TB patients' sera. Most of the antigens represented by these fractions (the 45-kDa Apa protein, Ag85B, LppZ, SecE2, SodC, LAM, Rv3881c, and the 19-kDa protein) overlapped with those recognized by both cavitary- and noncavitary-TB patients. However, four antigens (38 kDa PstS1 protein, HspX, MPT64, and TrxC) were recognized only by cavitary-TB patient sera, thus, making available several additional antigens that are useful for demarcating cavitary—from noncavitary—TB patients. The identification of the 38-kDa PstS1 as a cavitary-TB specific antigen concurs with previous reports that this antigen is recognized predominantly by sera of patients with advanced disease (5, 6)

Previous experimental approaches failed to identify an antigen that distinguishes noncavitary-TB patients from individuals with other stages of the disease. In this study four native protein fractions were designated as noncavitary-TB specific based on selection parameters used herein. A more in-depth inspection of these fractions, however, suggested they are likely not noncavitary-TB specific because these four fractions were each recognized by 4/11 (36%) pf cavitary-TB patients, just missing the 40% cutoff that was chosen to construct the Venn diagram shown in FIG. 3B.

Additionally, the 45-kDa Apa protein and the 19-kDa protein were found to be the antigens responsible for reactivity in three of these four fractions, and these same antigens were also found in five fractions recognized by sera of cavitary-TB patients. Thus, a noncavitary-TB specific antigen remains elusive; regardless of methodology, noncavitary-TB patients appear to react with a subset of those antigens recognized by cavitary-TB patients.

In large part, the overall data and conclusions provided herein based on the microarray studies were consistent with earlier work. Nonetheless, a few discrepancies were noted with studies based on 2-D immunoblots (5, 10). In contrast to the qualitative 2-D immunoblot data, the results disclosed herein were quantitative. Thus, the selection of reactive antigens or fractions was based on the percentage of sera with a NAvSNR value greater than an experimentally determined cutoff. This led, for example, to the exclusion of two antigens that were previously identified using 2-D immunoblots but fell outside the criteria set in this study to define significant reactivity. This was most notable with GlcB and its reactivity to HIV$^+$TB$^+$ patients' sera. GlcB was previously shown to react with HIV$^+$TB$^+$ sera in both 2-D immunoblot and ELISA formats (3, 10). However, when the microarray data set was quantified, the percentage of HIV$^+$TB$^+$ patients that recognized GlcB-containing fractions was slightly below the 40% cutoff. Previous work shows that sera from this group of patients reacts to the same set of CFPs that are recognized by noncavitary-TB patients (10). However, the results present above define fractions containing an unidentifiable antigen as the only material with significant reactivity to HIV$^+$TB$^+$ patients sera. The exceptionally strong response HIV$^+$TB$^+$ sera with these fractions may have led to a bias in data analysis for this patient group.

A second difference from the 2-D Western blot data was the failure to define MPT51 as a dominant antigen. With 2-D PAGE, MPT51 readily separates from LAM and is recognized as a dominant antigen in multiple Mtb disease categories (10). Probing the native protein array slide with the MPT51-specfic mAb IT52 demonstrated that MPT51 cofractionated with LAM (results not shown). Since LAM-containing fractions were excluded from further protein antigen analyses, MPT51 was not designated here as a significant serological antigen. In previous work, the present inventors and colleagues noted that there were approximately 12 protein spots that reacted with patient sera by 2-D immunoblot, but that were unidentifiable (10). Although some of these 2-D protein spots may possibly correspond to the four novel antigens identified herein, it is risky to draw such conclusions without further analyses.

Over the past two decades, molecular identification of the dominant B and T cell protein antigens of Mtb was achieved through a myriad of techniques and approaches (2, 32, 33) The present invention with its protein microarray approach to TB serodiagnostics has enabled the identification of four novel antigens previously unnoticed by other methods.

Two of these antigens, SodC and LppZ, are believed to undergo post-translational modification. SodC was experimentally shown to be lipid-modified and associated with the bacterial membrane (34). This protein also contains three predicted glycosylation sites, and the 40-aa N-terminal fragment of SodC was found to bind Concanavalin A when fused to the 19-kDa-leader sequence and expressed in *M. smegmatis* (35). A method for predicting gram-positive lipoprotein motifs had also identified LppZ as a probable lipoprotein (36), and similar to SodC, this protein sequence also contains three predicted glycosylation sites (35). The native and recombinant forms of several Mtb proteins have been directly compared, and it is becoming increasingly clear that recombinant forms often lack modifications or conformational epitopes required for immunological recognition (6, 37, 38). The discovery of SodC and LppZ as B cell antigens adds to the growing list of post-translationally modified antigens of Mtb (39) and illustrates the need for a recombinant protein production system that results in structures mimicking native protein structures.

One of the other novel B cell antigens described herein (BfrB) was previously shown by the present inventors and colleagues to be a dominant T cell antigen for mice experimentally infected with Mtb (30), and the present study revealed that BfrB is also antigenic in human disease. Thus, like many other Mtb antigens, BfrB is strongly recognized by both the cellular and humoral arms of the immune system and could be targeted as a vaccine candidate or diagnostic tool. The final B cell antigen newly recognized herein, (TrxC) was originally identified by Nagai et al. (40) as MPT46, a major Mtb CFP. Further work established MPT46 as a thio reductase (31). Although this protein was previously known, the present invention represents the first evidence of its antigenic potential.

Through the work of multiple laboratories greater than sixteen Mtb proteins have been identified as potential serodiagnostic antigens and most are associated with the culture filtrate (2). Despite efforts to enrich for proteins of low abundance, a relatively small number of novel antigens were identified in this study. The inclusion of denaturing agents may have further improved protein resolution and increased antigen detection; however, such an approach might also destroy conformational epitopes. One alternative explanation for the low number of novel antigens identified herein is that the discovery of new serodiagnostic antigens from in vitro grown Mtb H37Rv CytP and CFP pools is nearly exhausted. Nevertheless, the cell envelope protein pool of *M. tuberculosis* is under-exploited for serodiagnostic antigen discovery, and the methodologies described herein enable B cell antigen discovery focusing on this fraction. It is likely that further antigen discovery will also be realized once microarray technology is applied to a complete Mtb recombinant protein library.

The present inventors' earlier work on the serological response to Mtb proteins in human disease indicated considerable homogeneity in this response among TB patients (10). The previously accepted dogma of heterogeneity in antigen recognition likely resulted from the differences in the immune responses among the various categories and states of Mtb disease and poor immunoreactivity of Mtb recombinant proteins expressed in *E. coli* (41).

The use of protein arrays has confirmed the present inventors' previous observations and hypotheses. Moreover, the ability to assess antigen recognition profiles between disease categories now allows identification of several proteins recognized by both cavitary- and noncavitary-TB patients, and at least four proteins that are diagnostic of cavitary-TB. Thus, according to the present invention, it is be possible to develop and assess targeted protein arrays that will not only enable serodiagnosis of TB, but also the determination of disease severity.

Example VII

Epitope Mapping of TrxC and BfrB

The proteins BfrB (SEQ ID NO:3) and TrxC (SEQ ID NO:4) were two of the proteins identified as being seroreactive by the screening of protein microarrays of Mtb cytosolic and culture filtrate proteins using TB patient sera (see above). Epitope mapping of the two proteins was performed to identify strongly immunogenic regions.

For this, overlapping peptides (20-mers overlapping by 10 residues) encompassing the entire sequence of the proteins were synthesized. The peptides and their sequences are shown above in Tables 3 and 4. Peptides were synthesized commercially on a Whatman 50 cellulose membrane (SPOTS membrane) by Sigma Genosys. The membranes were probed with a serum pool comprising of sera from 6 untreated TB patients and in which each serum was diluted 1:50 in 0.5% blocking buffer (from Roche Diagnostics)

The SPOTS membranes were rinsed with ethanol, washed with Tris-buffered saline (TBS), blocked in blocking buffer and exposed to the TB patient serum pool for 4 hours at room temp.

The membrane was then washed in TBS-Tween20 and exposed to a mixture of Protein-A conjugated to alkaline phosphatase (AP) and anti-human IgA also conjugated to AP. After washing the membranes, color was developed by using BCIP/NBT as substrate.

Figure 7:
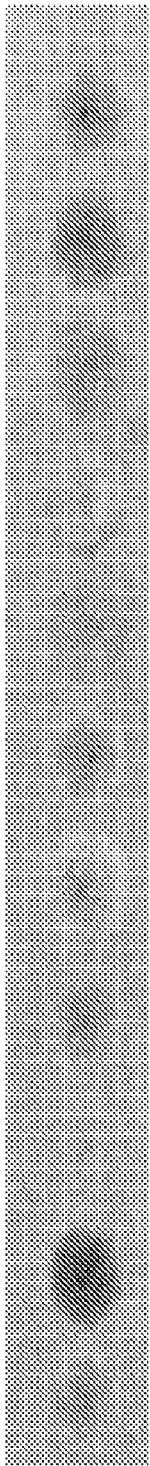
FIG. 7. Immunoreactivity of peptides from BfrB and TrxC proteins on SPOTS membranes using sera from TB patients.
Figure 7:

The reactivity of the peptides on the SPOTS membranes are shown in FIG. 7.

Reactivity of Individual Peptides with Individual TB Sera.

Each of the individual peptides from TrxC and BfrB were synthesized with a biotin residue attached to it's N terminus. Each TrxC peptide and selected BfrB peptides were tested for reactivity with sera from 36 PPD/PPD-healthy controls and 60 TB patients by ELISA.

Each peptide was suspended at 2.5 µg/ml, and 50 µl of the suspension was added to streptavidin-coated wells of ELISA microplates (Roche). To each well was added 50 µl of control or patient serum diluted 1:20 in blocking buffer (PBS containing 7.5% fetal calf serum and 2.5% BSA) diluted 1:10. After 1 hour, plates were washed and 100 µl of a mixture of AP-Protein A (1:2000) and anti-human IgA (1:1000) was added to each well. After 1 hour, the wells were washed, and 100 µl of the AP substrate PnPP (Sigma) were added.

The absorbance (optical density or OD) of the colored reaction product was read at 405 nm. The mean OD of the control wells +3 SD was set as a cutoff to determine sensitivity and specificity. The specificity with each of the peptides was >97%. Results of antibody binding to peptides are shown in Table 10, below The six BfrB peptides tested were shown to be recognized by sera of individual TB patients over a range of 3% to 68% of patient sera.

The 11 peptides of TrxC were shown to be recognized by sera of individual TB patients over a range of 17% to 62% of patient sera across peptides.

TABLE 10

Seroreactivity of BfrB and TrxC Peptides

| Peptide | AA sequence | SEQ ID NO: | % of Sera with positive reactivity* |
|---|---|---|---|
| BfrB peptides | | | |
| BfrB-1 | MTEYEGPKTK-FHALMQEQIH | 75 | 8% |
| BfrB-4 | AIAVYFDSED-LPQLAKHFYS | 78 | 15% |
| BfrB-5 | LPQLAKHFYS-QAVEERNHAM | 79 | 3% |
| BfrB-6 | QAVEERNHAM-MLVQHLLDRD | 80 | 12% |
| BfrB-8 | LRVEIPGVDT-VRNQFDRPRE | 82 | 62% |
| BfrB-18 | REVDVAPAAS-GAPHAAGGRL | 92 | 42% |
| TrxC peptides | | | |
| TrxC-1 | MTDSEKSATI-KVTDASFATD | 93 | 17% |
| TrxC-2 | KVTDASFATD-VLSSNKPVLV | 94 | 68% |
| TrxC-3 | VLSSNKPVLV-DFWATWCGPC | 95 | 35% |
| TrxC-4 | DFWATWCGPC-KMVAPVLEEI | 96 | 40% |
| TrxC-5 | KMVAPVLEEI-ATERATDLTV | 97 | 40% |
| TrxC-6 | ATERATDLTV-AKLDVDTNPE | 98 | 38% |
| TrxC-7 | AKLDVDTNPE-TARNFQVVSI | 99 | 28% |
| TrxC-8 | TARNFQVVSI-PTLILFKDGQ | 100 | 22% |
| TrxC-9 | PTLILFKDGQ-PVKRIVGAKG | 101 | 35% |
| TrxC-10 | PVKRIVGAKG-KAALLRELSD | 102 | 48% |
| TrxC-11 | GAKGKAALLR-ELSDWPNLN | 103 | 48% |

*above cutoff of control + 3 SD

REFERENCES

Cited in Text in Parentheses

1. World Health Organization (2005) *Global tuberculosis control—surveillance, planning, financing* (WHO Report 2005), Geneva, Switzerland
2. Laal, S et al. (2005) Immune-Based Methods, in *Tuberculosis and the Tubercle Bacillus*, pp. 71-83, ASM Press, Washington, D.C.
3. Laal, S et al. (1997) Surrogate marker of preclinical tuberculosis in human immunodeficiency virus infection: antibodies to an 88-kDa secreted antigen of *Mycobacterium tuberculosis*. *J Infect Dis.* 176, 133-143
4. Laal, S et al. (1997) Human humoral responses to antigens of *Mycobacterium tuberculosis*: immunodominance of high-molecular-mass antigens. *Clin Diagn Lab Immunol.* 4, 49-56
5. Samanich, K M et al., (1998) Delineation of human antibody responses to culture filtrate antigens of *Mycobacterium tuberculosis*. *J Infect Dis.* 178, 1534-1538
6. Samanich, K M et al., (2000) Serodiagnostic potential of culture filtrate antigens of *Mycobacterium tuberculosis*. *Clin Diagn Lab Immunol.* 7, 662-668
7. Singh, K K, Dong, Y., Hinds, L., Keen, M. A., Belisle, J. T., Zolla-Pazner, S., Achkar, J. M., Nadas, A. J., Arora, V. K. and Laal, S. (2003) Combined use of serum and urinary antibody for diagnosis of tuberculosis. *J Infect Dis.* 188, 371-377
8. Singh, K K et al, (2005) Antigens of *Mycobacterium tuberculosis* recognized by antibodies during incipient, subclinical tuberculosis. *Clin Diagn Lab Immunol.* 12, 354-358
9. Singh, K K et al, (2005) Immunogenicity of the *Mycobacterium tuberculosis* PPE55 (Rv3347c) protein during incipient and clinical tuberculosis. *Infect Immun.* 73, 5004-5014
10. Samanich, K et al, (2001) Homogeneity of antibody responses in tuberculosis patients. *Infect Immun.* 69, 4600-4609
11. Joos, T O et al, (2000) A microarray enzyme-linked immunosorbent assay for autoimmune diagnostics. *Electrophoresis.* 21, 2641-2650
12. Madoz-Gurpide, J et al, (2001) Protein based microarrays: a tool for probing the proteome of cancer cells and tissues. *Proteomics.* 1, 1279-1287
13. Kersten, B et al., (2003) Generation of *Arabidopsis* protein chips for antibody and serum screening. *Plant Mol. Biol.* 52, 999-1010
14. Bacarese-Hamilton, T et al, (2002) Protein microarrays: from serodiagnosis to whole proteome scale analysis of the immune response against pathogenic microorganisms. *Biotechniques. Suppl,* 24-29
15. Li, B et al., (2005) Protein microarray for profiling antibody responses to *Yersinia pestis* live vaccine. *Infect Immun.* 73, 3734-3739
16. Davies, D H et al. (2005) Profiling the humoral immune response to infection by using proteome microarrays: high-throughput vaccine and diagnostic antigen discovery. *Proc Natl Acad Sci USA.* 102, 547-552
17. Sonnenberg, M G et al (1997) Definition of *Mycobacterium tuberculosis* culture filtrate proteins by two-dimensional polyacrylamide gel electrophoresis, N-terminal amino acid sequencing, and electrospray mass spectrometry. *Infect Immun.* 65, 4515-4524
18. Dobos, K et al, (1996) Definition of the full extent of glycosylation of the 45-kilodalton glycoprotein of *Mycobacterium tuberculosis*. *J. Bacteriol* 178, 2498-2506
19. Hirschfield, G R et al (1990) Peptidoglycan-associated polypeptides of *Mycobacterium tuberculosis*. *J. Bacteriol.* 172, 1005-1013
20. Smith, P K et al (1985) Measurement of protein using bicinchoninic acid. *Anal Biochem.* 150, 76-85
21. Saeed, A I et al. (2003) TM4: a free, open-source system for microarray data management and analysis. *Biotechniques.* 34, 374-378
22. Laemmli, U K (1970) Cleavage of structural proteins during the assembly of the head of bacteriophage T4. *Nature.* 227, 680-685
23. Morrissey, J H (1981) Silver stain for proteins in polyacrylamide gels: a modified procedure with enhanced uniform sensitivity. *Anal Biochem.* 117, 307-310
24. Hellman, U et al (1995) Improvement of an "In-Gel" digestion procedure for the micropreparation of internal protein fragments for amino acid sequencing. *Anal Biochem.* 224, 451-455
25. McDonald, W H et al (2002) Shotgun proteomics and biomarker discovery. *Dis Markers.* 18, 99-105
26. Mawuenyega, K G et al (2005) *Mycobacterium tuberculosis* functional network analysis by global subcellular protein profiling. *Mol Biol Cell.* 16, 396-404

27. Sada, E et al (1990) Evaluation of lipoarabinomannan for the serological diagnosis of tuberculosis. *J Clin Microbiol.* 28, 2587-2590
28. Wu, C H et al (1998) Identification and subcellular localization of a novel Cu,Zn superoxide dismutase of *Mycobacterium tuberculosis*. *FEBS Lett.* 439, 192-196
29. Cole, S T et al. (1998) Deciphering the biology of *Mycobacterium tuberculosis* from the complete genome sequence. *Nature.* 393, 537-544
30. Covert, B A et al (2001) The application of proteomics in defining the T cell antigens of *Mycobacterium tuberculosis*. *Proteomics.* 1, 574-586
31. Wieles, B et al. (1995) Identification and functional characterization of thioredoxin of *Mycobacterium tuberculosis*. *Infect Immun.* 63, 4946-4948
32. Andersen, P et al (2005) TB subunit vaccines—putting the pieces together. *Microbes Infect.* 7, 911-921
33. Reed, S et al (2005) Tuberculosis vaccine development; from mouse to man. *Microbes Infect.* 7, 922-931
34. D Orazio, M et al (2001) Lipid modification of the Cu,Zn superoxide dismutase from *Mycobacterium tuberculosis*. *Biochem J.* 359, 17-22
35. Herrmann, J L et al. (2000) Analysis of post-translational modification of mycobacterial proteins using a cassette expression system. *FEBS Lett.* 473, 358-362
36. Sutcliffe, I C et at. (2004) Lipoproteins of *Mycobacterium tuberculosis*: an abundant and functionally diverse class of cell envelope components. *FEMS Microbiol Rev.* 28, 645-659
37. Romain, F et al. (1999) Deglycosylation of the 45/47-kilodalton antigen complex of *Mycobacterium tuberculosis* decreases its capacity to elicit in vivo or in vitro cellular immune responses. *Infect Immun.* 67, 5567-5572
38. Zanetti, S et al. (2005) Patients with pulmonary tuberculosis develop a strong humoral response against methylated heparin-binding hemagglutinin. *Clin Diagn Lab Immunol.* 12, 1135-1138
39. Belisle, J T et al. (2005) The Proteome of *Mycobacterium tuberculosis*, in *Tuberculosis and the Tubercle Bacillus*, pp. 235-260, ASM Press, Washington, D.C.
40. Nagai, S et al. (1991) Isolation and partial characterization of major protein antigens in the culture fluid of *Mycobacterium tuberculosis*. *Infect Immun.* 59, 372-382
41. Lyashchenko, K et al. (1998) Heterogeneous antibody responses in tuberculosis. *Infect Immun.* 66, 3936-3940

The references cited throughout this document above are all incorporated by reference herein, whether specifically incorporated or not. This Application incorporates by reference, in their entirety, the disclosure of U.S. Pat. Nos. 6,245,331 and 6,506,384 and Int'l Pat. Publications WO03/073101 and WO03/012395 and all references cited therein.

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A peptide of a *Mycobacteria tuberculosis* (Mtb) protein selected from the group consisting of:
   (a) an isolated peptide that is a fragment of Mtb SodC protein (SEQ ID NO:2) encoded by Mtb gene Rv0432, which peptide is recognized by an antibody from a subject infected with Mtb, the sequence of which peptide is SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, or SEQ ID NO:74;
   (b) an isolated peptide that is a fragment of Mtb BfrB protein (SEQ ID NO:3), which peptide is recognized by an antibody from a subject infected with Mtb, the sequence of which peptide is SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, or SEQ ID NO:92; and
   (c) an isolated peptide that is a fragment of Mtb TrxC protein (SEQ ID NO:4), which peptide is recognized by an antibody from a subject infected with Mtb, the sequence of which peptide is SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, or SEQ ID NO:103.

2. An antigenic composition that comprises
   (a) two or more isolated Mtb peptides of claim 1, or
   (b) a mixture of one or more of said isolated peptides and one or more Mtb protein selected from the group consisting of LppZ (SEQ ID NO:1), SodC (SEQ ID NO:2), BfrB (SEQ ID NO:3) and TrxC (SEQ ID NO:4).

3. The antigenic composition of claim 2 that comprises three or more of said Mtb peptides.

4. An antigenic composition that comprises a mixture of four isolated Mtb proteins LppZ, SodC, BfrB and TrxC, and/or at least one isolated peptide according to claim 1.

5. An antigenic composition comprising the isolated peptide of claim 1 and one or more of the following additional isolated Mtb proteins, or a peptide fragment of said additional Mtb protein that is recognized by an antibody from a subject infected with Mtb, said additional protein being selected from the group consisting of:
   (a) an isolated PstS1 protein encoded by Mtb gene Rv0934 the amino acid sequence of which is SEQ ID NO:5;
   (b) an isolated Apa/ModD protein encoded by Mtb gene Rv1860 the amino acid sequence of which is SEQ ID NO:6;
   (c) an isolated Ag85A protein encoded by Mtb gene Rv3804c the amino acid sequence of which is SEQ ID NO:7;
   (d) an isolated Ag85B protein encoded by Mtb gene Rv1886c the amino acid sequence of which is SEQ ID NO:8;
   (e) an isolated GlcB protein encoded by Mtb gene Rv1837c the amino acid sequence of which is SEQ ID NO:9;
   (f) an isolated protein encoded by Mtb gene Rv3881c the amino acid sequence of which is SEQ ID NO:10;
   (g) an isolated SecE2 protein encoded by Mtb gene Rv0379 the amino acid sequence of which is SEQ ID NO:11;
   (h) an isolated MPT64 protein encoded by Mtb gene Rv1980c the amino acid sequence of which is SEQ ID NO:12;
   (i) an isolated HspX protein encoded by Mtb gene Rv2031c the amino acid sequence of which is SEQ ID NO:13; and
   (j) an isolated LpqH protein encoded by Mtb gene Rv3763 the amino acid sequence of which is SEQ ID NO:14.

6. A kit useful for early detection of Mtb disease or infection comprising:
   (a) an Mtb antigen or antigens in the form of the peptide according to claim 1;
   (b) reagents necessary for detection of antibodies which bind to said Mtb peptide; and
   (c) optionally, a set of instructions for carrying out the detection.

7. An immunoassay composition that comprises the peptide according to claim 1 immobilized to a solid support.

8. The immunoassay composition of claim 7 that is arranged in a format suitable for use in an ELISA or dipstick-based immunoassay.

9. A method for serological early detection of Mtb disease or infection in a subject, comprising assaying a biological fluid sample from a subject having symptoms of active tuberculosis, but before the onset of symptoms identifiable as advanced tuberculosis, for the presence of antibodies that bind to said peptide of claim 1.

10. The method of claim 9 wherein the assaying is performed using an ELISA or a dipstick-based immunoassay.

11. The method of claim 9 that further includes performance of a test that detects Mtb bacilli in a sample of sputum or other body fluid of said subject.

12. The method of claim 9 wherein said sample is serum, urine or saliva.

13. The method of claim 9 wherein said subject is a human.

14. The method of claim 13 wherein said subject is one who is infected with HIV-1 or is at high risk for tuberculosis.

15. A TrxC peptide according to claim 1 selected from the group consisting of SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, and SEQ ID NO:103.

16. An antigenic composition comprising the isolated peptide of claim 15 and one or more of the following additional isolated Mtb proteins, or a peptide fragment of said additional Mtb protein that is recognized by an antibody from a subject infected with Mtb, said additional protein being selected from the group consisting of:
   (a) an isolated PstS1 protein encoded by Mtb gene Rv0934 the amino acid sequence of which is SEQ ID NO:5;
   (b) an isolated Apa/ModD protein encoded by Mtb gene Rv1860 the amino acid sequence of which is SEQ ID NO:6;
   (c) an isolated Ag85A protein encoded by Mtb gene Rv3804c the amino acid sequence of which is SEQ ID NO:7;
   (d) an isolated Ag85B protein encoded by Mtb gene Rv1886c the amino acid sequence of which is SEQ ID NO:8;
   (e) an isolated GlcB protein encoded by Mtb gene Rv1837c the amino acid sequence of which is SEQ ID NO:9;
   (f) an isolated protein encoded by Mtb gene Rv3881c the amino acid sequence of which is SEQ ID NO:10;

(g) an isolated SecE2 protein encoded by Mtb gene Rv0379 the amino acid sequence of which is SEQ ID NO:11;

(h) an isolated MPT64 protein encoded by Mtb gene Rv1980c the amino acid sequence of which is SEQ ID NO:12;

(i) an isolated HspX protein encoded by Mtb gene Rv2031c the amino acid sequence of which is SEQ ID NO:13; and (j) an isolated LpqH protein encoded by Mtb gene Rv3763 the amino acid sequence of which is SEQ ID NO:14.

17. An antigenic composition that comprises
    (a) two or more isolated Mtb peptides of claim 15, or
    (b) a mixture of one or more of said isolated peptides and one or more Mtb proteins selected from the group consisting of LppZ (SEQ ID NO:1), SodC (SEQ ID NO:2), BfrB (SEQ ID NO:3) and TrxC (SEQ ID NO:4).

18. The antigenic composition of claim 17 that comprises three or more of said Mtb peptides.

19. A method for serological early detection of Mtb disease or infection in a subject, comprising assaying a biological fluid sample from a subject having symptoms of active tuberculosis, but before the onset of symptoms identifiable as advanced tuberculosis, for the presence of antibodies that bind to said peptide of claim 15.

20. The method of claim 19 wherein the assaying is performed using an ELISA or a dipstick-based immunoassay.

21. The method of claim 19 wherein said sample is serum, urine or saliva.

22. An immunoassay composition that comprises the peptide of claim 15 immobilized to a solid support.

23. A kit useful for early detection of Mtb disease or infection comprising:
    (a) an Mtb antigen or antigens in the form of the peptide according to claim 15;
    (b) reagents necessary for detection of antibodies which bind to said Mtb peptide; and
    (c) optionally, a set of instructions for carrying out the detection.

24. A BfrB peptide according to claim 1 selected from the group consisting of SEQ ID NO:75, SEQ ID NO:78, SEQ ID NO:79, SEQ ID NO:80, SEQ ID NO:82 and SEQ ID NO:92.

25. An immunoassay composition that comprises the peptide of claim 24 immobilized to a solid support.

26. An antigenic composition that comprises
    (a) two or more isolated Mtb peptides of claim 24, or
    (b) a mixture of one or more of said isolated peptides and one or more Mtb protein selected from the group consisting of LppZ (SEQ ID NO:1), SodC (SEQ ID NO:2), BfrB (SEQ ID NO:3) and TrxC (SEQ ID NO:4).

27. The antigenic composition of claim 26 that comprises three or more of said Mtb peptides.

28. A kit useful for early detection of Mtb disease or infection comprising:
    (a) an Mtb antigen or antigens in the form of the peptide according to claim 24;
    (b) reagents necessary for detection of antibodies which bind to said Mtb peptide; and
    (c) optionally, a set of instructions for carrying out the detection.

29. An antigenic composition comprising the isolated peptide of claim 24 and one or more of the following additional isolated Mtb proteins, or a peptide fragment of said additional Mtb protein that is recognized by an antibody from a subject infected with Mtb, said additional protein being selected from the group consisting of:
    (a) an isolated PstS1 protein encoded by Mtb gene Rv0934 the amino acid sequence of which is SEQ ID NO:5;
    (b) an isolated Apa/ModD protein encoded by Mtb gene Rv1860 the amino acid sequence of which is SEQ ID NO:6;
    (c) an isolated Ag85A protein encoded by Mtb gene Rv3804c the amino acid sequence of which is SEQ ID NO:7;
    (d) an isolated Ag85B protein encoded by Mtb gene Rv1886c the amino acid sequence of which is SEQ ID NO:8;
    (e) an isolated GlcB protein encoded by Mtb gene Rv1837c the amino acid sequence of which is SEQ ID NO:9;
    (f) an isolated protein encoded by Mtb gene Rv3881c the amino acid sequence of which is SEQ ID NO:10;
    (g) an isolated SecE2 protein encoded by Mtb gene Rv0379 the amino acid sequence of which is SEQ ID NO:11;
    (h) an isolated MPT64 protein encoded by Mtb gene Rv1980c the amino acid sequence of which is SEQ ID NO:12;
    (i) an isolated HspX protein encoded by Mtb gene Rv2031c the amino acid sequence of which is SEQ ID NO:13; and
    (j) an isolated LpqH protein encoded by Mtb gene Rv3763 the amino acid sequence of which is SEQ ID NO:14.

30. A method for serological early detection of Mtb disease or infection in a subject, comprising assaying a biological fluid sample from a subject having symptoms of active tuberculosis, but before the onset of symptoms identifiable as advanced tuberculosis, for the presence of antibodies that bind to said peptide of claim 24.

31. The method of claim 30 wherein the assaying is performed using an ELISA or a dipstick-based immunoassay.

32. The method of claim 30 that further includes performance of a test that detects Mtb bacilli in a sample of sputum or other body fluid of said subject.

33. The method of claim 30 wherein said sample is serum, urine or saliva.

* * * * *

```
                          SEQUENCE LISTING

<160> NUMBER OF SEQ ID NOS: 104

<210> SEQ ID NO 1
<211> LENGTH: 373
<212> TYPE: PRT
<213> ORGANISM: Mycobacterium tuberculosis
<220> FEATURE:
<221> NAME/KEY: misc_feature
<223> OTHER INFORMATION: LppZ

<400> SEQUENCE: 1

Met Trp Thr Thr Arg Leu Val Arg Ser Gly Leu Ala Ala Leu Cys Ala
1               5                   10                  15

Ala Val Leu Val Ser Ser Gly Cys Ala Arg Phe Asn Asp Ala Gln Ser
            20                  25                  30

Gln Pro Phe Thr Thr Glu Pro Glu Leu Arg Pro Gln Pro Ser Ser Thr
        35                  40                  45

Pro Pro Pro Pro Pro Leu Pro Pro Val Pro Phe Pro Lys Glu Cys
    50                  55                  60

Pro Ala Pro Gly Val Met Gln Gly Cys Leu Glu Ser Thr Ser Gly Leu
65                  70                  75                  80

Ile Met Gly Ile Asp Ser Lys Thr Ala Leu Val Ala Glu Arg Ile Thr
                85                  90                  95

Gly Ala Val Glu Glu Ile Ser Ile Ser Ala Glu Pro Lys Val Lys Thr
            100                 105                 110

Val Ile Pro Val Asp Pro Ala Gly Asp Gly Gly Leu Met Asp Ile Val
        115                 120                 125

Leu Ser Pro Thr Tyr Ser Gln Asp Arg Leu Met Tyr Ala Tyr Ile Ser
    130                 135                 140
```

```
Thr Pro Thr Asp Asn Arg Val Arg Val Ala Asp Gly Asp Ile Pro
145                 150                 155                 160

Lys Asp Ile Leu Thr Gly Ile Pro Lys Gly Ala Ala Gly Asn Thr Gly
            165                 170                 175

Ala Leu Ile Phe Thr Ser Pro Thr Thr Leu Val Val Met Thr Gly Asp
            180                 185                 190

Ala Gly Asp Pro Ala Leu Ala Ala Asp Pro Gln Ser Leu Ala Gly Lys
        195                 200                 205

Val Leu Arg Ile Glu Gln Pro Thr Thr Ile Gly Gln Thr Pro Pro Thr
    210                 215                 220

Thr Ala Leu Ser Gly Ile Gly Ser Gly Gly Leu Cys Ile Asp Pro
225                 230                 235                 240

Val Asp Gly Ser Leu Tyr Val Ala Asp Arg Thr Pro Thr Ala Asp Arg
                245                 250                 255

Leu Gln Arg Ile Thr Lys Asn Ser Glu Val Ser Thr Val Trp Thr Trp
            260                 265                 270

Pro Asp Lys Pro Gly Val Ala Gly Cys Ala Ala Met Asp Gly Thr Val
        275                 280                 285

Leu Val Asn Leu Ile Asn Thr Lys Leu Thr Val Ala Val Arg Leu Ala
    290                 295                 300

Pro Ser Thr Gly Ala Val Thr Gly Glu Pro Asp Val Val Arg Lys Asp
305                 310                 315                 320

Thr His Ala His Ala Trp Ala Leu Arg Met Ser Pro Asp Gly Asn Val
                325                 330                 335

Trp Gly Ala Thr Val Asn Lys Thr Ala Gly Asp Ala Glu Lys Leu Asp
            340                 345                 350

Asp Val Val Phe Pro Leu Phe Pro Gln Gly Gly Gly Phe Pro Arg Asn
        355                 360                 365

Asn Asp Asp Lys Thr
    370

<210> SEQ ID NO 2
<211> LENGTH: 240
<212> TYPE: PRT
<213> ORGANISM: Mycobacterium tuberculosis
<220> FEATURE:
<221> NAME/KEY: misc_feature
<223> OTHER INFORMATION: SodC

<400> SEQUENCE: 2

Met Pro Lys Pro Ala Asp His Arg Asn His Ala Ala Val Ser Thr Ser
1               5                   10                  15

Val Leu Ser Ala Leu Phe Leu Gly Ala Gly Ala Ala Leu Leu Ser Ala
            20                  25                  30

Cys Ser Ser Pro Gln His Ala Ser Thr Val Pro Gly Thr Thr Pro Ser
        35                  40                  45

Ile Trp Thr Gly Ser Pro Ala Pro Ser Gly Leu Ser Gly His Asp Glu
    50                  55                  60

Glu Ser Pro Gly Ala Gln Ser Leu Thr Ser Thr Leu Thr Ala Pro Asp
65                  70                  75                  80

Gly Thr Lys Val Ala Thr Ala Lys Phe Glu Phe Ala Asn Gly Tyr Ala
                85                  90                  95

Thr Val Thr Ile Ala Thr Thr Gly Val Gly Lys Leu Thr Pro Gly Phe
            100                 105                 110

His Gly Leu His Ile His Gln Val Gly Lys Cys Glu Pro Asn Ser Val
        115                 120                 125
```

```
Ala Pro Thr Gly Gly Ala Pro Gly Asn Phe Leu Ser Ala Gly Gly His
        130                 135                 140

Tyr His Val Pro Gly His Thr Gly Thr Pro Ala Ser Gly Asp Leu Ala
145                 150                 155                 160

Ser Leu Gln Val Arg Gly Asp Gly Ser Ala Met Leu Val Thr Thr Thr
                165                 170                 175

Asp Ala Phe Thr Met Asp Leu Leu Ser Gly Ala Lys Thr Ala Ile
            180                 185                 190

Ile Ile His Ala Gly Ala Asp Asn Phe Ala Asn Ile Pro Pro Glu Arg
                195                 200                 205

Tyr Val Gln Val Asn Gly Thr Pro Gly Pro Asp Glu Thr Thr Leu Thr
        210                 215                 220

Thr Gly Asp Ala Gly Lys Arg Val Ala Cys Gly Val Ile Gly Ser Gly
225                 230                 235                 240

<210> SEQ ID NO 3
<211> LENGTH: 181
<212> TYPE: PRT
<213> ORGANISM: Mycobacterium tuberculosis
<220> FEATURE:
<221> NAME/KEY: misc_feature
<223> OTHER INFORMATION: BfrB

<400> SEQUENCE: 3

Met Thr Glu Tyr Glu Gly Pro Lys Thr Lys Phe His Ala Leu Met Gln
1               5                   10                  15

Glu Gln Ile His Asn Glu Phe Thr Ala Ala Gln Gln Tyr Val Ala Ile
                20                  25                  30

Ala Val Tyr Phe Asp Ser Glu Asp Leu Pro Gln Leu Ala Lys His Phe
            35                  40                  45

Tyr Ser Gln Ala Val Glu Glu Arg Asn His Ala Met Met Leu Val Gln
        50                  55                  60

His Leu Leu Asp Arg Asp Leu Arg Val Glu Ile Pro Gly Val Asp Thr
65                  70                  75                  80

Val Arg Asn Gln Phe Asp Arg Pro Arg Glu Ala Leu Ala Leu Ala Leu
                85                  90                  95

Asp Gln Glu Arg Thr Val Thr Asp Gln Val Gly Arg Leu Thr Ala Val
            100                 105                 110

Ala Arg Asp Glu Gly Asp Phe Leu Gly Glu Gln Phe Met Gln Trp Phe
        115                 120                 125

Leu Gln Glu Gln Ile Glu Glu Val Ala Leu Met Ala Thr Leu Val Arg
130                 135                 140

Val Ala Asp Arg Ala Gly Ala Asn Leu Phe Glu Leu Glu Asn Phe Val
145                 150                 155                 160

Ala Arg Glu Val Asp Val Ala Pro Ala Ala Ser Gly Ala Pro His Ala
                165                 170                 175

Ala Gly Gly Arg Leu
            180

<210> SEQ ID NO 4
<211> LENGTH: 116
<212> TYPE: PRT
<213> ORGANISM: Mycobacterium tuberculosis
<220> FEATURE:
<221> NAME/KEY: misc_feature
<223> OTHER INFORMATION: TrxC

<400> SEQUENCE: 4
```

```
Met Thr Asp Ser Glu Lys Ser Ala Thr Ile Lys Val Thr Asp Ala Ser
1               5                   10                  15

Phe Ala Thr Asp Val Leu Ser Ser Asn Lys Pro Val Leu Val Asp Phe
            20                  25                  30

Trp Ala Thr Trp Cys Gly Pro Cys Lys Met Val Ala Pro Val Leu Glu
            35                  40                  45

Glu Ile Ala Thr Glu Arg Ala Thr Asp Leu Thr Val Ala Lys Leu Asp
        50                  55                  60

Val Asp Thr Asn Pro Glu Thr Ala Arg Asn Phe Gln Val Val Ser Ile
65                  70                  75                  80

Pro Thr Leu Ile Leu Phe Lys Asp Gly Gln Pro Val Lys Arg Ile Val
                85                  90                  95

Gly Ala Lys Gly Lys Ala Ala Leu Leu Arg Glu Leu Ser Asp Val Val
                100                 105                 110

Pro Asn Leu Asn
        115

<210> SEQ ID NO 5
<211> LENGTH: 374
<212> TYPE: PRT
<213> ORGANISM: Mycobacterium tuberculosis
<220> FEATURE:
<221> NAME/KEY: misc_feature
<223> OTHER INFORMATION: PhoS1 or  PstS1

<400> SEQUENCE: 5

Val Lys Ile Arg Leu His Thr Leu Leu Ala Val Leu Thr Ala Ala Pro
1               5                   10                  15

Leu Leu Leu Ala Ala Ala Gly Cys Gly Ser Lys Pro Pro Ser Gly Ser
            20                  25                  30

Pro Glu Thr Gly Ala Gly Ala Gly Thr Val Ala Thr Thr Pro Ala Ser
            35                  40                  45

Ser Pro Val Thr Leu Ala Glu Thr Gly Ser Thr Leu Leu Tyr Pro Leu
        50                  55                  60

Phe Asn Leu Trp Gly Pro Ala Phe His Glu Arg Tyr Pro Asn Val Thr
65                  70                  75                  80

Ile Thr Ala Gln Gly Thr Gly Ser Gly Ala Gly Ile Ala Gln Ala Ala
                85                  90                  95

Ala Gly Thr Val Asn Ile Gly Ala Ser Asp Ala Tyr Leu Ser Glu Gly
                100                 105                 110

Asp Met Ala Ala His Lys Gly Leu Met Asn Ile Ala Leu Ala Ile Ser
            115                 120                 125

Ala Gln Gln Val Asn Tyr Asn Leu Pro Gly Val Ser Glu His Leu Lys
        130                 135                 140

Leu Asn Gly Lys Val Leu Ala Ala Met Tyr Gln Gly Thr Ile Lys Thr
145                 150                 155                 160

Trp Asp Asp Pro Gln Ile Ala Ala Leu Asn Pro Gly Val Asn Leu Pro
                165                 170                 175

Gly Thr Ala Val Val Pro Leu His Arg Ser Asp Gly Ser Gly Asp Thr
                180                 185                 190

Phe Leu Phe Thr Gln Tyr Leu Ser Lys Gln Asp Pro Glu Gly Trp Gly
            195                 200                 205

Lys Ser Pro Gly Phe Gly Thr Thr Val Asp Phe Pro Ala Val Pro Gly
        210                 215                 220

Ala Leu Gly Glu Asn Gly Asn Gly Gly Met Val Thr Gly Cys Ala Glu
```

-continued

```
            225                 230                 235                 240
Thr Pro Gly Cys Val Ala Tyr Ile Gly Ile Ser Phe Leu Asp Gln Ala
                245                 250                 255

Ser Gln Arg Gly Leu Gly Glu Ala Gln Leu Gly Asn Ser Ser Gly Asn
                260                 265                 270

Phe Leu Leu Pro Asp Ala Gln Ser Ile Gln Ala Ala Ala Gly Phe
                275                 280                 285

Ala Ser Lys Thr Pro Ala Asn Gln Ala Ile Ser Met Ile Asp Gly Pro
        290                 295                 300

Ala Pro Asp Gly Tyr Pro Ile Ile Asn Tyr Glu Tyr Ala Ile Val Asn
305                 310                 315                 320

Asn Arg Gln Lys Asp Ala Ala Thr Ala Gln Thr Leu Gln Ala Phe Leu
                325                 330                 335

His Trp Ala Ile Thr Asp Gly Asn Lys Ala Ser Phe Leu Asp Gln Val
                340                 345                 350

His Phe Gln Pro Leu Pro Pro Ala Val Val Lys Leu Ser Asp Ala Leu
                355                 360                 365

Ile Ala Thr Ile Ser Ser
        370

<210> SEQ ID NO 6
<211> LENGTH: 325
<212> TYPE: PRT
<213> ORGANISM: Mycobacterium tuberculosis
<220> FEATURE:
<221> NAME/KEY: misc_feature
<223> OTHER INFORMATION: Apa/ModD or  MPT32

<400> SEQUENCE: 6

Met His Gln Val Asp Pro Asn Leu Thr Arg Arg Lys Gly Arg Leu Ala
1               5                   10                  15

Ala Leu Ala Ile Ala Ala Met Ala Ser Ala Ser Leu Val Thr Val Ala
                20                  25                  30

Val Pro Ala Thr Ala Asn Ala Asp Pro Glu Pro Ala Pro Pro Val Pro
            35                  40                  45

Thr Thr Ala Ala Ser Pro Pro Ser Thr Ala Ala Ala Pro Pro Ala Pro
    50                  55                  60

Ala Thr Pro Val Ala Pro Pro Pro Ala Ala Ala Asn Thr Pro Asn
65                  70                  75                  80

Ala Gln Pro Gly Asp Pro Asn Ala Ala Pro Pro Ala Asp Pro Asn
                85                  90                  95

Ala Pro Pro Pro Val Ile Ala Pro Asn Ala Pro Gln Pro Val Arg
            100                 105                 110

Ile Asp Asn Pro Val Gly Gly Phe Ser Phe Ala Leu Pro Ala Gly Trp
        115                 120                 125

Val Glu Ser Asp Ala Ala His Phe Asp Tyr Gly Ser Ala Leu Leu Ser
    130                 135                 140

Lys Thr Thr Gly Asp Pro Pro Phe Pro Gly Gln Pro Pro Val Ala
145                 150                 155                 160

Asn Asp Thr Arg Ile Val Leu Gly Arg Leu Asp Gln Lys Leu Tyr Ala
                165                 170                 175

Ser Ala Glu Ala Thr Asp Ser Lys Ala Ala Ala Arg Leu Gly Ser Asp
            180                 185                 190

Met Gly Glu Phe Tyr Met Pro Tyr Pro Gly Thr Arg Ile Asn Gln Glu
        195                 200                 205
```

-continued

```
Thr Val Ser Leu Asp Ala Asn Gly Val Ser Gly Ser Ala Ser Tyr Tyr
    210                 215                 220

Glu Val Lys Phe Ser Asp Pro Ser Lys Pro Asn Gly Gln Ile Trp Thr
225                 230                 235                 240

Gly Val Ile Gly Ser Pro Ala Ala Asn Ala Pro Asp Ala Gly Pro Pro
                245                 250                 255

Gln Arg Trp Phe Val Val Trp Leu Gly Thr Ala Asn Asn Pro Val Asp
            260                 265                 270

Lys Gly Ala Ala Lys Ala Leu Ala Glu Ser Ile Arg Pro Leu Val Ala
        275                 280                 285

Pro Pro Pro Ala Pro Ala Pro Ala Pro Ala Glu Pro Ala Pro Ala Pro
290                 295                 300

Ala Pro Ala Gly Glu Val Ala Pro Thr Pro Thr Thr Pro Thr Pro Gln
305                 310                 315                 320

Arg Thr Leu Pro Ala
            325

<210> SEQ ID NO 7
<211> LENGTH: 338
<212> TYPE: PRT
<213> ORGANISM: Mycobacterium tuberculosis
<220> FEATURE:
<221> NAME/KEY: misc_feature
<223> OTHER INFORMATION: FbpA or Ag85A

<400> SEQUENCE: 7

Met Gln Leu Val Asp Arg Val Arg Gly Ala Val Thr Gly Met Ser Arg
1               5                   10                  15

Arg Leu Val Val Gly Ala Val Gly Ala Ala Leu Val Ser Gly Leu Val
            20                  25                  30

Gly Ala Val Gly Gly Thr Ala Thr Ala Gly Ala Phe Ser Arg Pro Gly
        35                  40                  45

Leu Pro Val Glu Tyr Leu Gln Val Pro Ser Pro Ser Met Gly Arg Asp
    50                  55                  60

Ile Lys Val Gln Phe Gln Ser Gly Gly Ala Asn Ser Pro Ala Leu Tyr
65                  70                  75                  80

Leu Leu Asp Gly Leu Arg Ala Gln Asp Asp Phe Ser Gly Trp Asp Ile
                85                  90                  95

Asn Thr Pro Ala Phe Glu Trp Tyr Asp Gln Ser Gly Leu Ser Val Val
            100                 105                 110

Met Pro Val Gly Gly Gln Ser Ser Phe Tyr Ser Asp Trp Tyr Gln Pro
        115                 120                 125

Ala Cys Gly Lys Ala Gly Cys Gln Thr Tyr Lys Trp Glu Thr Phe Leu
    130                 135                 140

Thr Ser Glu Leu Pro Gly Trp Leu Gln Ala Asn Arg His Val Lys Pro
145                 150                 155                 160

Thr Gly Ser Ala Val Val Gly Leu Ser Met Ala Ser Ser Ala Leu
                165                 170                 175

Thr Leu Ala Ile Tyr His Pro Gln Gln Phe Val Tyr Ala Gly Ala Met
            180                 185                 190

Ser Gly Leu Leu Asp Pro Ser Gln Ala Met Gly Pro Thr Leu Ile Gly
        195                 200                 205

Leu Ala Met Gly Asp Ala Gly Gly Tyr Lys Ala Ser Asp Met Trp Gly
    210                 215                 220

Pro Lys Glu Asp Pro Ala Trp Gln Arg Asn Asp Pro Leu Leu Asn Val
225                 230                 235                 240
```

```
Gly Lys Leu Ile Ala Asn Asn Thr Arg Val Trp Val Tyr Cys Gly Asn
            245                 250                 255
Gly Lys Pro Ser Asp Leu Gly Gly Asn Asn Leu Pro Ala Lys Phe Leu
            260                 265                 270
Glu Gly Phe Val Arg Thr Ser Asn Ile Lys Phe Gln Asp Ala Tyr Asn
            275                 280                 285
Ala Gly Gly His Asn Gly Val Phe Asp Phe Pro Asp Ser Gly Thr
            290                 295                 300
His Ser Trp Glu Tyr Trp Gly Ala Gln Leu Asn Ala Met Lys Pro Asp
305                 310                 315                 320
Leu Gln Arg Ala Leu Gly Ala Thr Pro Asn Thr Gly Pro Ala Pro Gln
                325                 330                 335
Gly Ala

<210> SEQ ID NO 8
<211> LENGTH: 325
<212> TYPE: PRT
<213> ORGANISM: Mycobacterium tuberculosis
<220> FEATURE:
<221> NAME/KEY: misc_feature
<223> OTHER INFORMATION: FbpB or Ag85B

<400> SEQUENCE: 8

Met Thr Asp Val Ser Arg Lys Ile Arg Ala Trp Gly Arg Arg Leu Met
1               5                   10                  15
Ile Gly Thr Ala Ala Ala Val Val Leu Pro Gly Leu Val Gly Leu Ala
            20                  25                  30
Gly Gly Ala Ala Thr Ala Gly Ala Phe Ser Arg Pro Gly Leu Pro Val
        35                  40                  45
Glu Tyr Leu Gln Val Pro Ser Pro Ser Met Gly Arg Asp Ile Lys Val
    50                  55                  60
Gln Phe Gln Ser Gly Gly Asn Asn Ser Pro Ala Val Tyr Leu Leu Asp
65                  70                  75                  80
Gly Leu Arg Ala Gln Asp Asp Tyr Asn Gly Trp Asp Ile Asn Thr Pro
                85                  90                  95
Ala Phe Glu Trp Tyr Tyr Gln Ser Gly Leu Ser Ile Val Met Pro Val
            100                 105                 110
Gly Gly Gln Ser Ser Phe Tyr Ser Asp Trp Tyr Ser Pro Ala Cys Gly
        115                 120                 125
Lys Ala Gly Cys Gln Thr Tyr Lys Trp Glu Thr Phe Leu Thr Ser Glu
    130                 135                 140
Leu Pro Gln Trp Leu Ser Ala Asn Arg Ala Val Lys Pro Thr Gly Ser
145                 150                 155                 160
Ala Ala Ile Gly Leu Ser Met Ala Gly Ser Ser Ala Met Ile Leu Ala
                165                 170                 175
Ala Tyr His Pro Gln Gln Phe Ile Tyr Ala Gly Ser Leu Ser Ala Leu
            180                 185                 190
Leu Asp Pro Ser Gln Gly Met Gly Pro Ser Leu Ile Gly Leu Ala Met
        195                 200                 205
Gly Asp Ala Gly Gly Tyr Lys Ala Ala Asp Met Trp Gly Pro Ser Ser
    210                 215                 220
Asp Pro Ala Trp Glu Arg Asn Asp Pro Thr Gln Gln Ile Pro Lys Leu
225                 230                 235                 240
Val Ala Asn Asn Thr Arg Leu Trp Val Tyr Cys Gly Asn Gly Thr Pro
                245                 250                 255
```

```
Asn Glu Leu Gly Gly Ala Asn Ile Pro Ala Glu Phe Leu Glu Asn Phe
            260                 265                 270

Val Arg Ser Ser Asn Leu Lys Phe Gln Asp Ala Tyr Asn Ala Ala Gly
        275                 280                 285

Gly His Asn Ala Val Phe Asn Phe Pro Pro Asn Gly Thr His Ser Trp
        290                 295                 300

Glu Tyr Trp Gly Ala Gln Leu Asn Ala Met Lys Gly Asp Leu Gln Ser
305                 310                 315                 320

Ser Leu Gly Ala Gly
                325

<210> SEQ ID NO 9
<211> LENGTH: 741
<212> TYPE: PRT
<213> ORGANISM: Mycobacterium tuberculosis
<220> FEATURE:
<221> NAME/KEY: misc_feature
<223> OTHER INFORMATION: GlcB

<400> SEQUENCE: 9

Met Thr Asp Arg Val Ser Val Gly Asn Leu Arg Ile Ala Arg Val Leu
1               5                   10                  15

Tyr Asp Phe Val Asn Asn Glu Ala Leu Pro Gly Thr Asp Ile Asp Pro
            20                  25                  30

Asp Ser Phe Trp Ala Gly Val Asp Lys Val Val Ala Asp Leu Thr Pro
        35                  40                  45

Gln Asn Gln Ala Leu Leu Asn Ala Arg Asp Glu Leu Gln Ala Gln Ile
    50                  55                  60

Asp Lys Trp His Arg Arg Arg Val Ile Glu Pro Ile Asp Met Asp Ala
65                  70                  75                  80

Tyr Arg Gln Phe Leu Thr Glu Ile Gly Tyr Leu Leu Pro Glu Pro Asp
                85                  90                  95

Asp Phe Thr Ile Thr Thr Ser Gly Val Asp Ala Glu Ile Thr Thr Thr
            100                 105                 110

Ala Gly Pro Gln Leu Val Val Pro Val Leu Asn Ala Arg Phe Ala Leu
        115                 120                 125

Asn Ala Ala Asn Ala Arg Trp Gly Ser Leu Tyr Asp Ala Leu Tyr Gly
    130                 135                 140

Thr Asp Val Ile Pro Glu Thr Asp Gly Ala Glu Lys Gly Pro Thr Tyr
145                 150                 155                 160

Asn Lys Val Arg Gly Asp Lys Val Ile Ala Tyr Ala Arg Lys Phe Leu
                165                 170                 175

Asp Asp Ser Val Pro Leu Ser Ser Gly Ser Phe Gly Asp Ala Thr Gly
            180                 185                 190

Phe Thr Val Gln Asp Gly Gln Leu Val Val Ala Leu Pro Asp Lys Ser
        195                 200                 205

Thr Gly Leu Ala Asn Pro Gly Gln Phe Ala Gly Tyr Thr Gly Ala Ala
    210                 215                 220

Glu Ser Pro Thr Ser Val Leu Leu Ile Asn His Gly Leu His Ile Glu
225                 230                 235                 240

Ile Leu Ile Asp Pro Glu Ser Gln Val Gly Thr Thr Asp Arg Ala Gly
                245                 250                 255

Val Lys Asp Val Ile Leu Glu Ser Ala Ile Thr Thr Ile Met Asp Phe
            260                 265                 270

Glu Asp Ser Val Ala Ala Val Asp Ala Ala Asp Lys Val Leu Gly Tyr
```

-continued

```
            275                 280                 285
Arg Asn Trp Leu Gly Leu Asn Lys Gly Asp Leu Ala Ala Ala Val Asp
    290                 295                 300
Lys Asp Gly Thr Ala Phe Leu Arg Val Leu Asn Arg Asp Arg Asn Tyr
305                 310                 315                 320
Thr Ala Pro Gly Gly Gly Gln Phe Thr Leu Pro Gly Arg Ser Leu Met
                325                 330                 335
Phe Val Arg Asn Val Gly His Leu Met Thr Asn Asp Ala Ile Val Asp
                340                 345                 350
Thr Asp Gly Ser Glu Val Phe Glu Gly Ile Met Asp Ala Leu Phe Thr
            355                 360                 365
Gly Leu Ile Ala Ile His Gly Leu Lys Ala Ser Asp Val Asn Gly Pro
    370                 375                 380
Leu Ile Asn Ser Arg Thr Gly Ser Ile Tyr Ile Val Lys Pro Lys Met
385                 390                 395                 400
His Gly Pro Ala Glu Val Ala Phe Thr Cys Glu Leu Phe Ser Arg Val
                405                 410                 415
Glu Asp Val Leu Gly Leu Pro Gln Asn Thr Met Lys Ile Gly Ile Met
                420                 425                 430
Asp Glu Glu Arg Arg Thr Thr Val Asn Leu Lys Ala Cys Ile Lys Ala
            435                 440                 445
Ala Ala Asp Arg Val Val Phe Ile Asn Thr Gly Phe Leu Asp Arg Thr
    450                 455                 460
Gly Asp Glu Ile His Thr Ser Met Glu Ala Gly Pro Met Val Arg Lys
465                 470                 475                 480
Gly Thr Met Lys Ser Gln Pro Trp Ile Leu Ala Tyr Glu Asp His Asn
                485                 490                 495
Val Asp Ala Gly Leu Ala Ala Gly Phe Ser Gly Arg Ala Gln Val Gly
                500                 505                 510
Lys Gly Met Trp Thr Met Thr Glu Leu Met Ala Asp Met Val Glu Thr
            515                 520                 525
Lys Ile Ala Gln Pro Arg Ala Gly Ala Ser Thr Ala Trp Val Pro Ser
    530                 535                 540
Pro Thr Ala Ala Thr Leu His Ala Leu His Tyr His Gln Val Asp Val
545                 550                 555                 560
Ala Ala Val Gln Gln Gly Leu Ala Gly Lys Arg Ala Thr Ile Glu
                565                 570                 575
Gln Leu Leu Thr Ile Pro Leu Ala Lys Glu Leu Ala Trp Ala Pro Asp
                580                 585                 590
Glu Ile Arg Glu Glu Val Asp Asn Asn Cys Gln Ser Ile Leu Gly Tyr
            595                 600                 605
Val Val Arg Trp Val Asp Gln Gly Val Gly Cys Ser Lys Val Pro Asp
    610                 615                 620
Ile His Asp Val Ala Leu Met Glu Asp Arg Ala Thr Leu Arg Ile Ser
625                 630                 635                 640
Ser Gln Leu Leu Ala Asn Trp Leu Arg His Gly Val Ile Thr Ser Ala
                645                 650                 655
Asp Val Arg Ala Ser Leu Glu Arg Met Ala Pro Leu Val Asp Arg Gln
                660                 665                 670
Asn Ala Gly Asp Val Ala Tyr Arg Pro Met Ala Pro Asn Phe Asp Asp
            675                 680                 685
Ser Ile Ala Phe Leu Ala Ala Gln Glu Leu Ile Leu Ser Gly Ala Gln
    690                 695                 700
```

```
Gln Pro Asn Gly Tyr Thr Glu Pro Ile Leu His Arg Arg Arg Glu
705                 710                 715                 720

Phe Lys Ala Arg Ala Ala Glu Lys Pro Ala Pro Ser Asp Arg Ala Gly
                725                 730                 735

Asp Asp Ala Ala Arg
            740

<210> SEQ ID NO 10
<211> LENGTH: 460
<212> TYPE: PRT
<213> ORGANISM: Mycobacterium tuberculosis
<220> FEATURE:
<221> NAME/KEY: misc_feature
<223> OTHER INFORMATION: Hypothetical Ala/Gly- Rich protein

<400> SEQUENCE: 10

Met Thr Gln Ser Gln Thr Val Thr Val Asp Gln Gln Glu Ile Leu Asn
1               5                   10                  15

Arg Ala Asn Glu Val Glu Ala Pro Met Ala Asp Pro Pro Thr Asp Val
                20                  25                  30

Pro Ile Thr Pro Cys Glu Leu Thr Ala Ala Lys Asn Ala Ala Gln Gln
            35                  40                  45

Leu Val Leu Ser Ala Asp Asn Met Arg Glu Tyr Leu Ala Ala Gly Ala
        50                  55                  60

Lys Glu Arg Gln Arg Leu Ala Thr Ser Leu Arg Asn Ala Ala Lys Ala
65                  70                  75                  80

Tyr Gly Glu Val Asp Glu Ala Ala Thr Ala Leu Asp Asn Asp Gly
                85                  90                  95

Glu Gly Thr Val Gln Ala Glu Ser Ala Gly Ala Val Gly Gly Asp Ser
            100                 105                 110

Ser Ala Glu Leu Thr Asp Thr Pro Arg Val Ala Thr Ala Gly Glu Pro
        115                 120                 125

Asn Phe Met Asp Leu Lys Glu Ala Ala Arg Lys Leu Glu Thr Gly Asp
    130                 135                 140

Gln Gly Ala Ser Leu Ala His Phe Ala Asp Gly Trp Asn Thr Phe Asn
145                 150                 155                 160

Leu Thr Leu Gln Gly Asp Val Lys Arg Phe Arg Gly Phe Asp Asn Trp
                165                 170                 175

Glu Gly Asp Ala Ala Thr Ala Cys Glu Ala Ser Leu Asp Gln Gln Arg
            180                 185                 190

Gln Trp Ile Leu His Met Ala Lys Leu Ser Ala Ala Met Ala Lys Gln
        195                 200                 205

Ala Gln Tyr Val Ala Gln Leu His Val Trp Ala Arg Arg Glu His Pro
    210                 215                 220

Thr Tyr Glu Asp Ile Val Gly Leu Glu Arg Leu Tyr Ala Glu Asn Pro
225                 230                 235                 240

Ser Ala Arg Asp Gln Ile Leu Pro Val Tyr Ala Glu Tyr Gln Gln Arg
                245                 250                 255

Ser Glu Lys Val Leu Thr Glu Tyr Asn Asn Lys Ala Ala Leu Glu Pro
            260                 265                 270

Val Asn Pro Pro Lys Pro Pro Ala Ile Lys Ile Asp Pro Pro
        275                 280                 285

Pro Pro Gln Glu Gln Gly Leu Ile Pro Gly Phe Leu Met Pro Pro Ser
    290                 295                 300

Asp Gly Ser Gly Val Thr Pro Gly Thr Gly Met Pro Ala Ala Pro Met
```

```
                305                 310                 315                 320
Val Pro Pro Thr Gly Ser Pro Gly Gly Gly Leu Pro Ala Asp Thr Ala
                    325                 330                 335

Ala Gln Leu Thr Ser Ala Gly Arg Glu Ala Ala Ala Leu Ser Gly Asp
                340                 345                 350

Val Ala Val Lys Ala Ala Ser Leu Gly Gly Gly Gly Gly Gly Gly Val
                355                 360                 365

Pro Ser Ala Pro Leu Gly Ser Ala Ile Gly Gly Ala Glu Ser Val Arg
            370                 375                 380

Pro Ala Gly Ala Gly Asp Ile Ala Gly Leu Gly Gln Gly Arg Ala Gly
385                 390                 395                 400

Gly Gly Ala Ala Leu Gly Gly Gly Met Gly Met Pro Met Gly Ala
                405                 410                 415

Ala His Gln Gly Gln Gly Gly Ala Lys Ser Lys Gly Ser Gln Gln Glu
                420                 425                 430

Asp Glu Ala Leu Tyr Thr Glu Asp Arg Ala Trp Thr Glu Ala Val Ile
                435                 440                 445

Gly Asn Arg Arg Arg Gln Asp Ser Lys Glu Ser Lys
            450                 455                 460

<210> SEQ ID NO 11
<211> LENGTH: 71
<212> TYPE: PRT
<213> ORGANISM: Mycobacterium tuberculosis
<220> FEATURE:
<221> NAME/KEY: misc_feature
<223> OTHER INFORMATION: SecE2

<400> SEQUENCE: 11

Met Ser Val Tyr Lys Val Ile Asp Ile Ile Gly Thr Ser Pro Thr Ser
1               5                   10                  15

Trp Glu Gln Ala Ala Ala Glu Ala Val Gln Arg Ala Arg Asp Ser Val
                20                  25                  30

Asp Asp Ile Arg Val Ala Arg Val Ile Glu Gln Asp Met Ala Val Asp
            35                  40                  45

Ser Ala Gly Lys Ile Thr Tyr Arg Ile Lys Leu Glu Val Ser Phe Lys
        50                  55                  60

Met Arg Pro Ala Gln Pro Arg
65                  70

<210> SEQ ID NO 12
<211> LENGTH: 228
<212> TYPE: PRT
<213> ORGANISM: Mycobacterium tuberculosis
<220> FEATURE:
<221> NAME/KEY: misc_feature
<223> OTHER INFORMATION: MPT64

<400> SEQUENCE: 12

Val Arg Ile Lys Ile Phe Met Leu Val Thr Ala Val Val Leu Leu Cys
1               5                   10                  15

Cys Ser Gly Val Ala Thr Ala Ala Pro Lys Thr Tyr Cys Glu Glu Leu
                20                  25                  30

Lys Gly Thr Asp Thr Gly Gln Ala Cys Gln Ile Gln Met Ser Asp Pro
            35                  40                  45

Ala Tyr Asn Ile Asn Ile Ser Leu Pro Ser Tyr Tyr Pro Asp Gln Lys
        50                  55                  60

Ser Leu Glu Asn Tyr Ile Ala Gln Thr Arg Asp Lys Phe Leu Ser Ala
```

```
                65                  70                  75                  80
Ala Thr Ser Ser Thr Pro Arg Glu Ala Pro Tyr Glu Leu Asn Ile Thr
                        85                  90                  95

Ser Ala Thr Tyr Gln Ser Ala Ile Pro Pro Arg Gly Thr Gln Ala Val
                100                 105                 110

Val Leu Lys Val Tyr Gln Asn Ala Gly Gly Thr His Pro Thr Thr Thr
                115                 120                 125

Tyr Lys Ala Phe Asp Trp Asp Gln Ala Tyr Arg Lys Pro Ile Thr Tyr
            130                 135                 140

Asp Thr Leu Trp Gln Ala Asp Thr Asp Pro Leu Pro Val Val Phe Pro
145                 150                 155                 160

Ile Val Gln Gly Glu Leu Ser Lys Gln Thr Gly Gln Gln Val Ser Ile
                165                 170                 175

Ala Pro Asn Ala Gly Leu Asp Pro Val Asn Tyr Gln Asn Phe Ala Val
                180                 185                 190

Thr Asn Asp Gly Val Ile Phe Phe Phe Asn Pro Gly Glu Leu Leu Pro
                195                 200                 205

Glu Ala Ala Gly Pro Thr Gln Val Leu Val Pro Arg Ser Ala Ile Asp
            210                 215                 220

Ser Met Leu Ala
225

<210> SEQ ID NO 13
<211> LENGTH: 144
<212> TYPE: PRT
<213> ORGANISM: Mycobacterium tuberculosis
<220> FEATURE:
<221> NAME/KEY: misc_feature
<223> OTHER INFORMATION: HspX

<400> SEQUENCE: 13

Met Ala Thr Thr Leu Pro Val Gln Arg His Pro Arg Ser Leu Phe Pro
1               5                   10                  15

Glu Phe Ser Glu Leu Phe Ala Ala Phe Pro Ser Phe Ala Gly Leu Arg
                20                  25                  30

Pro Thr Phe Asp Thr Arg Leu Met Arg Leu Glu Asp Glu Met Lys Glu
            35                  40                  45

Gly Arg Tyr Glu Val Arg Ala Glu Leu Pro Gly Val Asp Pro Asp Lys
        50                  55                  60

Asp Val Asp Ile Met Val Arg Asp Gly Gln Leu Thr Ile Lys Ala Glu
65                  70                  75                  80

Arg Thr Glu Gln Lys Asp Phe Asp Gly Arg Ser Glu Phe Ala Tyr Gly
                85                  90                  95

Ser Phe Val Arg Thr Val Ser Leu Pro Val Gly Ala Asp Glu Asp Asp
                100                 105                 110

Ile Lys Ala Thr Tyr Asp Lys Gly Ile Leu Thr Val Ser Val Ala Val
            115                 120                 125

Ser Glu Gly Lys Pro Thr Glu Lys His Ile Gln Ile Arg Ser Thr Asn
        130                 135                 140

<210> SEQ ID NO 14
<211> LENGTH: 159
<212> TYPE: PRT
<213> ORGANISM: Mycobacterium tuberculosis
<220> FEATURE:
<221> NAME/KEY: misc_feature
<223> OTHER INFORMATION: LpqH
```

```
<400> SEQUENCE: 14

Val Lys Arg Gly Leu Thr Val Ala Val Ala Gly Ala Ala Ile Leu Val
1               5                   10                  15

Ala Gly Leu Ser Gly Cys Ser Ser Asn Lys Ser Thr Thr Gly Ser Gly
            20                  25                  30

Glu Thr Thr Thr Ala Ala Gly Thr Thr Ala Ser Pro Gly Ala Ala Ser
        35                  40                  45

Gly Pro Lys Val Val Ile Asp Gly Lys Asp Gln Asn Val Thr Gly Ser
    50                  55                  60

Val Val Cys Thr Thr Ala Ala Gly Asn Val Asn Ile Ala Ile Gly Gly
65                  70                  75                  80

Ala Ala Thr Gly Ile Ala Ala Val Leu Thr Asp Gly Asn Pro Pro Glu
                85                  90                  95

Val Lys Ser Val Gly Leu Gly Asn Val Asn Gly Val Thr Leu Gly Tyr
            100                 105                 110

Thr Ser Gly Thr Gly Gln Gly Asn Ala Ser Ala Thr Lys Asp Gly Ser
            115                 120                 125

His Tyr Lys Ile Thr Gly Thr Ala Thr Gly Val Asp Met Ala Asn Pro
    130                 135                 140

Met Ser Pro Val Asn Lys Ser Phe Glu Ile Glu Val Thr Cys Ser
145                 150                 155

<210> SEQ ID NO 15
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-1

<400> SEQUENCE: 15

Met Trp Thr Thr Arg Leu Val Arg Ser Gly Leu Ala Ala Leu Cys Ala
1               5                   10                  15

Ala Val Leu Val
            20

<210> SEQ ID NO 16
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-2

<400> SEQUENCE: 16

Leu Ala Ala Leu Cys Ala Ala Val Leu Val Ser Ser Gly Cys Ala Arg
1               5                   10                  15

Phe Asn Asp Ala
            20

<210> SEQ ID NO 17
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
```

```
<223> OTHER INFORMATION: LppZ-3

<400> SEQUENCE: 17

Ser Ser Gly Cys Ala Arg Phe Asn Asp Ala Gln Ser Gln Pro Phe Thr
1               5                   10                  15

Thr Glu Pro Glu
            20

<210> SEQ ID NO 18
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-4

<400> SEQUENCE: 18

Gln Ser Gln Pro Phe Thr Thr Glu Pro Glu Leu Arg Pro Gln Pro Ser
1               5                   10                  15

Ser Thr Pro Pro
            20

<210> SEQ ID NO 19
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-5

<400> SEQUENCE: 19

Leu Arg Pro Gln Pro Ser Ser Thr Pro Pro Pro Pro Pro Leu Pro
1               5                   10                  15

Pro Val Pro Phe
            20

<210> SEQ ID NO 20
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-6

<400> SEQUENCE: 20

Pro Pro Pro Pro Leu Pro Pro Val Pro Phe Pro Lys Glu Cys Pro Ala
1               5                   10                  15

Pro Gly Val Met
            20

<210> SEQ ID NO 21
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-7

<400> SEQUENCE: 21
```

```
Pro Lys Glu Cys Pro Ala Pro Gly Val Met Gln Gly Cys Leu Glu Ser
1               5                   10                  15

Thr Ser Gly Leu
            20
```

<210> SEQ ID NO 22
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-8

<400> SEQUENCE: 22

```
Gln Gly Cys Leu Glu Ser Thr Ser Gly Leu Ile Met Gly Ile Asp Ser
1               5                   10                  15

Lys Thr Ala Leu
            20
```

<210> SEQ ID NO 23
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-9

<400> SEQUENCE: 23

```
Ile Met Gly Ile Asp Ser Lys Thr Ala Leu Val Ala Glu Arg Ile Thr
1               5                   10                  15

Gly Ala Val Glu
            20
```

<210> SEQ ID NO 24
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-10

<400> SEQUENCE: 24

```
Val Ala Glu Arg Ile Thr Gly Ala Val Glu Glu Ile Ser Ile Ser Ala
1               5                   10                  15

Glu Pro Lys Val
            20
```

<210> SEQ ID NO 25
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-11

<400> SEQUENCE: 25

```
Glu Ile Ser Ile Ser Ala Glu Pro Lys Val Lys Thr Val Ile Pro Val
1               5                   10                  15
```

```
Asp Pro Ala Gly
            20

<210> SEQ ID NO 26
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-12

<400> SEQUENCE: 26

Lys Thr Val Ile Pro Val Asp Pro Ala Gly Asp Gly Gly Leu Met Asp
1               5                  10                  15

Ile Val Leu Ser
            20

<210> SEQ ID NO 27
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-13

<400> SEQUENCE: 27

Asp Gly Gly Leu Met Asp Ile Val Leu Ser Pro Thr Tyr Ser Gln Asp
1               5                  10                  15

Arg Leu Met Tyr
            20

<210> SEQ ID NO 28
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-14

<400> SEQUENCE: 28

Pro Thr Tyr Ser Gln Asp Arg Leu Met Tyr Ala Tyr Ile Ser Thr Pro
1               5                  10                  15

Thr Asp Asn Arg
            20

<210> SEQ ID NO 29
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-15

<400> SEQUENCE: 29

Ala Tyr Ile Ser Thr Pro Thr Asp Asn Arg Val Val Arg Val Ala Asp
1               5                  10                  15

Gly Asp Ile Pro
            20
```

```
<210> SEQ ID NO 30
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-16

<400> SEQUENCE: 30

Val Val Arg Val Ala Asp Gly Asp Ile Pro Lys Asp Ile Leu Thr Gly
1               5                   10                  15

Ile Pro Lys Gly
            20

<210> SEQ ID NO 31
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-17

<400> SEQUENCE: 31

Lys Asp Ile Leu Thr Gly Ile Pro Lys Gly Ala Ala Gly Asn Thr Gly
1               5                   10                  15

Ala Leu Ile Phe
            20

<210> SEQ ID NO 32
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-18

<400> SEQUENCE: 32

Ala Ala Gly Asn Thr Gly Ala Leu Ile Phe Thr Ser Pro Thr Thr Leu
1               5                   10                  15

Val Val Met Thr
            20

<210> SEQ ID NO 33
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-19

<400> SEQUENCE: 33

Thr Ser Pro Thr Thr Leu Val Val Met Thr Gly Asp Ala Gly Asp Pro
1               5                   10                  15

Ala Leu Ala Ala
            20

<210> SEQ ID NO 34
```

```
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-20

<400> SEQUENCE: 34

Gly Asp Ala Gly Asp Pro Ala Leu Ala Ala Asp Pro Gln Ser Leu Ala
1               5                   10                  15

Gly Lys Val Leu
            20

<210> SEQ ID NO 35
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-21

<400> SEQUENCE: 35

Asp Pro Gln Ser Leu Ala Gly Lys Val Leu Arg Ile Glu Gln Pro Thr
1               5                   10                  15

Thr Ile Gly Gln
            20

<210> SEQ ID NO 36
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-22

<400> SEQUENCE: 36

Arg Ile Glu Gln Pro Thr Thr Ile Gly Gln Thr Pro Pro Thr Thr Ala
1               5                   10                  15

Leu Ser Gly Ile
            20

<210> SEQ ID NO 37
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-23

<400> SEQUENCE: 37

Thr Pro Pro Thr Thr Ala Leu Ser Gly Ile Gly Ser Gly Gly Gly Leu
1               5                   10                  15

Cys Ile Asp Pro
            20

<210> SEQ ID NO 38
<211> LENGTH: 20
<212> TYPE: PRT
<213> ORGANISM: Artificial Sequence
```

```
<220> FEATURE:
<223> OTHER INFORMATION: synthetic
<220> FEATURE:
<221> NAME/KEY: misc_feature
<223> OTHER INFORMATION: LppZ-24

<400> SEQUENCE: 38

Gly Ser Gly Gly Gly Leu Cys Ile Asp Pro Val Asp Gly Ser Leu Tyr
1               5                   10                  15

Val Ala Asp Arg
            20

<210> SEQ ID NO 39
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-25

<400> SEQUENCE: 39

Val Asp Gly Ser Leu Tyr Val Ala Asp Arg Thr Pro Thr Ala Asp Arg
1               5                   10                  15

Leu Gln Arg Ile
            20

<210> SEQ ID NO 40
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-26

<400> SEQUENCE: 40

Thr Pro Thr Ala Asp Arg Leu Gln Arg Ile Thr Lys Asn Ser Glu Val
1               5                   10                  15

Ser Thr Val Trp
            20

<210> SEQ ID NO 41
<211> LENGTH: 20
<212> TYPE: PRT
<213> ORGANISM: Artificial Sequence
<220> FEATURE:
<223> OTHER INFORMATION: synthetic

<400> SEQUENCE: 41

Thr Lys Asn Ser Glu Val Ser Thr Val Trp Thr Trp Pro Asp Lys Pro
1               5                   10                  15

Gly Val Ala Gly
            20

<210> SEQ ID NO 42
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-28
```

```
<400> SEQUENCE: 42

Thr Trp Pro Asp Lys Pro Gly Val Ala Gly Cys Ala Ala Met Asp Gly
1               5                   10                  15

Thr Val Leu Val
            20

<210> SEQ ID NO 43
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-29

<400> SEQUENCE: 43

Cys Ala Ala Met Asp Gly Thr Val Leu Val Asn Leu Ile Asn Thr Lys
1               5                   10                  15

Leu Thr Val Ala
            20

<210> SEQ ID NO 44
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-30

<400> SEQUENCE: 44

Asn Leu Ile Asn Thr Lys Leu Thr Val Ala Val Arg Leu Ala Pro Ser
1               5                   10                  15

Thr Gly Ala Val
            20

<210> SEQ ID NO 45
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-31

<400> SEQUENCE: 45

Val Arg Leu Ala Pro Ser Thr Gly Ala Val Thr Gly Glu Pro Asp Val
1               5                   10                  15

Val Arg Lys Asp
            20

<210> SEQ ID NO 46
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-32

<400> SEQUENCE: 46

Thr Gly Glu Pro Asp Val Val Arg Lys Asp Thr His Ala His Ala Trp
```

-continued

```
                1               5                  10                 15
Ala Leu Arg Met
            20

<210> SEQ ID NO 47
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-33

<400> SEQUENCE: 47

Thr His Ala His Ala Trp Ala Leu Arg Met Ser Pro Asp Gly Asn Val
1               5                   10                  15

Trp Gly Ala Thr
            20

<210> SEQ ID NO 48
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-34

<400> SEQUENCE: 48

Ser Pro Asp Gly Asn Val Trp Gly Ala Thr Val Asn Lys Thr Ala Gly
1               5                   10                  15

Asp Ala Glu Lys
            20

<210> SEQ ID NO 49
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-35

<400> SEQUENCE: 49

Val Asn Lys Thr Ala Gly Asp Ala Glu Lys Leu Asp Asp Val Val Phe
1               5                   10                  15

Pro Leu Phe Pro
            20

<210> SEQ ID NO 50
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-36

<400> SEQUENCE: 50

Leu Asp Asp Val Val Phe Pro Leu Phe Pro Gln Gly Gly Gly Phe Pro
1               5                   10                  15

Arg Asn Asn Asp
```

```
<210> SEQ ID NO 51
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: LppZ-37

<400> SEQUENCE: 51

Val Val Phe Pro Leu Phe Pro Gln Gly Gly Gly Phe Pro Arg Asn Asn
1               5                   10                  15

Asp Asp Lys Thr
            20

<210> SEQ ID NO 52
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-1

<400> SEQUENCE: 52

Met Met Pro Lys Pro Ala Asp His Arg Asn His Ala Ala Val Ser Thr
1               5                   10                  15

Ser Val Leu Ser Ala
            20

<210> SEQ ID NO 53
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-2

<400> SEQUENCE: 53

Leu Ala Ala Val Ser Thr Ser Val Leu Ser Ala Leu Phe Leu Gly Ala
1               5                   10                  15

Gly Ala Ala Leu Leu
            20

<210> SEQ ID NO 54
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-3

<400> SEQUENCE: 54

Ser Leu Phe Leu Gly Ala Gly Ala Ala Leu Leu Ser Ala Cys Ser Ser
1               5                   10                  15

Pro Gln His Ala Ser
            20
```

```
<210> SEQ ID NO 55
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-4

<400> SEQUENCE: 55

Gln Ser Ala Cys Ser Ser Pro Gln His Ala Ser Thr Val Pro Gly Thr
1               5                   10                  15

Thr Pro Ser Ile Trp
            20

<210> SEQ ID NO 56
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-5

<400> SEQUENCE: 56

Leu Thr Val Pro Gly Thr Thr Pro Ser Ile Trp Thr Gly Ser Pro Ala
1               5                   10                  15

Pro Ser Gly Leu Ser
            20

<210> SEQ ID NO 57
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-6

<400> SEQUENCE: 57

Pro Thr Gly Ser Pro Ala Pro Ser Gly Leu Ser Gly His Asp Glu Glu
1               5                   10                  15

Ser Pro Gly Ala Gln
            20

<210> SEQ ID NO 58
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-7

<400> SEQUENCE: 58

Pro Gly His Asp Glu Glu Ser Pro Gly Ala Gln Ser Leu Thr Ser Thr
1               5                   10                  15

Leu Thr Ala Pro Asp
            20

<210> SEQ ID NO 59
<211> LENGTH: 21
<212> TYPE: PRT
```

<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-8

<400> SEQUENCE: 59

Gln Ser Leu Thr Ser Thr Leu Thr Ala Pro Asp Gly Thr Lys Val Ala
1               5                   10                  15

Thr Ala Lys Phe Glu
            20

<210> SEQ ID NO 60
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-9

<400> SEQUENCE: 60

Ile Gly Thr Lys Val Ala Thr Ala Lys Phe Glu Phe Ala Asn Gly Tyr
1               5                   10                  15

Ala Thr Val Thr Ile
            20

<210> SEQ ID NO 61
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-10

<400> SEQUENCE: 61

Val Phe Ala Asn Gly Tyr Ala Thr Val Thr Ile Ala Thr Thr Gly Val
1               5                   10                  15

Gly Lys Leu Thr Pro
            20

<210> SEQ ID NO 62
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-11

<400> SEQUENCE: 62

Glu Ala Thr Thr Gly Val Gly Lys Leu Thr Pro Gly Phe His Gly Leu
1               5                   10                  15

His Ile His Gln Val
            20

<210> SEQ ID NO 63
<211> LENGTH: 21
<212> TYPE: PRT
<213> ORGANISM: Artificial Sequence
<220> FEATURE:
<223> OTHER INFORMATION: synthetic

```
<220> FEATURE:
<221> NAME/KEY: misc_feature
<223> OTHER INFORMATION: SodC-12

<400> SEQUENCE: 63

Lys Gly Phe His Gly Leu His Ile His Gln Val Gly Lys Cys Glu Pro
 1               5                  10                  15

Asn Ser Val Ala Pro
             20

<210> SEQ ID NO 64
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-13

<400> SEQUENCE: 64

Asp Gly Lys Cys Glu Pro Asn Ser Val Ala Pro Thr Gly Gly Ala Pro
 1               5                  10                  15

Gly Asn Phe Leu Ser
             20

<210> SEQ ID NO 65
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-14

<400> SEQUENCE: 65

Pro Thr Gly Gly Ala Pro Gly Asn Phe Leu Ser Ala Gly Gly His Tyr
 1               5                  10                  15

His Val Pro Gly His
             20

<210> SEQ ID NO 66
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-15

<400> SEQUENCE: 66

Ala Ala Gly Gly His Tyr His Val Pro Gly His Thr Gly Thr Pro Ala
 1               5                  10                  15

Ser Gly Asp Leu Ala
             20

<210> SEQ ID NO 67
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-16
```

<400> SEQUENCE: 67

Val Thr Gly Thr Pro Ala Ser Gly Asp Leu Ala Ser Leu Gln Val Arg
1               5                   10                  15

Gly Asp Gly Ser Ala
            20

<210> SEQ ID NO 68
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-17

<400> SEQUENCE: 68

Lys Ser Leu Gln Val Arg Gly Asp Gly Ser Ala Met Leu Val Thr Thr
1               5                   10                  15

Thr Asp Ala Phe Thr
            20

<210> SEQ ID NO 69
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-18

<400> SEQUENCE: 69

Ala Met Leu Val Thr Thr Thr Asp Ala Phe Thr Met Asp Asp Leu Leu
1               5                   10                  15

Ser Gly Ala Lys Thr
            20

<210> SEQ ID NO 70
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-19

<400> SEQUENCE: 70

Thr Met Asp Asp Leu Leu Ser Gly Ala Lys Thr Ala Ile Ile Ile His
1               5                   10                  15

Ala Gly Ala Asp Asn
            20

<210> SEQ ID NO 71
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-20

<400> SEQUENCE: 71

-continued

Gly Ala Ile Ile Ile His Ala Gly Ala Asp Asn Phe Ala Asn Ile Pro
1               5                   10                  15

Pro Glu Arg Tyr Val
            20

<210> SEQ ID NO 72
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-21

<400> SEQUENCE: 72

Arg Gln Val Asn Gly Thr Pro Gly Pro Asp Glu Thr Thr Leu Thr Thr
1               5                   10                  15

Gly Asp Ala Gly Lys
            20

<210> SEQ ID NO 73
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-22

<400> SEQUENCE: 73

Arg Gln Val Asn Gly Thr Pro Gly Pro Asp Glu Thr Thr Leu Thr Thr
1               5                   10                  15

Gly Asp Ala Gly Lys
            20

<210> SEQ ID NO 74
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: SodC-23

<400> SEQUENCE: 74

Thr Thr Thr Leu Thr Thr Gly Asp Ala Gly Lys Arg Val Ala Cys Gly
1               5                   10                  15

Val Ile Gly Ser Gly
            20

<210> SEQ ID NO 75
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: BfrB-1

<400> SEQUENCE: 75

Met Thr Glu Tyr Glu Gly Pro Lys Thr Lys Phe His Ala Leu Met Gln
1               5                   10                  15

-continued

```
Glu Gln Ile His
            20

<210> SEQ ID NO 76
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: BfrB-2

<400> SEQUENCE: 76

Phe His Ala Leu Met Gln Glu Gln Ile His Asn Glu Phe Thr Ala Ala
1               5                   10                  15

Gln Gln Tyr Val
            20

<210> SEQ ID NO 77
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: BfrB-3

<400> SEQUENCE: 77

Asn Glu Phe Thr Ala Ala Gln Gln Tyr Val Ala Ile Ala Val Tyr Phe
1               5                   10                  15

Asp Ser Glu Asp
            20

<210> SEQ ID NO 78
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: BfrB-4

<400> SEQUENCE: 78

Ala Ile Ala Val Tyr Phe Asp Ser Glu Asp Leu Pro Gln Leu Ala Lys
1               5                   10                  15

His Phe Tyr Ser
            20

<210> SEQ ID NO 79
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: BfrB-5

<400> SEQUENCE: 79

Leu Pro Gln Leu Ala Lys His Phe Tyr Ser Gln Ala Val Glu Glu Arg
1               5                   10                  15

Asn His Ala Met
            20
```

<210> SEQ ID NO 80
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: BfrB-6

<400> SEQUENCE: 80

Gln Ala Val Glu Glu Arg Asn His Ala Met Met Leu Val Gln His Leu
1               5                   10                  15

Leu Asp Arg Asp
            20

<210> SEQ ID NO 81
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: BfrB-7

<400> SEQUENCE: 81

Met Leu Val Gln His Leu Leu Asp Arg Asp Leu Arg Val Glu Ile Pro
1               5                   10                  15

Gly Val Asp Thr
            20

<210> SEQ ID NO 82
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: BfrB-8

<400> SEQUENCE: 82

Leu Arg Val Glu Ile Pro Gly Val Asp Thr Val Arg Asn Gln Phe Asp
1               5                   10                  15

Arg Pro Arg Glu
            20

<210> SEQ ID NO 83
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: BfrB-9

<400> SEQUENCE: 83

Val Arg Asn Gln Phe Asp Arg Pro Arg Glu Ala Leu Ala Leu Ala Leu
1               5                   10                  15

Asp Gln Glu Arg
            20

<210> SEQ ID NO 84
<211> LENGTH: 20

```
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: BfrB-10

<400> SEQUENCE: 84

Ala Leu Ala Leu Ala Leu Asp Gln Glu Arg Thr Val Thr Asp Gln Val
1               5                   10                  15

Gly Arg Leu Thr
            20

<210> SEQ ID NO 85
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: BfrB-11

<400> SEQUENCE: 85

Thr Val Thr Asp Gln Val Gly Arg Leu Thr Ala Val Ala Arg Asp Glu
1               5                   10                  15

Gly Asp Phe Leu
            20

<210> SEQ ID NO 86
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: BfrB-12

<400> SEQUENCE: 86

Ala Val Ala Arg Asp Glu Gly Asp Phe Leu Gly Glu Gln Phe Met Gln
1               5                   10                  15

Trp Phe Leu Gln
            20

<210> SEQ ID NO 87
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: BfrB-13

<400> SEQUENCE: 87

Gly Glu Gln Phe Met Gln Trp Phe Leu Gln Glu Gln Ile Glu Glu Val
1               5                   10                  15

Ala Leu Met Ala
            20

<210> SEQ ID NO 88
<211> LENGTH: 20
<212> TYPE: PRT
<213> ORGANISM: Artificial Sequence
<220> FEATURE:
```

```
<223> OTHER INFORMATION: synthetic
<220> FEATURE:
<221> NAME/KEY: misc_feature
<223> OTHER INFORMATION: BfrB-14

<400> SEQUENCE: 88

Glu Gln Ile Glu Glu Val Ala Leu Met Ala Thr Leu Val Arg Val Ala
1               5                   10                  15
Asp Arg Ala Gly
            20

<210> SEQ ID NO 89
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: BfrB-15

<400> SEQUENCE: 89

Thr Leu Val Arg Val Ala Asp Arg Ala Gly Ala Asn Leu Phe Glu Leu
1               5                   10                  15
Glu Asn Phe Val
            20

<210> SEQ ID NO 90
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: BfrB-16

<400> SEQUENCE: 90

Ala Asn Leu Phe Glu Leu Glu Asn Phe Val Ala Arg Glu Val Asp Val
1               5                   10                  15
Ala Pro Ala Ala
            20

<210> SEQ ID NO 91
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: BfrB-17

<400> SEQUENCE: 91

Ala Arg Glu Val Asp Val Ala Pro Ala Ala Ser Gly Ala Pro His Ala
1               5                   10                  15
Ala Gly Gly Arg
            20

<210> SEQ ID NO 92
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
```

```
<223> OTHER INFORMATION: BfrB-18

<400> SEQUENCE: 92

Arg Glu Val Asp Val Ala Pro Ala Ala Ser Gly Ala Pro His Ala Ala
1               5                   10                  15

Gly Gly Arg Leu
            20

<210> SEQ ID NO 93
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: TrxC-1

<400> SEQUENCE: 93

Met Thr Asp Ser Glu Lys Ser Ala Thr Ile Lys Val Thr Asp Ala Ser
1               5                   10                  15

Phe Ala Thr Asp
            20

<210> SEQ ID NO 94
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: TrxC-2

<400> SEQUENCE: 94

Lys Val Thr Asp Ala Ser Phe Ala Thr Asp Val Leu Ser Ser Asn Lys
1               5                   10                  15

Pro Val Leu Val
            20

<210> SEQ ID NO 95
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: TrxC-3

<400> SEQUENCE: 95

Val Leu Ser Ser Asn Lys Pro Val Leu Val Asp Phe Trp Ala Thr Trp
1               5                   10                  15

Cys Gly Pro Cys
            20

<210> SEQ ID NO 96
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: TrxC-4

<400> SEQUENCE: 96
```

```
Asp Phe Trp Ala Thr Trp Cys Gly Pro Cys Lys Met Val Ala Pro Val
1               5                  10                  15

Leu Glu Glu Ile
            20

<210> SEQ ID NO 97
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: TrxC-5

<400> SEQUENCE: 97

Lys Met Val Ala Pro Val Leu Glu Glu Ile Ala Thr Glu Arg Ala Thr
1               5                  10                  15

Asp Leu Thr Val
            20

<210> SEQ ID NO 98
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: TrxC-6

<400> SEQUENCE: 98

Ala Thr Glu Arg Ala Thr Asp Leu Thr Val Ala Lys Leu Asp Val Asp
1               5                  10                  15

Thr Asn Pro Glu
            20

<210> SEQ ID NO 99
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: TrxC-7

<400> SEQUENCE: 99

Ala Lys Leu Asp Val Asp Thr Asn Pro Glu Thr Ala Arg Asn Phe Gln
1               5                  10                  15

Val Val Ser Ile
            20

<210> SEQ ID NO 100
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: TrxC-8

<400> SEQUENCE: 100

Thr Ala Arg Asn Phe Gln Val Val Ser Ile Pro Thr Leu Ile Leu Phe
1               5                  10                  15
```

Lys Asp Gly Gln
        20

<210> SEQ ID NO 101
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: TrxC-9

<400> SEQUENCE: 101

Pro Thr Leu Ile Leu Phe Lys Asp Gly Gln Pro Val Lys Arg Ile Val
1               5                   10                  15

Gly Ala Lys Gly
        20

<210> SEQ ID NO 102
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: TrxC-10

<400> SEQUENCE: 102

Pro Val Lys Arg Ile Val Gly Ala Lys Gly Lys Ala Ala Leu Leu Arg
1               5                   10                  15

Glu Leu Ser Asp
        20

<210> SEQ ID NO 103
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: TrxC-11

<400> SEQUENCE: 103

Gly Ala Lys Gly Lys Ala Ala Leu Leu Arg Glu Leu Ser Asp Val Val
1               5                   10                  15

Pro Asn Leu Asn
        20

<210> SEQ ID NO 104
<211> LENGTH: 30
<212> TYPE: PRT
<213> ORGANISM: Artificial Sequence
<220> FEATURE:
<223> OTHER INFORMATION: synthetic

<400> SEQUENCE: 104

Met Thr Glu Tyr Glu Gly Pro Lys Thr Lys Phe His Ala Leu Met Gln
1               5                   10                  15

Glu Gln Ile His Asn Glu Phe Thr Ala Ala Gln Gln Tyr Val
            20                  25                  30